US008349791B2

(12) United States Patent
Slusky et al.

(10) Patent No.: US 8,349,791 B2
(45) Date of Patent: Jan. 8, 2013

(54) POLYPEPTIDES THAT BIND MEMBRANE PROTEINS

(75) Inventors: Joanna S. Slusky, Stockholm (SE); Hang Yin, Boulder, CO (US); William F. DeGrado, Media, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 672 days.

(21) Appl. No.: 12/306,424

(22) PCT Filed: Jun. 29, 2007

(86) PCT No.: PCT/US2007/015425
§ 371 (c)(1),
(2), (4) Date: Sep. 29, 2009

(87) PCT Pub. No.: WO2008/005470
PCT Pub. Date: Jan. 10, 2008

(65) Prior Publication Data
US 2010/0120695 A1 May 13, 2010

Related U.S. Application Data

(60) Provisional application No. 60/818,094, filed on Jun. 30, 2006.

(51) Int. Cl.
*A61K 38/00* (2006.01)
*C07K 5/00* (2006.01)
*C07K 7/00* (2006.01)
*C07K 16/00* (2006.01)
*C07K 17/00* (2006.01)

(52) U.S. Cl. ............................ 514/1.1; 530/324; 530/326

(58) Field of Classification Search ........................ None
See application file for complete search history.

(56) References Cited

U.S. PATENT DOCUMENTS

| 6,560,542 B1 * | 5/2003 | Mandell et al. ................ 702/19 |
| 2002/0123071 A1 | 9/2002 | Knudsen et al. |
| 2004/0031072 A1 | 2/2004 | La Rosa |
| 2005/0079549 A1 | 4/2005 | Castracane |

OTHER PUBLICATIONS

Adamian et al. Helix-Helix Packing and Interfacial Pairwise Interactions of Residues in Membrane Proteins. JMB, 2001. vol. 311, pp. 891-907.*
Dobbs et al. Optimal potentials for predicting inter-helical packing in transmembrane proteins. Proteins: Structure, Function, and Bioinformatics. 2002. vol. 49, Issue 3, pp. 342-349.*
Melnyk et al. The Affinity of GXXXG Motifs in Transmembrane Helix-Helix Interactions iss Modulated by Long-range Communication. JBC. 2004. vol. 279, No. 16, pp. 16591-16597.*
Betz et al. Design of two-stranded and three-stranded coiled-coil peptides. Philosophical Transactions: Biological Sciences. 1995. vol. 348, No. 1323, pp. 81-88.*

Hruby. Designing peptide receptor agonists and antagonists. Nature Reviews. Drug Discovery. 2002. vol. 1, pp. 847-858.*
Adamian et al., "Empirical lipid propensities of amino acid residues in multispan α helical membrane proteins", Proteins Struct. Funct. Bioinformat., (no month available) 2005, 59, 496-509.
Adamian et al., "Interhelical hydrogen bonds and spatial motifs in membrane proteins: polar clamps and serine zippers", Proteins, Mar. 1, 2002, 47(2), 209-218.
Al-Alem et al., "Impaired Ig Class Switch in Mice Deficient for the X-linked Lymphoproliferative Disease Gene Sap", Blood, Sep. 15, 2005, 106(6), 2069-2075.
Arkin et al., "A new data analysis method to determine binding constants of small molecules to proteins using equilibrium analytical ultracentrifugation with absorption optics", Anal. Biochem., Dec. 1, 2001, 299(1), 98-107.
Arnaout et al., "Integrin structure, allostery, and bidirectional signaling", Annu. Rev. Cell Dev. Biol., Jun. 28, 2005, 21, 381-410.
Batzri et al., "Single bilayer liposomes prepared without sonication", Biochim. Biophys. Acta, Apr. 16, 1973, 298(4), 1015-1019.
Bechinger, "Structure and functions of channel-forming peptides: magainins, cecropins, melittin and alamethicin", J. Membr. Biol., Apr. 1, 1997, 156(3), 197-211.
Bennett et al., "Agonist-activated $\alpha_v\beta_3$ platelets and lymphocytes binds to the matrix protein osteopontin", J. Biol. Chem., Mar. 28, 1997, 272(13), 8137-8140.
Bennett, "Novel platelet inhibitors", Annu. Rev. Med., Feb. 2001, 52, 161-184.
Bennett, "Structure and function of the platelet integrin αIIbβ3", J. Clin. Invest, Dec. 2005, 115(12), 3363-3369.
Binz et al., "Engineered proteins as specific binding reagents", Curr. Opin. Biotechnol., Aug. 2005, 16(4), 459-469.
Bowie "Helix packing in membrane proteins", J. Mol. Biol., Oct. 10, 1997, 272(5), 780-789.
Canutescu et al., "A graph-theory algorithm for rapid protein side-chain prediction", Protein Sci., Sep. 2003, 12(9), 2001-2014.
Carter, "Potent antibody therapeutics by design", Nat. Rev. Immunol., May 2006, 6(5), 343-357.
Choma et al., "Asparagine-mediated self-association of a model transmembrane helix", Nat. Struct. Biol., Feb. 2000, 7(2), 161-166.
Cohen et al., "α-helical coiled coils and bundles: how to design an α-helical protein", Proteins Struct., Funct., and Gen., May 1, 1990, 7, 1-15.
Coller et al., "Platelet vitronectin receptor expression differentiates Iraqi-Jewish from Arab patients with *Glanzmann thrombasthenia* in Israel", Blood, Jan. 1, 1991, 77(1), 75-83.
Curran et al., "Sequence motifs, polar interactions and conformational changes in helical membrane proteins", Curr. Opin. Struct. Biol., Aug. 2003, 13(4), 412-417.

(Continued)

*Primary Examiner* — Marcela M Cordero Garcia
(74) *Attorney, Agent, or Firm* — Woodcock Washburn, LLP

(57) ABSTRACT

Polypeptides which bind to the helical transmembrane region of membrane proteins are disclosed, as are methods for the design of polypeptides that bind to the transmembrane region of membrane proteins. Also provided are methods for the use of the disclosed polypeptides in various applications, as well as products made through the practice of the instant methods.

13 Claims, 16 Drawing Sheets

OTHER PUBLICATIONS

Daugherty et al., "A Fluorescence Assay for Leucine Zipper Dimerization: Avoiding Unintended Consequences of Fluorophore Attachment", J. Am. Chem. Soc., Apr. 24, 1999, 121(18), 4325-4333.
Desjarlais et al., "De novo design of the hydrophobic cores of proteins", Protein Sci., Oct. 1995, 4(10), 2006-2018.
Dieckmann et al., "Modeling transmembrane helical oligomers", Curr. Op. in Struct. Biol., Aug. 1997, 7(4), 486-494.
Doura et al., "Complex interactions at the helix-helix interface stabilize the glycophorin A transmembrane dimmer", J. Mol. Biol., Nov. 5, 2004, 343(5), 1487-1497.
Ebie et al., "Dimerization of the erythropoietin receptor transmembrane domain in micelles", J. Mol. Biol., Feb. 16, 2007, 366(2), 517-524.
Engelman et al., "Membrane protein folding: beyond the two stage model", FEBS Lett., Oct. 7, 2003, 555(1), 122-125.
Fairman et al., "Multiple oligomeric states regulate the DNA binding of helix-loop-helix peptides", Proc. Natl. Acad. Sci. USA, Nov. 15, 1993, 90(22), 10429-10433.
Fischer, "The design, synthesis and application of stereochemical and directional peptide isomers: a critical review", Curr. Protein Pept. Sci., Oct. 2003, 4(5), 339-356.
Fleming, "Standardizing the free energy change of transmembrane helix-helix interactions", J. Mol. Biol., Oct. 25, 2002, 323(3), 563-571.
Fouchet et al., "Recent advances of flow cytometry in fundamental and applied microbiology", Biol. Cell., (no month available) 1993, 78(1-2), 95-109.
Freeman-Cook et al., "Selection and characterization of small random transmembrane proteins that bind and activate the platelet-derived growth factor β receptor", J. Mol. Biol., May 14, 2004, 338(5), 907-920.
Gerber et al., "D-enantiomer peptide of the TCRα transmembrane domain inhibits T-cell activation in vitro and in vivo", FASEB J., Jul. 2005, 19(9), 1190-1192.
Gerber et al., "Structural adaptation of the glycophorin A transmembrane homodimer to D-amino acid modifications", J. Mol. Biol, May 21, 2004, 339(1), 243-250.
Gerber et al., "Two motifs within a transmembrane domain, one for homodimerization and the other for heterodimerization", J. Biol. Chem., May 14, 2004, 279(20), 21177-21182.
Ghirlanda et al., "From synthetic coiled coils to functional proteins: automated design of a receptor for the calmodulin-binding domain of calcineurin", J. Mol. Biol., Aug. 14, 1998, 281(2), 379-391.
Gimpelev et al., "Helical packing patterns in membrane and soluble proteins", Biophys., J., Dec. 2004, 87(6), 4075-4086.
Goldstein, "Efficient rotamer elimination applied to protein side-chains and related spin glasses", Biophys. J., May 1994, 66(5), 1335-1340.
Gottschalk, "A coiled-coil structure of the αIIbβ3 integrin transmembrane and cytoplasmic domains in its resting state", Structure, May 2005, 13(5), 703-712.
Harris et al., "Pegylation: a novel process for modifying pharmacokinetics", Clin. Pharmacokinet., (no month available) 2001, 40(7), 539-551.
Hope et al., "Production of large unilamellar vesicles by a rapid extrusion procedure. Characterization of size distribution, trapped volume and ability to maintain a membrane potential", Biochim. Biophys. Acta, Jan. 10, 1985, 812(1), 55-65.
Huang et al., "Structure and mechanism of the glycerol-3-phosphate transporter from *Escherichia coli*", Science, Aug. 1, 2003, 301(5633), 616-620.
Jordan et al., "Three-dimensional structure of cyanobacterial photosystem I at 2.5 A resolution", Nature, Jan. 21, 2001, 411(6840), 909-917.
Kharakoz, "Partial volumes and compressibilities of extended polypeptide chains in aqueous solution: additivity scheme and implication of protein unfolding at normal and high pressure", Biochemistry, Aug. 19, 1997, 36(33), 10276-10285.
Kim et al., "Transmembrane glycine zippers: physiological and pathological roles in membrane proteins", Proc. Natl. Acad. Sci. USA, Oct. 4, 2005, 102(40), 14278-14283.

Kirman et al., "Infliximab: mechanism of action beyond TNF-α neutralization in inflammatory bowel disease", Eur. J. Gastroenterol Hepatol., Jul. 2004, 16(7), 639-641.
Koike et al., "A novel ERK-dependent signaling process that regulates interleukin-2 expression in a late phase of T cell activation", J Biol. Chem., Mar. 2, 2003, 278(18), 15685-15692.
Kortemme et al., "Computational design of protein-protein interactions", Curr. Opin. Chem. Biol., Feb. 2004, 8(1), 91-97.
Ladokhin et al., "How to measure and analyze tryptophan fluorescence in membranes properly, and why bother?", Anal. Biochem., Oct. 15, 2000, 285(2), 235-245.
Lakowicz, "Principles of Fluorescence Spectroscopy", 2nd ed., Kluwer Acad., NY, (no month available) 1999, Chapter 1, p. 53.
Langosch et al., "Dimerisation of the glycophorin A transmembrane segment in membranes probed with the ToxR transcription activator", J. Mol. Biol., Nov. 8, 1996, 263(4), 525-530.
Laue et al., "Computer-aided interpretation of analytical sedimentation data for proteins", Analytical Ultracentrifugation in Biochemistry and Polymer Science, the Royal Society of Chemistry: Cambridge (U.K.), (no month available) 1992, Chapter 14, 90-125.
Lemmon et al., "Sequence specificity in the dimerization of transmembrane α-helices", Biochem., Dec. 29, 1992, 31(51), 12719-12725.
Li et al., "A push-pull mechanism for regulating integrin function", Proc. Natl. Acad. Sci. USA, Feb. 1, 2005, 102(5), 1424-1429.
Li et al., "Dimerization of the transmembrane domain of Integrin αIIb subunit in cell membranes", J. Biol. Chem., Jun. 18, 2004, 279(25), 26666-26673.
Lipman et al., "Monoclonal versus polyclonal antibodies: distinguishing characteristics, applications, and information resources", ILAR J., (no month available) 2005, 46(3), 258-268.
Litvinov et al., "Binding strength and activation state of single fibrinogen-integrin pairs on living cells", Proc. Natl. Acad. Sci. USA, May 28, 2002, 99(11), 7426-7431.
Litvinov et al., "Quantitative analysis of platelet $\alpha_v\beta_3$ binding to osteopontin using laser tweezers", J. Biol. Chem., Dec. 19, 2003, 278(51), 51285-51290.
Liu et al., "De novo design, synthesis, and characterization of antimicrobial β-peptides", J. Am. Chem. Soc., Aug. 8, 2001, 123(31), 7553-7559.
Liu et al., "Effect of Variations in the Structure of a Polyleucine-Based a-Helical Transmembrane Peptide on Its Interaction with Phosphatidylethanolamine Bilayers", Biophys. J., Oct. 2004, 87(4), 2470-2482.
Lopez De Le Paz et al., "Sequence determinants of amyloid fibril formation", Proc. Natl. Acad. Sci. USA, Jan. 6, 2004, 101(1), 87-92.
Luo et al., "A specific interface between integrin transmembrane helices and affinity for ligand", PLoS Biology, Jun. 15, 2004, 2(6), 776-786.
Luo et al., "Disrupting integrin transmembrane domain heterodimerization increases ligand binding affinity, not valency or clustering", Proc. Natl. Acad. Sci. USA, Mar. 8, 2005, 102(10), 3679-3684.
MacBeath et al., "Printing proteins as microarrays for high-throughput function determination", Science, Sep. 8, 2000, 289(5485), 1760-1763.
MacKenzie et al., "A transmembrane helix dimer: structure and implications", Science, Apr. 4, 1997, 276(5309), 131-133.
Manolios et al., "T-cell antigen receptor transmembrane peptides modulate T-cell function and T cell-mediated disease", Nat. Med., Jan. 1, 1997, 3, 84-88.
Mayer et al., "Vesicles of variable sizes produced by a rapid extrusion procedure", Biochim. Biophys. Acta, Jun. 13, 1986, 858(1), 161-168.
Melnyk et al, "Polar residue tagging of transmembrane peptides", Biopolymers, (no month available) 2003, 71(6), 675-685.
Ogihara et al., "Design of three-dimensional domain-swapped dimers and fibrous oligomers", Proc. Natl. Acad. Sci., USA, Feb. 13, 2001, 98(4), 1404-1409.
Ottemann et al., "ToxR proteins with substitutions in residues conserved with OmpR fail to activate transcription from the cholera toxin promoter", J. Bacteriol., Nov. 1992, 174(21), 6807-6814.

Partridge et al., "A transmembrane segment mimic derived from *Escherichia coli* diacylglycerol kinase inhibits protein activity", J. Biol. Chem., Jun. 13, 2003, 278(24), 22056-22060.

Partridge et al., "Transmembrane domain helix packing stabilizes integrin αIIbβ3 in the low affinity state", J. Biol. Chem., Feb. 25, 2005, 280(8), 7294-7300.

Reina et al., "Computer-aided design of a PDZ domain to recognize new target sequences", Nat. Struct. Biol., Jun. 24, 2002, 9(8), 621-627.

Russ et al., "TOXCAT: a measure of transmembrane helix association in a biological membrane", Proc. Natl. Acad. Sci USA, Feb. 2, 1999, 96(3), 863-868.

Senes et al., "E(z), a depth-dependent potential for assessing the energies of insertion of amino acid side-chains into membranes: derivation and applications to determining the orientation of transmembrane and interfacial helices", J. Mol. Biol., Feb. 16, 2007, 366(2), 436-448.

Senes et al., "Folding of helical membrane proteins: the role of polar, GxxxG-like and proline motifs", Curr. Opin. Struct. Biol., Aug. 2004, 14(4), 465-479.

Senes et al., "Statistical analysis of amino acid patterns in transmembrane helices: the GxxxG motif occurs frequently and in association with β-branched residues at neighboring positions", J. Mol. Biol., Feb. 25, 2000, 296(3), 921-936.

Senes et al., "The Cα-H···O hydrogen bond: a determinant of stability and specificity in transmembrane helix interactions", Proc. Natl. Acad. Sci. USA, Jul. 31, 2001, 98(16), 9056-9061.

Shifman et al., "Exploring the origins of binding specificity through the computational redesign of calmodulin", Proc. Acad. Natl. Sci., USA, Nov. 11, 2003, 100(23), 13274-13279.

Stockener et al., "Direct Stimulation of Transmembrane Helix Association: Role of Asparagines", Biophysical Journal, Sep. 1, 2004, 87(3), 1650-1656.

Summa et al., "Computational de novo design, and characterization of an A(2)B(2) diiron protein", J. Mol. Biol., Aug. 30, 2002, 321(5), 923-938.

Takagi et al., "Integrin activation and structural rearrangement", Immunol. Rev., Aug. 2002, 186, 141-163.

Tanford et al., "Characterization of membrane proteins in detergent solutions", Biochim. Biophys. Acta, Oct. 26, 1976, 457(2), 133-170.

Ulmschneider et al., "Properties of integral membrane protein structures: derivation of an implicit membrane potential", Proteins Struct. Funct. Bioinformat., May 1, 2005, 59(2), 252-265.

Walters et al., "Helix-packing motifs in membrane proteins," Proc. Nat'l. Acad. Sci., Sep. 12, 2006, 103(37), 13658-13663, Epublished on Sep. 5, 2006.

Wegener et al., "Structural basis of integrin activation by talin", Cell, Jan. 12, 2007, 128(1), 171-182.

Weisel et al., "Examination of the platelet membrane glycoprotein IIb-IIIa complex and its interaction with fibrinogen and other ligands by electron microscopy", J. Biol. Chem., Aug. 15, 1992, 267(23), 16637-16643.

Winter, "Synthetic human antibodies and a strategy for protein engineering" FEBS Lett., Jun. 23, 1998, 430(1-2), 92-94.

Wu et al., "Arming antibodies: prospects and challenges for immunoconjugates" Nat. Biotechnol., Sep. 2005, 23(9), 1137-1146.

Xu et al., "Catalytic Antibodies: Hapten design strategies and screening methods", Bioorg. Med. Chem., Oct. 15, 2004, 12(20), 5247-5268.

Yin et al., "Computational design of peptides that target transmembrane helices", Science, Mar. 30, 2007, 315(5820), 1817-1822.

Yin et al., "Terphenyl-Based Bak BH3 α-helical proteomimetics as low-molecular-weight antagonists of Bcl-xL", J. Am. Chem. Soc., Jul. 27, 2005, 127(29), 10191-10196.

Yin, "Activation of platelet αIIbβ3 by an exogenous peptide corresponding to the transmembrane domain of αIIb", J. Biol. Chem., Dec. 1, 2006, 281(48), 36732-36741.

\* cited by examiner

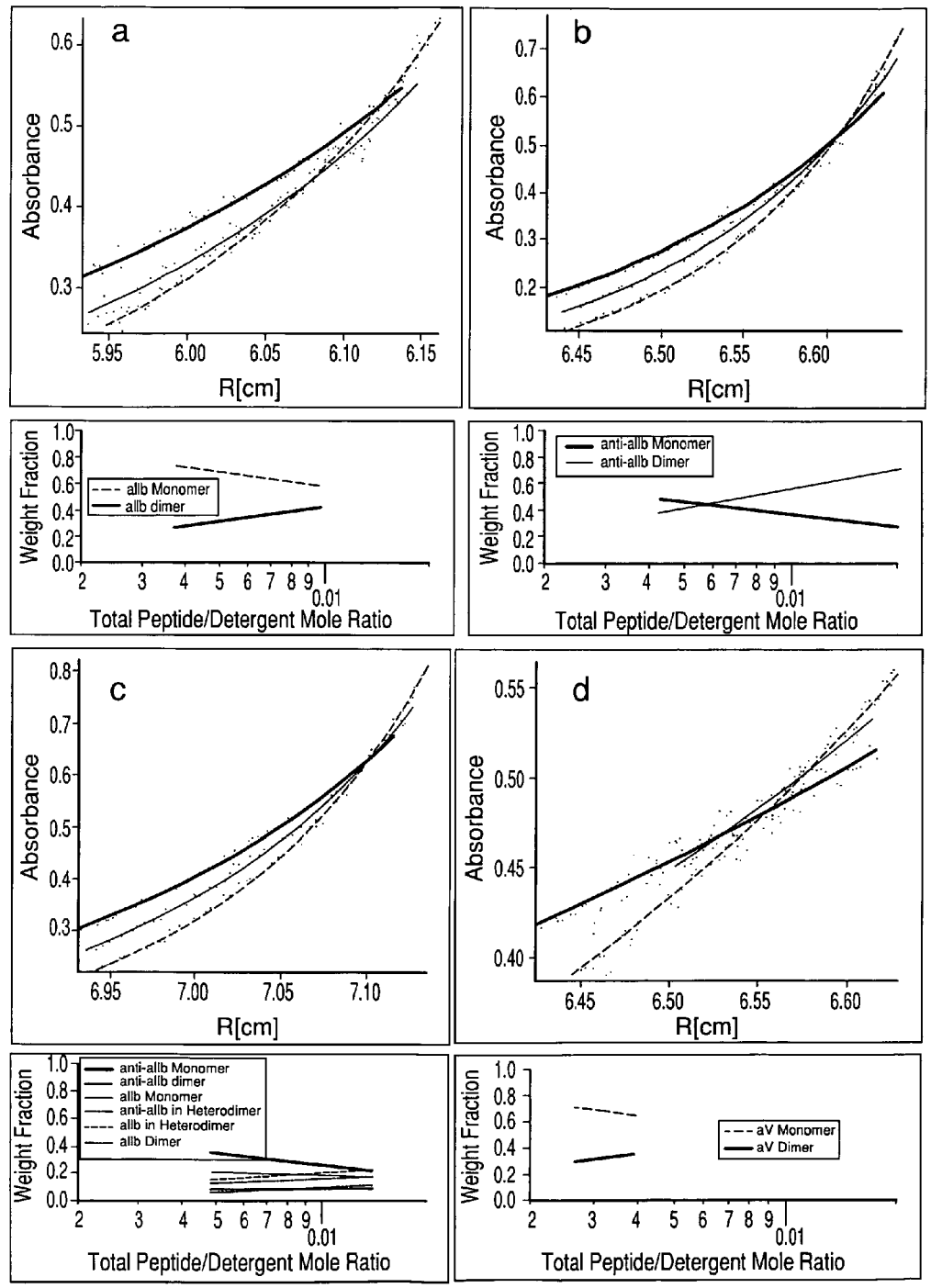
FIG. 8a-d

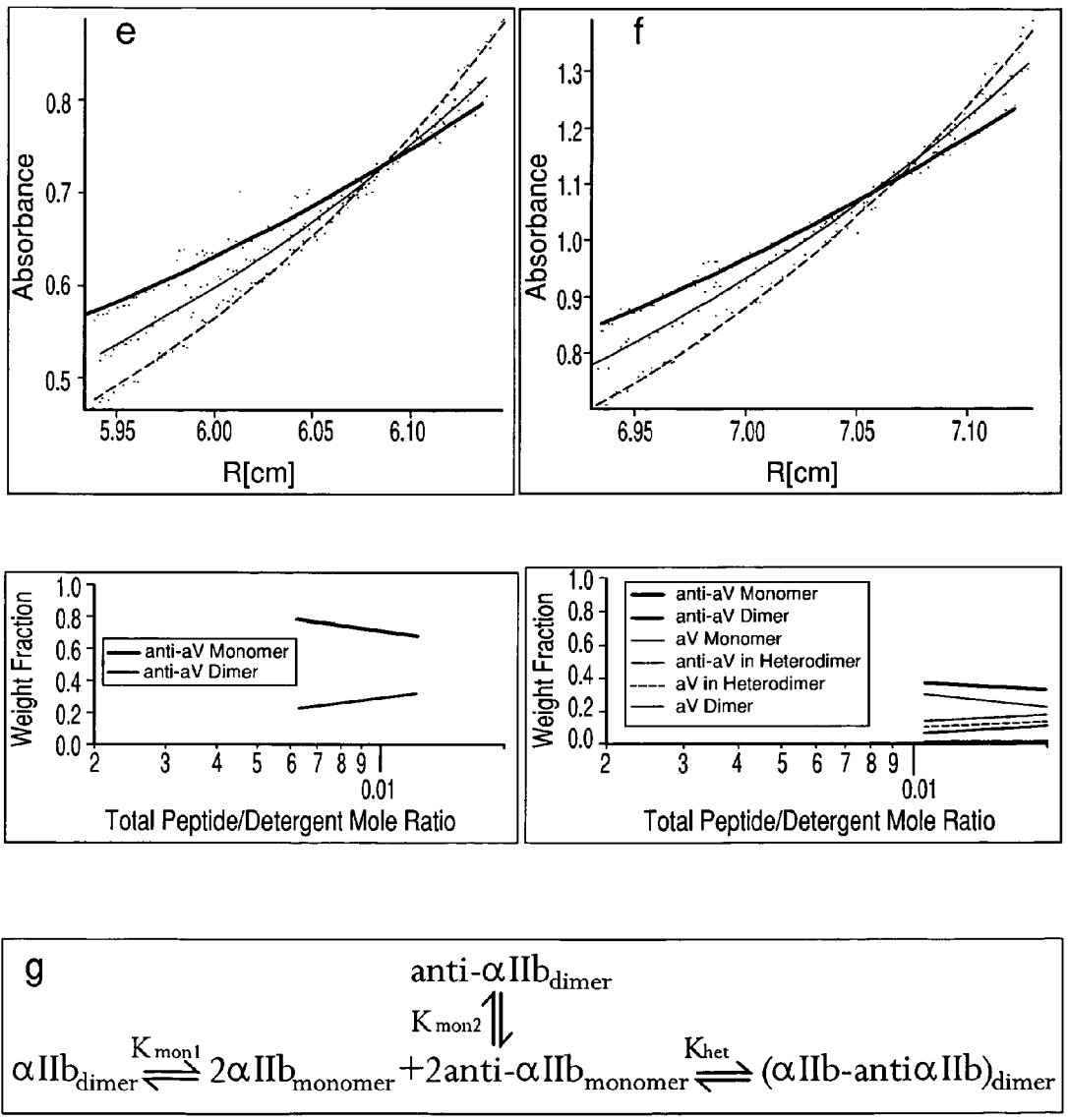
FIG. 8e-g

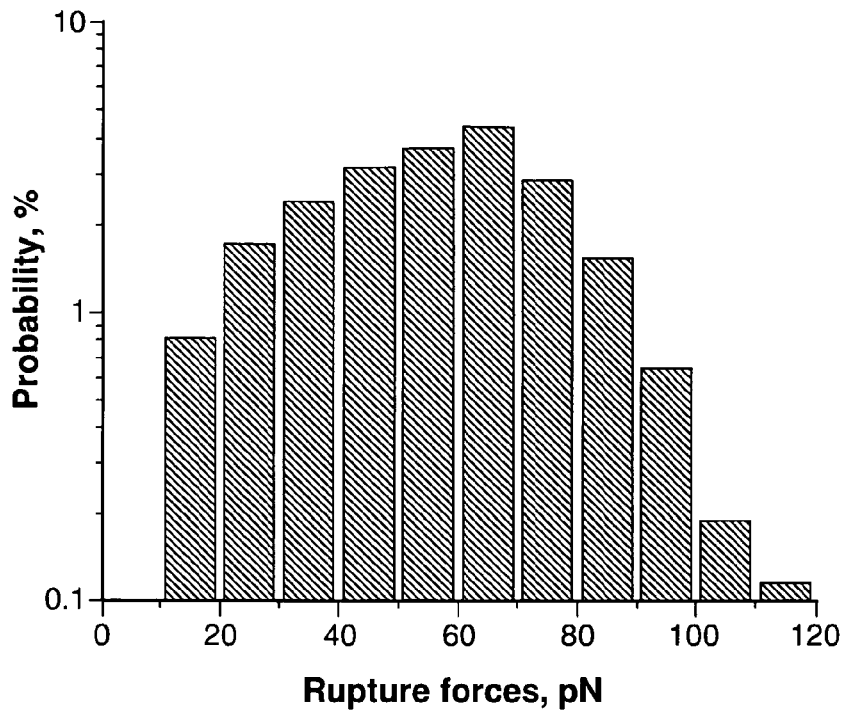
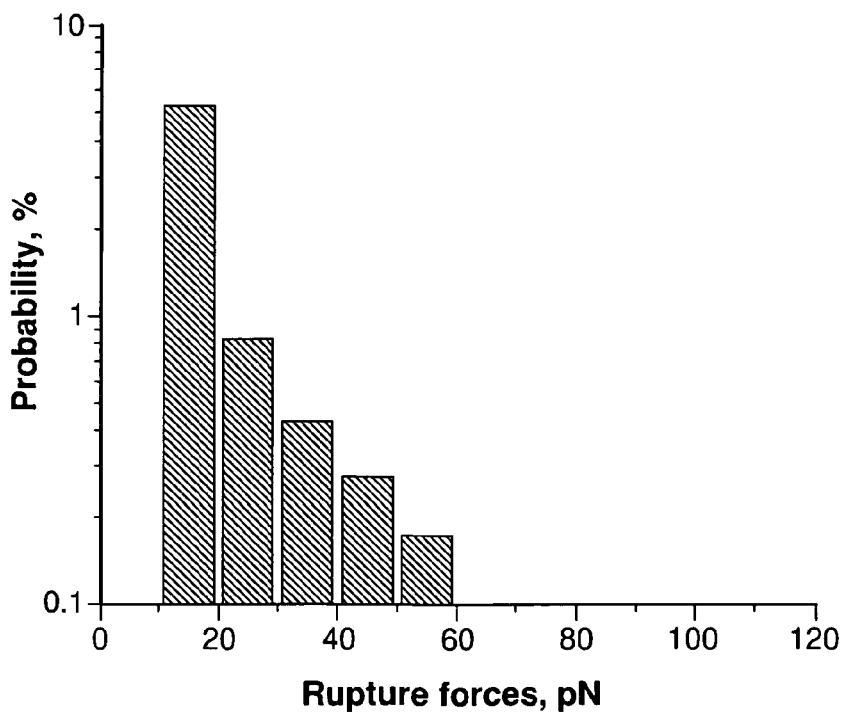
FIG. 12

SEQUENCE LISTING

<160> NUMBER OF SEQ ID NOS: 41

<210> SEQ ID NO 1
<211> LENGTH: 15
<212> TYPE: PRT
<213> ORGANISM: Artificial Sequence

```
<220> FEATURE:
<223> OTHER INFORMATION: Synthetic construct
<220> FEATURE:
<221> NAME/KEY: MISC_FEATURE
<222> LOCATION: (1)..(3)
<223> OTHER INFORMATION: Xaa can be any naturally occurring amino acid
      or synthetic amino acid
<220> FEATURE:
<221> NAME/KEY: MISC_FEATURE
<222> LOCATION: (5)..(8)
<223> OTHER INFORMATION: Xaa can be any naturally occurring amino acid
      or synthetic amino acid
<220> FEATURE:
<221> NAME/KEY: MISC_FEATURE
<222> LOCATION: (12)..(13)
<223> OTHER INFORMATION: Xaa can be any naturally occurring amino acid
      or synthetic amino acid

<400> SEQUENCE: 1

Xaa Xaa Xaa Met Xaa Xaa Xaa Xaa Phe Ile Gly Xaa Xaa Leu Gly
1               5                   10                  15

<210> SEQ ID NO 2
<211> LENGTH: 29
<212> TYPE: PRT
<213> ORGANISM: Artificial Sequence
<220> FEATURE:
<223> OTHER INFORMATION: Synthetic construct

<400> SEQUENCE: 2

Ala Tyr Val Met Leu Leu Pro Phe Phe Ile Gly Leu Leu Leu Gly Leu
1               5                   10                  15

Ile Phe Gly Gly Ala Phe Trp Gly Pro Ala Arg His Leu
            20                  25

<210> SEQ ID NO 3
<211> LENGTH: 87
<212> TYPE: DNA
<213> ORGANISM: Artificial Sequence
<220> FEATURE:
<223> OTHER INFORMATION: Oligonucleotide primer

<400> SEQUENCE: 3
gcgtatgtga tgctgctgcc gttttttcatt ggcctgcttc tgggcctgat ttttggcggt    60
gcgttttggg gcccggcgcg ccatctg                                        87

<210> SEQ ID NO 4
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(2)
<223> OTHER INFORMATION: Xaa can be any naturally occurring amino acid
      or synthetic amino acid
<220> FEATURE:
<221> NAME/KEY: MISC_FEATURE
<222> LOCATION: (4)..(5)
<223> OTHER INFORMATION: Xaa can be any naturally occurring amino acid
      or synthetic amino acid
<220> FEATURE:
<221> NAME/KEY: MISC_FEATURE
<222> LOCATION: (8)..(9)
<223> OTHER INFORMATION: Xaa can be any naturally occurring amino acid
      or synthetic amino acid
<220> FEATURE:
<221> NAME/KEY: MISC_FEATURE
<222> LOCATION: (12)..(13)
<223> OTHER INFORMATION: Xaa can be any naturally occurring amino acid
      or synthetic amino acid
```

```
<220> FEATURE:
<221> NAME/KEY: MISC_FEATURE
<222> LOCATION: (16)..(17)
<223> OTHER INFORMATION: Xaa can be any naturally occurring amino acid
      or synthetic amino acid
<220> FEATURE:
<221> NAME/KEY: MISC_FEATURE
<222> LOCATION: (20)..(21)
<223> OTHER INFORMATION: Xaa can be any naturally occurring amino acid
      or synthetic amino acid
<220> FEATURE:
<221> NAME/KEY: MISC_FEATURE
<222> LOCATION: (24)..(25)
<223> OTHER INFORMATION: Xaa can be any naturally occurring amino acid
      or synthetic amino acid
<220> FEATURE:
<221> NAME/KEY: MISC_FEATURE
<222> LOCATION: (27)..(29)
<223> OTHER INFORMATION: Xaa can be any naturally occurring amino acid
      or synthetic amino acid

<400> SEQUENCE: 4

Xaa Xaa Gly Xaa Xaa Thr Phe Xaa Xaa Gly Tyr Xaa Xaa Gly Ala Xaa
1               5                   10                  15

Xaa Thr Gly Xaa Xaa Tyr Trp Xaa Xaa Gln Xaa Xaa Xaa
            20                  25

<210> SEQ ID NO 5
<211> LENGTH: 33
<212> TYPE: PRT
<213> ORGANISM: Artificial Sequence
<220> FEATURE:
<223> OTHER INFORMATION: Synthetic construct

<400> SEQUENCE: 5

Lys Lys Ile Phe Gly Val Leu Thr Phe Leu Phe Gly Tyr Ile Leu Gly
1               5                   10                  15

Ala Leu Ile Thr Gly Ala Val Tyr Trp Phe Val Gln Leu Leu Ala Lys
            20                  25                  30

Lys

<210> SEQ ID NO 6
<211> LENGTH: 87
<212> TYPE: DNA
<213> ORGANISM: Artificial Sequence
<220> FEATURE:
<223> OTHER INFORMATION: Oligonucleotide primer

<400> SEQUENCE: 6
atcttcggtg ttctgacctt cctgttcggt tacatcctgg gtgctctgat caccggtgct    60
gtttactggt tcgttcagct gctggct                                        87

<210> SEQ ID NO 7
<211> LENGTH: 23
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(4)
<223> OTHER INFORMATION: Xaa can be any naturally occurring amino acid
      or synthetic amino acid
<220> FEATURE:
<221> NAME/KEY: MISC_FEATURE
<222> LOCATION: (6)..(7)
<223> OTHER INFORMATION: Xaa can be any naturally occurring amino acid
      or synthetic amino acid
<220> FEATURE:
<221> NAME/KEY: MISC_FEATURE
```

```
<222> LOCATION: (10)..(11)
<223> OTHER INFORMATION: Xaa can be any naturally occurring amino acid
      or synthetic amino acid
<220> FEATURE:
<221> NAME/KEY: MISC_FEATURE
<222> LOCATION: (14)..(15)
<223> OTHER INFORMATION: Xaa can be any naturally occurring amino acid
      or synthetic amino acid
<220> FEATURE:
<221> NAME/KEY: MISC_FEATURE
<222> LOCATION: (17)..(19)
<223> OTHER INFORMATION: Xaa can be any naturally occurring amino acid
      or synthetic amino acid
<220> FEATURE:
<221> NAME/KEY: MISC_FEATURE
<222> LOCATION: (22)..(23)
<223> OTHER INFORMATION: Xaa can be any naturally occurring amino acid
      or synthetic amino acid

<400> SEQUENCE: 7

Xaa Xaa Xaa Xaa Ile Xaa Xaa Ser Phe Xaa Xaa Gly Thr Xaa Xaa Gly
1               5                   10                  15

Xaa Xaa Xaa Met Phe Xaa Xaa
            20

<210> SEQ ID NO 8
<211> LENGTH: 23
<212> TYPE: PRT
<213> ORGANISM: Artificial Sequence
<220> FEATURE:
<223> OTHER INFORMATION: Synthetic construct

<400> SEQUENCE: 8

Ala Tyr Val Phe Ile Leu Leu Ser Phe Ile Leu Gly Thr Leu Leu Gly
1               5                   10                  15

Phe Leu Val Met Phe Trp Ala
            20

<210> SEQ ID NO 9
<211> LENGTH: 69
<212> TYPE: DNA
<213> ORGANISM: Artificial Sequence
<220> FEATURE:
<223> OTHER INFORMATION: Oligonucleotide primer

<400> SEQUENCE: 9
gcttacgttt tcatcctgct gtctttcatc ctgggtaccc tgctgggttt cctggttatg        60
ttctgggct                                                                69

<210> SEQ ID NO 10
<211> LENGTH: 25
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(2)
<223> OTHER INFORMATION: Xaa can be any naturally occurring amino acid
      or synthetic amino acid
<220> FEATURE:
<221> NAME/KEY: MISC_FEATURE
<222> LOCATION: (5)..(6)
<223> OTHER INFORMATION: Xaa can be any naturally occurring amino acid
      or synthetic amino acid
<220> FEATURE:
<221> NAME/KEY: MISC_FEATURE
<222> LOCATION: (8)..(9)
<223> OTHER INFORMATION: Xaa can be any naturally occurring amino acid
      or synthetic amino acid
<220> FEATURE:
```

```
<221> NAME/KEY: MISC_FEATURE
<222> LOCATION: (12)..(12)
<223> OTHER INFORMATION: Xaa can be any naturally occurring amino acid
      or synthetic amino acid
<220> FEATURE:
<221> NAME/KEY: MISC_FEATURE
<222> LOCATION: (15)..(16)
<223> OTHER INFORMATION: Xaa can be any naturally occurring amino acid
      or synthetic amino acid
<220> FEATURE:
<221> NAME/KEY: MISC_FEATURE
<222> LOCATION: (18)..(19)
<223> OTHER INFORMATION: Xaa can be any naturally occurring amino acid
      or synthetic amino acid
<220> FEATURE:
<221> NAME/KEY: MISC_FEATURE
<222> LOCATION: (21)..(23)
<223> OTHER INFORMATION: Xaa can be any naturally occurring amino acid
      or synthetic amino acid
<220> FEATURE:
<221> NAME/KEY: MISC_FEATURE
<222> LOCATION: (25)..(25)
<223> OTHER INFORMATION: Xaa can be any naturally occurring amino acid
      or synthetic amino acid

<400> SEQUENCE: 10

Xaa Xaa Trp Phe Xaa Xaa Phe Xaa Xaa Ile Phe Xaa Gly Phe Xaa Xaa
1               5                   10                  15

Gly Xaa Xaa Thr Xaa Xaa Xaa Gln Xaa
            20                  25

<210> SEQ ID NO 11
<211> LENGTH: 25
<212> TYPE: PRT
<213> ORGANISM: Artificial Sequence
<220> FEATURE:
<223> OTHER INFORMATION: Synthetic construct

<400> SEQUENCE: 11

Arg Ala Trp Phe Ala Leu Phe Leu Leu Ile Phe Leu Gly Phe Leu Leu
1               5                   10                  15

Gly Val Ala Thr Leu Leu Val Gln Tyr
            20                  25

<210> SEQ ID NO 12
<211> LENGTH: 5
<212> TYPE: PRT
<213> ORGANISM: Homo Sapiens
<220> FEATURE:
<221> NAME/KEY: MISC_FEATURE
<222> LOCATION: (2)..(4)
<223> OTHER INFORMATION: Xaa can be any naturally occurring amino acid
      or synthetic amino acid

<400> SEQUENCE: 12

Gly Xaa Xaa Xaa Gly
1               5

<210> SEQ ID NO 13
<211> LENGTH: 23
<212> TYPE: PRT
<213> ORGANISM: Artificial Sequence
<220> FEATURE:
<223> OTHER INFORMATION: Synthetic construct

<400> SEQUENCE: 13

Pro Ile Leu Arg Gly Leu Glu Val Gly Met Ala His Gly Tyr Phe Leu
1               5                   10                  15

Ile Gly Pro Trp Val Lys Leu
            20
```

```
<210> SEQ ID NO 14
<211> LENGTH: 29
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(3)
<223> OTHER INFORMATION: Xaa can be any naturally occurring amino acid
      or synthetic amino acid
<220> FEATURE:
<221> NAME/KEY: MISC_FEATURE
<222> LOCATION: (5)..(6)
<223> OTHER INFORMATION: Xaa can be any naturally occurring amino acid
      or synthetic amino acid
<220> FEATURE:
<221> NAME/KEY: MISC_FEATURE
<222> LOCATION: (9)..(10)
<223> OTHER INFORMATION: Xaa can be any naturally occurring amino acid
      or synthetic amino acid
<220> FEATURE:
<221> NAME/KEY: MISC_FEATURE
<222> LOCATION: (13)..(13)
<223> OTHER INFORMATION: Xaa can be any naturally occurring amino acid
      or synthetic amino acid
<220> FEATURE:
<221> NAME/KEY: MISC_FEATURE
<222> LOCATION: (17)..(17)
<223> OTHER INFORMATION: Xaa can be any naturally occurring amino acid
      or synthetic amino acid
<220> FEATURE:
<221> NAME/KEY: MISC_FEATURE
<222> LOCATION: (21)..(22)
<223> OTHER INFORMATION: Xaa can be any naturally occurring amino acid
      or synthetic amino acid
<220> FEATURE:
<221> NAME/KEY: MISC_FEATURE
<222> LOCATION: (26)..(26)
<223> OTHER INFORMATION: Xaa can be any naturally occurring amino acid
      or synthetic amino acid

<400> SEQUENCE: 14

Xaa Xaa Xaa Met Xaa Xaa Pro Phe Xaa Xaa Gly Leu Xaa Leu Gly Leu
1               5                   10                  15

Xaa Phe Gly Gly Xaa Xaa Trp Gly Pro Xaa Arg His Leu
            20                  25

<210> SEQ ID NO 15
<211> LENGTH: 33
<212> TYPE: PRT
<213> ORGANISM: Artificial Sequence
<220> FEATURE:
<223> OTHER INFORMATION: Synthetic construct

<400> SEQUENCE: 15

Lys Lys Ala Tyr Val Met Leu Leu Pro Phe Phe Ile Gly Leu Leu Leu
1               5                   10                  15

Gly Leu Ile Phe Gly Gly Ala Phe Trp Gly Pro Ala Arg His Leu Lys
            20                  25                  30

Lys

<210> SEQ ID NO 16
<211> LENGTH: 27
<212> TYPE: PRT
<213> ORGANISM: Artificial Sequence
<220> FEATURE:
<223> OTHER INFORMATION: Synthetic construct

<400> SEQUENCE: 16
```

Ser Glu Gly Trp Ser Gln Phe Thr Ala Gly Phe Phe Val Gly Ala Met
1               5                   10                  15

Gly Ser Ala Phe Val Ala Phe Phe Leu Leu Glu
            20                  25

<210> SEQ ID NO 17
<211> LENGTH: 27
<212> TYPE: PRT
<213> ORGANISM: Artificial Sequence
<220> FEATURE:
<223> OTHER INFORMATION: Synthetic construct

<400> SEQUENCE: 17

Ala Ile Pro Ile Trp Trp Val Leu Val Gly Val Leu Gly Gly Leu Leu
1               5                   10                  15

Leu Leu Thr Ile Leu Val Leu Ala Met Trp Lys
            20                  25

<210> SEQ ID NO 18
<211> LENGTH: 23
<212> TYPE: PRT
<213> ORGANISM: Artificial Sequence
<220> FEATURE:
<223> OTHER INFORMATION: Synthetic construct

<400> SEQUENCE: 18

Trp Val Leu Val Gly Val Leu Gly Gly Leu Leu Leu Leu Thr Ile Leu
1               5                   10                  15

Val Leu Ala Met Trp Lys Arg
            20

<210> SEQ ID NO 19
<211> LENGTH: 23
<212> TYPE: PRT
<213> ORGANISM: Artificial Sequence
<220> FEATURE:
<223> OTHER INFORMATION: Synthetic construct

<400> SEQUENCE: 19

Asp Leu Gly Phe Ala Leu Ser Gly Ile Ser Ile Ala Tyr Gly Phe Ser
1               5                   10                  15

Lys Phe Ile Met Gly Ser Val
            20

<210> SEQ ID NO 20
<211> LENGTH: 21
<212> TYPE: PRT
<213> ORGANISM: Artificial Sequence
<220> FEATURE:
<223> OTHER INFORMATION: Synthetic construct

<400> SEQUENCE: 20

Ala Val Met Phe Val Leu Leu Phe Leu Cys Gly Trp Phe Gln Gly Met
1               5                   10                  15

Gly Trp Pro Pro Cys
            20

<210> SEQ ID NO 21
<211> LENGTH: 21
<212> TYPE: PRT
<213> ORGANISM: Artificial Sequence
<220> FEATURE:
<223> OTHER INFORMATION: Synthetic construct

<400> SEQUENCE: 21

-continued

```
Pro Val Trp Val Ile Ile Leu Ala Val Leu Ala Gly Leu Leu Leu Leu
1               5                   10                  15

Ala Val Leu Val Phe
            20

<210> SEQ ID NO 22
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(4)
<223> OTHER INFORMATION: Xaa can be any naturally occurring amino acid
      or synthetic amino acid

<400> SEQUENCE: 22

Ala Xaa Xaa Xaa Gly
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(4)
<223> OTHER INFORMATION: Xaa can be any naturally occurring amino acid
      or synthetic amino acid
<220> FEATURE:
<221> NAME/KEY: MISC_FEATURE
<222> LOCATION: (6)..(8)
<223> OTHER INFORMATION: Xaa can be any naturally occurring amino acid
      or synthetic amino acid

<400> SEQUENCE: 23

Gly Xaa Xaa Xaa Gly Xaa Xaa Xaa Gly
1               5

<210> SEQ ID NO 24
<211> LENGTH: 51
<212> TYPE: DNA
<213> ORGANISM: Artificial Sequence
<220> FEATURE:
<223> OTHER INFORMATION: Oligonucleotide primer

<400> SEQUENCE: 24 ttttttttg catgcaccgg tgtttaaaca aggagatggc gcccaacagt c          51

<210> SEQ ID NO 25
<211> LENGTH: 45
<212> TYPE: DNA
<213> ORGANISM: Artificial Sequence
<220> FEATURE:
<223> OTHER INFORMATION: Oligonucleotide primer

<400> SEQUENCE: 25 ttttttttc catggactag tgtatatctc cttcttaaag ttaaa                 45

<210> SEQ ID NO 26
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 26
```
aaaaaaaaag ctagcgacgt cgcgtat                                         27

<210> SEQ ID NO 27
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 27
aaaaaaaaag gatccctcga gcagatg                                         27

<210> SEQ ID NO 28
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 28
aaaaaaaaag catgctcgac gaatttctgc cattc                                35

<210> SEQ ID NO 29
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 29
aaaaaaaaaa aaaataggcg tatcacgagg c                                    31

<210> SEQ ID NO 30
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 30
aaaaaaaata ctagtatgtt cggattagga cacaactc                             38

<210> SEQ ID NO 31
<211> LENGTH: 63
<212> TYPE: DNA
<213> ORGANISM: Artificial Sequence
<220> FEATURE:
<223> OTHER INFORMATION: Oligonucleotide primer

<400> SEQUENCE: 31
aaaaaaatta agcttttacg cataatccgg cacatcatac ggataagtct gcgcgtcttt     60
cag                                                                   63

<210> SEQ ID NO 32
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 32
aaaaaaattg gtacctccat ggtcggatta ggacacaact ca                        42

<210> SEQ ID NO 33
<211> LENGTH: 66

-continued

<212> TYPE: DNA
<213> ORGANISM: Artificial Sequence
<220> FEATURE:
<223> OTHER INFORMATION: Oligonucleotide primer

<400> SEQUENCE: 33
aaaaaaaaat taattaatca gatcttcttc gctaatcagt ttctgttcag tctgcgcgtc    60
tttcag                                                               66

<210> SEQ ID NO 34
<211> LENGTH: 9
<212> TYPE: PRT
<213> ORGANISM: Artificial Sequence
<220> FEATURE:
<223> OTHER INFORMATION: Synthetic construct

<400> SEQUENCE: 34

Tyr Pro Tyr Asp Val Pro Asp Tyr Ala
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic construct

<400> SEQUENCE: 35

Glu Gln Lys Leu Ile Ser Glu Glu Asp Leu
1               5                   10

<210> SEQ ID NO 36
<211> LENGTH: 24
<212> TYPE: PRT
<213> ORGANISM: Artificial Sequence
<220> FEATURE:
<223> OTHER INFORMATION: Synthetic construct

<400> SEQUENCE: 36

Lys Trp Val Leu Val Gly Val Leu Gly Gly Leu Leu Leu Leu Thr Ile
1               5                   10                  15

Leu Val Leu Ala Met Trp Lys Lys
            20

<210> SEQ ID NO 37
<211> LENGTH: 23
<212> TYPE: PRT
<213> ORGANISM: Artificial Sequence
<220> FEATURE:
<223> OTHER INFORMATION: Synthetic construct

<400> SEQUENCE: 37

Lys Pro Val Trp Val Ile Ile Leu Ala Val Leu Ala Gly Leu Leu Leu
1               5                   10                  15

Leu Ala Val Leu Val Phe Lys
            20

<210> SEQ ID NO 38
<211> LENGTH: 24
<212> TYPE: PRT
<213> ORGANISM: Artificial Sequence
<220> FEATURE:
<223> OTHER INFORMATION: Synthetic construct

<400> SEQUENCE: 38

Lys Gly Val Ile Ile Gly Ser Ile Ile Ala Gly Ile Leu Leu Leu Leu

-continued

```
1               5                   10                  15

Ala Leu Val Ala Ile Leu Trp Lys
            20

<210> SEQ ID NO 39
<211> LENGTH: 26
<212> TYPE: PRT
<213> ORGANISM: Artificial Sequence
<220> FEATURE:
<223> OTHER INFORMATION: Synthetic construct

<400> SEQUENCE: 39

Lys Ile Ile Pro Ile Val Ala Gly Val Val Ala Gly Ile Val Leu Ile
1               5                   10                  15

Gly Leu Ala Leu Leu Leu Ile Trp Lys Lys
            20                  25

<210> SEQ ID NO 40
<211> LENGTH: 25
<212> TYPE: PRT
<213> ORGANISM: Artificial Sequence
<220> FEATURE:
<223> OTHER INFORMATION: Synthetic construct

<400> SEQUENCE: 40

Lys Ile Leu Val Val Leu Leu Ser Val Met Gly Ala Ile Leu Leu Ile
1               5                   10                  15

Gly Leu Ala Ala Leu Leu Ile Trp Lys
            20                  25

<210> SEQ ID NO 41
<211> LENGTH: 4
<212> TYPE: PRT
<213> ORGANISM: Artificial Sequence
<220> FEATURE:
<223> OTHER INFORMATION: Synthetic construct

<400> SEQUENCE: 41

Arg Gly Asp Ser
1
```

POLYPEPTIDES THAT BIND MEMBRANE PROTEINS

CROSS-REFERENCE TO RELATED APPLICATIONS

This application is the National Stage of International Application No. PCT/US2007/015425, filed Jun. 29, 2007, which claims the benefit of U.S. Provisional Application No. 60/818,094, filed Jun. 30, 2006, the disclosures of which are incorporated herein by reference in their entirety.

GOVERNMENT RIGHTS

Research leading to the disclosed invention was funded, in part, by the U.S. National Institutes of Health, Grant Nos. GM60610 and GM54616. Accordingly, the United States Government may have rights in the invention described herein.

FIELD OF THE INVENTION

The present invention relates to polypeptides that bind to the helical transmembrane region of membrane proteins with high affinity and specificity. Also disclosed are methods for the design of these polypeptides. There are also provided methods for the use of such polypeptides in various applications, as well as products made through the practice of the instant methods.

BACKGROUND OF THE INVENTION

Antibodies have traditionally been used as research tools, and have more recently been developed for use as diagnostics and in drugs and therapeutic applications.

Antibodies are widely utilized for analysis, purification, and enrichment. Research and clinical applications that make use of antibodies are extremely common and encompass a wide variety of subject matters. See Lipman N S, Jackson L R, Trudel L I, Weis-Garcia F. *ILAR J.* 46(3):258-68. Review (2005). Some applications include immunolocalization, immunoblotting, immunoprecipitation, RIA and ELISA assays, enzyme-linked immunospot assay ("ELISPOT"), proteomics/antibody microarray technology, x-ray crystallography, affinity purification/enrichment, fluorescence-activated cell sorting ("FACS") analysis, expression library screening, immunofluorescence, immunohistochemistry, immunoimaging, and magnetic-activated cell sorting ("MACS"), although this list is by no means exhaustive, and other applications that make practical use of antibodies are recognized by those skilled in the art.

Both monoclonal and polyclonal antibodies (monoclonal antibodies being preferred) have also proven useful as catalytic agents capable of mediating the catalysis of specific synthetic organic reactions. See Xu Y, Yamamoto N, Janda K D. *Bioorg Med Chem* 12:5247-5268 (2004).

Antibodies can also be used to modulate cellular activity in the context of cell culture, live animals, or human patients. Antibodies can neutralize/disrupt or activate/stimulate normal cellular signaling by binding their corresponding antigen. In so doing, the antibody may mimic ligand binding and activate a receptor, or block ligand binding by evincing anti-receptor activity. Alternatively, the antibody may imitate the mechanism by which many receptors are naturally activated by their ligands, through cross-linking of receptors. For example, incubation of B cells with anti-IgM or T cells with anti-CD3, anti-T cell receptor, or anti-Thy-1 is sufficient to mediate cross-linking of the respective cells surface antigens and stimulate an intracellular signaling cascade, which results in cell growth. See Koike T, Yamagishi H, Hatanaka Y, Fukushima A, Chang J, Xia Y, Fields M, Chandler P, Iwashima M. *Biochem Mol Biol* 278:15685-15692 (2003). It may be recognized from these examples that given an antibody to a known antigen, antibodies can be used to discern the role of the antigen in cellular function Antibodies have also demonstrated exceptional promise as drugs and therapeutic agents. After vaccines, antibodies presently constitute the second largest class of drugs and represent the most rapidly growing class of human therapeutics. Carter P J. *Nat Rev Immunol.* 6(5):343-57 (2006). A widely known example of a therapeutic antibody is infliximab, which is used to neutralize tumor necrosis factor (TNF1)-α in patients, which makes it potentially valuable in treating Crohn's disease. See Kirman I, Whelanand R L, Nielsen O H. *Eur J Gastroentero Hepat* 16:639-641 (2004).

Antibody-drug conjugates (ADCs) are monoclonal antibodies (mAbs) linked to active molecules, such as drugs, enzymes, or radioisotopes. By employing a rapidly internalizing mAb, one is able to deliver the drug inside target cells. The environment inside the cell cleaves the linker, which releases the drug and allows it to have the desired effect. An example of an antibody-drug conjugate is an antibody linked to a cytotoxic molecule, which kills target cells that possess the components necessary to cleave the molecule-antibody linker. See, e.g., Wu A M & Senter P D. *Nat. Biotechnol.* 23(9):1137-46 (2005).

Other uses for antibodies in the research, diagnostic, and therapeutic contexts are widely recognized among those skilled in the art, and additional applications continue to be developed. However, while antibodies can target water-soluble regions of antigens, the active domains of many potential targets lie within the hydrophobic biological membrane, into which antibodies cannot penetrate.

Some types of integral membrane proteins include, inter cilia, integrins, cadherins, selectins, NCAM, insulin receptors, and some varieties of cell adhesion and receptor proteins. More generally, membrane proteins may comprise a single transmembrane helix per chain, and in other cases, the membrane protein may comprise a homo- or heterooligomeric protein, each chain thereof having one or more transmembrane helix. The transmembrane region of membrane proteins, which are known to function as any of channels, receptors, enzymes, enablers of cell recognition and/or adhesion, anchors, or energy transducers, commonly possess sections that adopt an alpha-helical configuration. This is because polar CONH groups (peptide bonds) of the polypeptide backbone of transmembrane segments must participate in hydrogen bonds (H-bonds) in order to lower the cost of transferring them into the hydrocarbon interior, and such H-bonding is most easily accomplished with alpha-helices by which all peptide bonds are H-bonded internally. Thus, although the roles of different types of membrane proteins can vary widely, the alpha helix configuration is commonly observed in the transmembrane region.

At present, although methods for designing antibodies for targeting hydrophilic antigens are well developed, there are no corresponding methods for the design of molecules that can be directed against non-water-soluble targets, including the transmembrane region of integral membrane proteins.

SUMMARY OF THE INVENTION

The present invention relates to polypeptides that bind to the helical transmembrane region of membrane proteins. Also disclosed are methods for the design of these polypeptides. Also provided are methods for the use of such polypeptides in various applications, as well as products made through the practice of the instant methods.

BRIEF DESCRIPTION OF THE DRAWINGS

The summary, as well as the following detailed description, is further understood when read in conjunction with the appended figures. For the purpose of illustrating the invention, there are shown in the figures exemplary embodiments of the invention; however, the invention is not limited to the specific methods, compositions, and devices disclosed. In addition, the figures are not necessarily drawn to scale.

FIG. 8 displays results of analytical ultracentrifugation (AUC) experiments.

FIG. 12 demonstrates that the anti-$\alpha_{IIb}$ polypeptide induces fibrinogen binding to CHO cells expressing $\alpha_{IIb}\beta_3$.

DESCRIPTION OF ILLUSTRATIVE EMBODIMENTS

Figure 1:
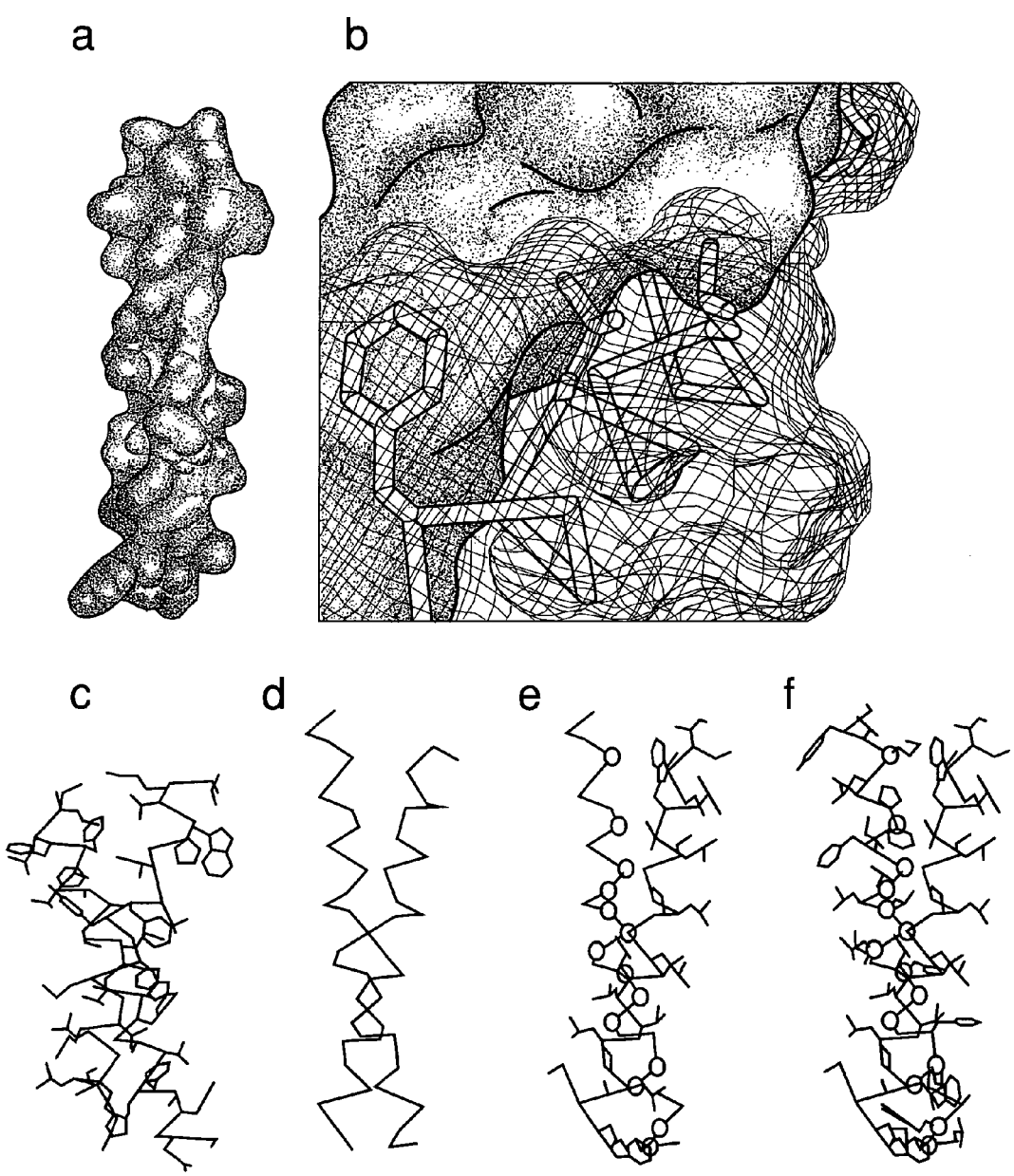
FIG. 1 provides a stepwise representation of the design of the anti-$\alpha_{IIb}$ polypeptide.

The present invention may be understood more readily by reference to the following detailed description taken in connection with the accompanying figures and examples, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention.

Provided are polypeptides that bind to the helical transmembrane region of one or more predetermined membrane proteins. Prior to the instant disclosure, polypeptides with the ability specifically to bind the hydrophobic helical transmembrane (TM) region of a specific membrane protein had not been developed. The invention disclosed herein also represents the first general methods for the design of polypeptides that bind to the TM region of a natural membrane protein. These methods provide ways to produce antibody-like reagents that target a variety of membrane proteins.

The provided polypeptides are believed to target TM helices in a sequence-specific manner. Although antibodies are of tremendous importance in research, medicine, and diagnostics, they target only the water-soluble regions of proteins. A corresponding method for targeting transmembrane helices, such as the method presented herein, has applications as wide-ranging as those involving antibodies themselves. Because of the extensive variety of useful applications that are implicated by the availability of proteins that bind to transmembrane regions, also provided are methods and systems for the use of helical polypeptides in various applications, as well as products made through the practice of the instant methods.

Freeman-Cook et al. have developed a method to identify membrane protein-binding ligand using a genetic method. See Freeman-Cook L L et al. *J Mol. Biol.* 338(5):907-20 (2004). To determine whether it is possible to select novel biologically active transmembrane proteins that can activate growth factor receptors, they constructed and identified small proteins with random hydrophobic transmembrane domains that can bind and activate the PDGF beta receptor. A consensus sequence distinct from the wild-type E5 sequence was identified that restored transforming activity to a non-transforming poly-leucine transmembrane sequence. However, this study did not make available polypeptides that bind to the helical region of a desired transmembrane protein, or supply a generalized methodology for the production thereof.

The present disclosure provides polypeptides which bind to a membrane protein. Specifically, the polypeptides bind to the helical transmembrane region of a particular, predetermined membrane protein or proteins, and upon such binding, the polypeptides may function to modulate the activity of such membrane protein(s). The disclosed polypeptides are substantially complementary (e.g., structurally complementary, chemically complementary, or both) to template polypeptides, which themselves have backbones with a sequence that is, at least in major proportion, the sequence of a portion of the helical transmembrane region of the membrane protein(s) to which the polypeptides bind. At least some of the amino acid positions of the template helix are threaded with different side chains in order to improve the similarity of the template helix to the portion of the helical region of the transmembrane protein to which the inventive polypeptide binds.

The structure of the template polypeptide backbone is preferably derived from a table of helical portions of transmembrane proteins. There exist growing databases of membrane protein structures, and the template polypeptide backbone may be selected from backbone structures provided by such databases, rather than by relying on idealized helical dimers. Membrane protein structure databases are known to those skilled in the art and can be readily accessed. See, e.g., http://blanco.biomol.uci.edu/mptopo/ ("MPtopo" membrane protein topology database); http://pdbtm.enzim.hu/ ("Protein Data Bank of Transmembrane Proteins").

The sequence of the polypeptide that binds to the membrane protein, including the sidechains thereon, may be derived from the template polypeptide through employment of a repacking algorithm. Side-chain repacking algorithms, which are well known in the art, search for combinations of amino acid side chains capable of packing together in efficient, low-energy combinations. Thus, side chains may be also selected in order to improve the helix-helix interaction between the polypeptide and the template polypeptide and therefore the helical transmembrane region of the membrane protein. In one embodiment, the computational design algorithm may be a Monte Carlo repacking algorithm. In the instant invention, Monte Carlo repacking algorithm considers different combinations of sidechains in low energy rotamers and a simplified energy function based on a linearly dampened Leonard Jones van der Waals potential and a membrane depth-dependent knowledge-based potential. See Ulmschneider M B et al., *Proteins: Struct. Funct. Bioinformat.* 59:262-65 (2005). In this algorithm, the knowledge-based potential functions to assure that appropriate residues are selected to interact with the interfacial and fatty acyl region of the bilayer. Other repacking algorithms may be selected according to the user's particular needs.

The polypeptides of the instant invention may also further comprise at least one water solubility enhancing function. Solubility enhancing functions may be bonded to at least one of the carbon (C) and nitrogen (N) termini of the polypeptide. Solubility enhancing functions (which may also be referred to as "solubility-assisting groups") are used to increase the water-solubility and incorporation of the nonpolar polypeptide into membranes. See Melnyk R A et al., *Biopolymers* 71:675-685 (2003). A solubility-assisting group may comprise polar amino acid residues, such as Lys, His, or Asp, or other suitable polar molecules such as polyethylene glycol (PEG), PEG-containing amino acids, or any combination thereof. Any molecule that functions as a solubility assisting group as described herein is contemplated as being within the scope of the present invention.

There are also provided polypeptides having the amino acid sequences XXX MXX XXF IGX XLG (SEQ ID NO:1) or AYV MLL PFF IGL LLG LIF GGA FWG PAR HL (SEQ ID NO:2). These amino acid sequences correspond to polypeptides that bind to the $\alpha_{IIb}$-TM helix, and may be prepared as disclosed infra. See Example 1. Also provided are nucleic acids encoding the anti-$\alpha_{IIb}$ polypeptide, the nucleic acids having the nucleotide sequence GCGTATGTGATGCT-GCTGCCGTTTTTCATTGGCCTGCT-TCTGGGCCTGATTTTTGGCGG TGCGTTTTGGGGC-CCGGCGCGCCATCTG (SEQ ID NO:3). Isolated polynucleotides having a nucleotide sequence complementary to the preceding nucleotide sequence is also provided. Additionally, the present invention is directed to transformed cells that are capable of producing a polypeptide that binds to a helical transmembrane region of a membrane protein comprising an isolated polynucleotide as disclosed. The preparation of such transformed cells is readily accomplished by those skilled in the art.

Also provided are polypeptides having the amino acid sequences XXGXXTFXXGYXXGAXXTGXXYWXX-QXXX (SEQ ID NO:4) and KKIFGVLTFLFGYILGALIT-GAVYWFVQLLAKK (SEQ ID NO:5), which correspond to a second set of polypeptides that bind to the $\alpha_{IIb}$-TM helix, and may be prepared as disclosed herein (Example 1); these polypeptides have been named the anti-$\alpha_{IIb}$' polypeptides. Also provided are nucleic acids encoding the anti-$\alpha_{IIb}$' polypeptide, the nucleic acids having the nucleotide sequence ATCTTCGGTGTTCTGACCTTCCTGTTCG-GTTACATCCTGGGTGCTCTGATCACCGGTGCTGTTT ACTGGTTCGTTCAGCTGCTGGCT (SEQ ID NO:6). Isolated polynucleotides having a nucleotide sequence complementary to the preceding nucleotide sequence is also provided. Additionally, the present invention is directed to transformed cells that are capable of producing a polypeptide that binds to a helical transmembrane region of a membrane protein comprising an isolated polynucleotide as disclosed. The preparation of such transformed cells is readily accomplished by those skilled in the art.

Likewise, the instant invention is also directed to polypeptides having the amino acid sequences XXX XIX XSF XXG TXX GXX XMF XX (SEQ ID NO:7) or AYV FIL LSF ILG TLL GFL VMF WA (SEQ ID NO:8). These amino acid sequences correspond to polypeptides that bind to the $\alpha_V$-TM helix, and may be prepared as disclosed herein. Also provided are nucleic acids encoding the anti-$\alpha_V$ polypeptide, the nucleic acids having the nucleotide sequence GCT-TACGTTTTCATCCTGCTGTCTTTCATC-CTGGGTACCCTGCTGGGTTTCCTGGTTATGTTCT GGGCT (SEQ ID NO:9). Isolated polynucleotides having a nucleotide sequence complementary to the preceding nucleotide sequence is also provided. Additionally, the present invention is directed to transformed cells that are capable of producing a polypeptide that binds to a helical transmembrane region of a membrane protein comprising an isolated polynucleotide as disclosed. The preparation of such transformed cells is readily accomplished by those skilled in the art.

Also provided are polypeptides comprising d-amino acids having the amino acid sequence XXWFXXFXXIFXG-FXXGXXTXXXQX (SEQ ID NO:10). Also disclosed are polypeptides comprising d-amino acids having the amino acid sequence RAWFALFLLIFLGFLLGVATLLVQY (SEQ ID NO:11). These amino acid sequences correspond to d-polypeptides that bind to the $\alpha_{IIb}$-TM helix, and may be prepared as disclosed herein. The amino-acids of the present polypeptides may include 10% or more, 25% or more, 50% or more, 70% or more, or 90% or more d-amino acids. In some instances, these polypeptides consist entirely of d-amino acids.

Other characteristics of the inventive polypeptides may be understood by reference to the provided methods for preparing polypeptides that bind to helical transmembrane regions of membrane proteins. These methods comprise identifying a site of interest on a helical transmembrane region of the membrane protein; based on said site of interest, selecting a starting backbone conformation, thereby obtaining a template helical pair comprising a first helix and a second helix, wherein said first helix and said second helix interact via said site of interest; threading an amino acid sequence corresponding to the helical transmembrane region, including the site of interest, onto the first helix; and, selecting a second amino acid sequence for said second helix using a repacking algorithm. The disclosed methods may further comprise substituting for the second helix a polypeptide comprising at least one d-amino acid, wherein the polypeptide and the first helix interact through said site of interest.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more compounds and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. All ranges are inclusive. Similarly, when values are expressed as approximations, by use of the antecedent "about," it will be understood that the particular value forms another embodiment. All ranges are inclusive and combinable.

Polypeptides produced according to the disclosed methods are capable of binding a helical portion of a membrane protein's transmembrane region. The membrane protein may comprise a single transmembrane helix per chain. In other cases, the membrane protein may comprise a homo- or heterooligomeric protein, each chain thereof having one or more transmembrane helices. The membrane protein may also comprise an integrin, or a heteromeric (e.g., αβ heterodimeric) membrane protein; in other instances, the membrane protein is not a heteromeric protein and comprises a single unit, and not multiple subunits. In some of the examples provided herein, the membrane protein comprises the $\alpha_{IIb}\beta_3$ integrin; in others, the membrane protein comprises the $\alpha_V\beta_3$ integrin. All membrane proteins having at least one helical transmembrane region are contemplated as being within the scope of the present invention.

As used herein, the "site of interest" is a motif on the helix sequence most likely to be involved in activity that is important to the relevant activity or functionality of the transmembrane protein. For example, the site may comprise the protein surface having a high propensity to engage in transmembrane helix-helix interactions. The site of interest may be identified in a number of ways known to those skilled in the art. One available technique for defining the site of interest is site-directed mutagenesis. Site-directed mutagenesis is used to replace nucleotides in a nucleotide sequence that codes for a protein of interest in order to determine the result of disrupting the native sequence on the protein's functionality. See Lemmon M A et al., *Biochem.* 31:12719-12725 (1992). Lemmon et al. used a mutational analysis to determine the sites of helix-helix interface on the transmembrane α helix of glycophorin A (GpA), a human red blood cell transmembrane protein. Another means of determining the identity of the site of interest on a protein is by examining phylogenetically related sequences: a survey of homologous proteins (which are usually phylogenetically related) are used to identify conserved amino acids/sequences, which are in turn more likely to be an essential part to the protein construct. An additional technique can comprise comparing the transmembrane amino acid sequence with known "hot spots" (e.g., GXXXG (SEQ ID NO:12) or small-XXX-small, in which Gly or other small residues spaced four residues apart mediate a close approach of transmembrane residues; see, e.g., Lemmon M A et al., *Biochem.* 31:12719-12725 (1992)), and focusing the search for the site of interest to parts of the transmembrane protein to segments that correspond to such spots. The GXXXG (SEQ ID NO:12) motif, for example is known to occur frequently at the helix-helix interfaces of membrane proteins. See Senes A, et al., *J. Mol. Biol.* 296(3):921-936 (2000). A subsequent study found additional common features in helix-helix interfaces, including networks of apparent Cα-H—O bonds; abundant interfacial Gly, Ser and Thr residues; and, short interhelical axial distances. Senes A et al., *Proc. Nat'l Acad. Sci.* 98(16):9056-9061 (2001). Yet another means for determining the identity of the site of interest is examining propensity profiles. For example, a recent study elucidated recurring helix-helix interaction structural motifs in membrane proteins, and then derived position-specific sequence propensities from the most frequently observed motifs. See Walters R F S & DeGrado W F, *Proc. Nat'l Acad. Sci* (in press).

When the first helix and the second helix of the template helical pair are said to "interact" via the site of interest, or when the polypeptide comprising at least one d-amino acid is said to "interact" with the first helix through site of interest, such interaction may occur via one or more of van der Waals forces, charge, H-bonding, hydrophobic relationship, aromatic relationship, or other mechanism or combination of mechanisms.

It is energetically advantageous for membrane proteins to assume an alpha-helical conformation within the transmembrane region. Thus, many groups of membrane proteins, including ion channels, toxins, antibiotics, and receptors, have alpha-helical secondary structure Dieckmann G R & DeGrado W F. *Cur Op in Struct Biol.* 1997. 7:486-494. In fact, alpha-helices are believed to be the most common motif in membrane proteins. Cohen C & Parry D A D. *Proteins: Struct, Funct, and Gen.* 1990. 7:1-15. Accordingly, polypeptides produced according the instant methods for the manufacture of a polypeptide that binds to a helical transmembrane region of a membrane protein are useful with regard to a broad range of membrane proteins.

After identifying a site of interest, the next step is to select a set of structures to use as potential templates for the design of a polypeptide sequence. The step of determining a starting backbone conformation in order to obtain a template helical pair that comprises first and second helices is preferably accomplished by reference to the growing database of membrane protein structures, rather than by relying on idealized helical dimers. Membrane protein structure databases are known to those skilled in the art and can be accessed with relative ease. See, e.g., http://blanco.biomol.uci.edu/mptopo/ ("MPtopo" membrane protein topology database); http://pdbtm.enzim.hu/ ("Protein Data Bank of Transmembrane Proteins"). Reference to an existing database of membrane protein structures and selection of a helical pair that possesses the known structural preferences based on the site of interest on the target helix (the helical transmembrane region of the relevant membrane protein) will yield the desired starting backbone conformation. For example, if a small-$X_3$-small or $GX_3G$ (SEQ ID NO:12) motif of a transmembrane helix (which typically binds its partner in a tight interaction, forming parallel pairs with a signature interhelical distance of 6.5 to 8.0 Å and a right-handed crossing angle of about 40°; see Bowie J U. *J. Mol. Biol.* 272(5):780-89 (1997); Curran A R & Engelman D M. *Curr. Opin. Struct. Biol.* 13(4):412-17 (2003)) is selected as a site of interest or a portion thereof, a database of crystallographically-determined transmembrane helical pairs may be searched for helices having those structural features for use as the template for further elaboration. See Gimpelev M et al. *Biophys. J.* 87(6):4075-86 (2004); Jordan P et al. *Nature.* 411(6840):909-17 (2001). In one embodiment, a list of TM helix-helix dimers that adopt the structural motif of closely approaching helices and a right-handed crossing angle in the crystal structures of polytopic membrane proteins was extracted (see also Walters R S & DeGrado W F. *Proc. Natl. Acad. Sci.* 103 (in press) (2006)) and consulted; the helical pairs that were considered are listed in Table 2, infra. In that list, most of the helical pairs were generally not homodimers, but rather heterodimers.

Suitable candidates for the starting backbone conformation are selected from the table of prospective helical pairs. In one embodiment, only pairs featuring the site of interest on both members of the helical pair may be considered to be good candidates; this was the case during the preparation of the anti-$\alpha_{IIb}$ polypeptide, where both members of the selected helical pair had the $GX_3G$ (SEQ ID NO:12) motif. See Example 1. However, a suitable helical pair for use as a template may be derived by considering all pairs that result from the initial selection process (i.e., that which utilizes the criterion comprising the site of interest), as was the case during the preparation of the anti-$\alpha_V$ polypeptide. See Example 2. The helical pairs selected from this procedure are referred to as the template pairs, and the individual helices within the pairs are referred to as template helices. Ideally, the helices in the template pair should be long enough to allow threading of the sequence of the target (the sequence substantially corresponding to the sequence of the target helical region of the relevant transmembrane protein) for example, $\alpha_V$-TM or $\alpha_{IIb}$-TM) onto one or both of the two template helices. Furthermore, the site of interest (for example, the small-$X_3$-small motif) should ideally lie at the appropriate depth in the membrane, to allow insertion of the entire target TM helix.

The selection of a starting conformation supplies the template upon which appropriate amino acid sidechains may then be built; the step of threading an amino acid sequence corresponding to the target helix (including the site of interest) onto the first helix may then be performed. See Kortemme T & Baker D, *Curr. Opin. Chem. Biol.* 8(1):91-97 (2004); Shifman J M & Mayo S L, *Proc. Natl. Acad. Sci. U.S.A.* 100(23): 13274-13279 (2003); Reina J et al., *Nat. Struct. Biol.* 9:621-27 (2002); Ogihara N L et al., *Proc. Natl. Acad. Sci. U.S.A.* 98(4):1404-9 (2001); Desjarlais J R & Handel T M, *Protein Sci.* 4(10):2006-18 (1995). Prior to threading the amino acid sequence corresponding to the helical transmembrane region, including the site of interest, onto the first helix, the first or second or both template helices may optionally be extended to span the width of a cell membrane (typically approximately 30 Å) (see FIG. 1, step d). The sequence corresponding to the target helix on the transmembrane protein may be determined according to procedures known to those skilled in the art, including, but not limited to, automated protein sequencing, mass spectroscopy, Edman degradation, N-terminal sequencing, genome sequencing, and other procedures known in the art. The procedure for doing so may involve determining the nucleic acid sequence of part or all of the transmembrane protein (including part or all of the constituent transmembrane helix), followed by identifying the site of interest using techniques such as those described, supra, along with the corresponding sequence thereof.

The threading of the amino acid sequence of the target helix preferably involves ensuring that the site of interest is appropriately positioned or "phased" to lie along the point of closest approach of the two template helices. For example, where the site of interest comprises the small-$X_3$-small motif, this can be accomplished by matching the small-$X_3$-small motif of target sequence to the small-$X_3$-small motif of the template helix. Alternatively, the closest carbon a to the opposite helix is considered to be one of the small positions and the closer of i+4 and i−4 is used as the location in the second small residue.

In the instant invention, helices are oriented with the bundle axis parallel to the membrane normal (the z-axis), so that the center of the hydrophobic stretch of the target helix has a z coordinate of zero. Thus, the template helices may be oriented as desired so that the center of the hydrophobic stretch of the target helix assumes a desired position. This allows the use of the knowledge-based potential function which assures that appropriate residues are selected to interact with the interfacial and fatty acyl region of the bilayer.

Subsequent to the step of threading an amino acid sequence substantially corresponding to the helical transmembrane region of the membrane protein (target helix) onto the first helix, a sequence for the second helix is selected using a computational design algorithm, such as a side chain repacking algorithm. Thus, all positions are preferably computationally defined. In some embodiments, however, where Pro residues are encountered in the native sequence of the template helix, such Pro residues are retained, since they may be important for defining the main chain conformation of the template for the membrane protein-binding polypeptide.

In some embodiments, rather than selecting a sequence using a computational design algorithm for the second helix, a polypeptide comprising at least one d-amino acid is substituted for the second helix, and a sequence is selected for the polypeptide using a computational design algorithm. The polypeptide comprising at least one d-amino acid may be referred to as a "d-peptide". The use of an idealized helical d-peptide in place of the second helix can render the membrane protein-binding polypeptide product more resistant to metabolic degradation (e.g., proteolysis), to which L-amino acid polypeptides are more naturally vulnerable. See Fischer P M, *Curr Protein Pept Sci.* 2003 October; 4(5):339-56. Review. Other advantages associated with the use of d-peptides for therapeutic applications will be apprehended by those skilled in the art. See, e.g., Fischer P M (2003). The polypeptide comprising at least one d-amino acid can comprise a single d-amino acid, multiple d-amino acids, a majority d-amino acids, or may be made entirely from d-amino acids.

When a d-peptide is substituted for the second helix, the d-peptide may possess the opposite symmetry as the second helix, thereby forming a "left-handed" alpha helix, as compared with the "right-handed" orientation of the second helix. The d-peptide may be spatially oriented in relation to the first helix such that the d-peptide and the first helix interact at the site of interest (just as the second helix and the first helix interacted at the site of interest). For example, where the site of interest comprises a GXXXG (SEQ ID NO:12) motif, the idealized d-helix may be oriented onto the same helical template (i.e., the second helix) as would be used for the traditional design methodology, such that the glycine carbon alphas in the d-peptide are spatially oriented in the same manner as the glycine carbon alphas in the second helix. Following the substitution of the second helix for the d-peptide, the d-peptide is repacked in the same manner as the original second helix would be repacked in accordance with the traditional methodology, described supra.

In the present application, all steps pertaining to the selection of an amino acid sequence for the "second helix" are applicable to the embodiments of the instant invention in which a polypeptide comprising at least one d-amino acid is substituted for the second helix.

In some embodiments, the sequences for the second helix are computed in two distinct sub-steps. First, the residues that are proximal to the target helix are determined. For example, this was done by examination of the structure for positions that appeared to be close to the second helix for the anti-$\alpha_{IIb}$ polypeptides, and computationally for the anti-$\alpha_V$ polypeptide. The second step comprises further restricting the polypeptide helix design (i.e., the anti-TM helix design) by converting the entire helix to glycine and testing each identity at each position to see if there is a possible rotamer of that identity that would not clash with the TM helix backbone. In this process the lowest energy ensemble of rotamers for the helical pair may determined using a graph-theory based sidechain conformation predicting algorithm, such as SCWRL3. See Canutescu A A et al. *Protein Sci.* 12 2001-2014 (2003). Other methods for determining the lowest energy ensemble of rotamers may be used; nonlimiting examples of other methods include Monte Carlo and dead end elimination. With respect to the preparation of the anti-$\alpha_V$ polypeptide (Example 2), only identities that had at least one possible rotamer that did not clash with the TM helix backbone were considered in the repacking step. Once the set of proximal positions was designated and their possible identities are defined, the sequence of the membrane protein-binding polypeptide may be determined.

Side-chain repacking algorithms, which are well known in the art, search for combinations of amino acid side chains capable of packing together in efficient, low-energy combinations. An exemplary repacking algorithm considers different combinations of sidechains in low energy rotamers and a simplified energy function based on a linearly dampened Leonard Jones van der Waals potential and a membrane depth-dependent knowledge-based potential. See Ulmschneider M B et al., *Proteins: Struct. Funct. Bioinformat.* 59:262-65 (2005). In this algorithm, the knowledge-based potential functions to assure that appropriate residues are selected to interact with the interfacial and fatty acyl region of the bilayer. Other repacking algorithms may be selected. A variety of different repacking programs and methods for searching sequence/rotamer space were evaluated, each providing essentially the same result so long as constraints or a depth-dependent potential is used to force hydrophobic residues at the appropriate positions of the membrane.

In one example, sequence and rotamer space for the helix and rotamer space for the $\alpha_{IIb}$ or $\alpha_V$ sequence were explored using 10,000 iterations of metropolis Monte Carlo simulated annealing using an exponential cooling schedule. For each step of the Monte Carlo procedure one of the proximal residues on the helix was mutated. This mutation was then followed by rotamer optimization for the entire ensemble of residues in the helical pair. The new energy of the ensemble was then calculated, and the mutation was either accepted or rejected based on a simulated annealing criterion. Only rotamers with high probabilities of occurrence within helical backbones were considered. Rotamers were optimized using Goldstein D E E (Goldstein R F. *Biophys. J.* 66, 1335-40 (1994)) and then exhaustive enumeration. Residues not previously selected for variation were fixed as Val, to simplify rotamer selection.

The algorithm may be used to determine residues both at the proximal/helix-helix interface region, and at the membrane exposed region(s). In other instances, it is simpler (yet still effective) to determine only the residues at the helix-helix interface, while the membrane-exposed residues of the helix are randomly selected from common hydrophobic residues such as leucine, alanine, isoleucine, phenylalanine, valine, and the like. For example, a 60% percent probability may be assigned to Leu and a 10% probability to each of Ala, Ile, Phe, and Val.

In some embodiments, the step of selecting a second amino acid sequence includes appending at least one water solubility enhancing function to the N-terminus, the C-terminus, or both termini, of the second amino acid sequence. The solubility enhancing function is included in order to increase the water-solubility and incorporation of the nonpolar polypeptide into membranes. See Melnyk R A et al., *Biopolymers* 71:675-685 (2003). A solubility enhancing function may comprise polar amino acid residues, such as Lys, His, or Asp, or other suitable polar molecules such as polyethylene glycol (PEG), PEG-containing amino acids, or any combination thereof. Any molecule that functions as a solubility enhancing function as described herein is contemplated as being within the scope of the present invention.

The method for producing a membrane protein-binding polypeptide may comprise obtaining multiple template helical pairs and performing the threading and repacking steps with respect to each template helical pair. Thus, the inventive method may include the manipulation of a single template helical pair or of multiple candidate helical pairs. Optionally, any template helical pair that is selected can be characterized as having helices long enough to span the cellular phospholipid membrane. This criterion may be met wherever each helix is at least 20 residues long. In other instances, the selected template helices are not long enough to span a phospholipid membrane, and in such cases, the first or second or both template helices may optionally be extended to span the width of a cell membrane (typically approximately 30 Å), as previously described (see also FIG. 1, step d).

Furthermore, especially where multiple template helical pairs are selected, the disclosed methods may comprise additional steps. Where multiple candidate helical pairs are selected, the method may further comprise determining which of the template helical pairs are capable of reaching a low energy solution. Examination of the template helical pairs may reveal, for example, that steric clashes exist that would decrease the binding efficiency between the membrane protein-binding polypeptide and the target helix. Using those template helical pairs that were determined to be capable of reaching a low energy solution, the method may further comprise threading an amino acid sequence corresponding to the site of interest onto the first helix of each of the helical pairs, minimizing the template helical pairs, and, given that the template helical pairs will need to possess side chains, selecting amino acid sequences for the side chains of the template helical pairs using a computational design algorithm. As used herein, "minimizing" means making very small changes in positions of atoms that would cause the ensemble to be at a lower energy. The computational design algorithm employed during the initial episode of selecting amino acid sequences may also be used in the subsequent amino acid repacking steps described herein.

There may also be a subsequent, additional episode of minimizing the template helical pairs, which may be followed by the selection of a subset of the helical pairs based on geometric qualifications. Geometric qualifications may include such characteristics as, inter alia, uniformity of packing and the absence of large voids. Subsequently, using the helical pairs included within the selected subset, there may also be a step comprising threading an amino acid sequence corresponding to the site of interest onto the first helix of each helical pair, and selecting a second amino acid sequence for the second helix using a repacking algorithm.

The finished polypeptide product may be prepared according to procedures that are readily recognized by those skilled in the art. Thus, liquid or solid phase peptide synthesis may be employed to prepare the membrane protein-binding polypeptide.

Also provided herein are methods for assessing the suitability of a polypeptide according to the present invention or a polypeptide produced according to the disclosed methods to be used as a transmembrane protein-binding reagent. The described methods are useful for confirming that the polypeptide inserts into a cell membrane, associates closely with the target helical transmembrane region of a membrane protein, and may be contacted with cells without inducing cell lysis. Fluorescence Resonance Energy Transfer (FRET) is known in the art and has numerous applications molecular biology, including for detecting the interaction between two fluorescently-labeled molecules. To monitor the formation of a complex between two molecules, one molecule may be labeled with a donor fluorophore and the other molecule with an acceptor fluorophore. When the donor and acceptor fluorophores are in close proximity (1-10 nm), the acceptor emission is predominantly observed because of the intermolecular fluorescence resonance energy transfer from the donor to the acceptor. In contrast, the donor fluorophore emission is predominantly detected when the donor and acceptor fluorophores, and therefore the molecules to which they are appended, are dissociated. See, e.g., Lakowicz J R, "*Principles of Fluorescence Spectroscopy*" (Plenum Publ. Corp. 2d ed. Jul. 1, 1999). Likewise, FRET can be used to measure the association between a membrane protein-binding polypeptide and a membrane protein. Provided herein is a method of measuring the association between a polypeptide produced according to the disclosed methods and the helical transmembrane region of a membrane protein, comprising titrating the membrane protein-binding polypeptide with the membrane protein or a portion thereof, wherein the polypeptide is labeled with one of a donor fluorophore or an acceptor fluorophore and said membrane protein or a portion thereof is labeled with the other of said donor fluorophore or acceptor fluorophore, and, measuring the degree of quenching of fluorescent emission from said donor fluorophore or the degree of increase of fluorescent emission from said acceptor fluorophore, or both. Such measurement provides an indirect but accurate measure of the spatial proximity between the prepared membrane protein-binding polypeptide and the membrane protein to which it is intended to bind.

The membrane protein-binding polypeptide's ability to insert into the cellular phospholipid bilayer is likely important to its utility as a membrane protein-binding molecule. Tryptophan fluoresence intensity, e.g., emission maxima, in the subject peptide can serve as an indicator of phospholipid bilayer insertion. General tryptophan emission studies are well known in the art. See, e.g., Ladokhin A S et al., *Anal. Biochem.* 285:235-245 (2000). Provided herein are methods for assessing the ability of a polypeptide according to the instant disclosure or of a polypeptide produced according to the disclosed methods to insert into a phospholipid bilayer membrane comprising measuring the emission maximum of tryptophan (Trp) residues in the polypeptide in order to obtain a first emission value; contacting the polypeptide with structures having a hydrophobic region; after said contacting, measuring the emission maximum of tryptophan residues in the polypeptide to obtain a second emission value; and, comparing the first emission value with the second emission value. A shift toward a shorter wavelength between the first and second emission values will be indicative of the polypeptide's having successfully inserted into the hydrophobic region of the chosen structures. The structures having a hydrophobic region may be liposomes or vesicles, such as unilamellar or multilamellar vesicles, or a different type of structure may be used; choosing a suitable structure for use with the instant methods is within the knowledge of one skilled in the art. Structures having a hydrophobic region may be purchased (for example, from Encapsula NanoSciences, Nashville, Tenn.) or prepared from laboratory reagents (see, e.g., Hope M J et al., *Biochim. Biophys. Acta* 812:55-65 (1985) (preparation of unilamellar phosphatidylcholine vesicles via extrusion process); Mayer L D et al. *Biochim Biophys Acta.* 858(1):161-8 (1986) (production of homogeneously sized unilamellar or plurilamellar vesicles)).

Basic hydrophobic peptides can cause cell lysis, Bechlinger B. *J. Membr. Biol.* 156:197-211 (1997), and low hemolytic potential of a compound is understandably important to its utility as a research, diagnostic, or therapeutic tool in vivo. Provided are methods for assessing the potential of the instant polypeptides or polypeptides produced according to the disclosed methods to cause cell lysis, comprising contacting said polypeptide with a cell sample to produce a test sample; and, determining the extent of cell lysis in the test sample. A high proportional quantity of cell lysate or visibly lysed cells in the test sample is indicative of a peptide's high hemolytic potential and may be suggestive of the particular polypeptide's unsuitability for some applications involving whole-cell protocols.

Because the instant polypeptides and polypeptides produced according to the disclosed methods are capable of binding the helical transmembrane region of a membrane protein in a highly sequence-specific manner, they are tantamount to antibody-like reagents that can be used to target a variety of membrane proteins. Just as antibodies are of tremendous importance in research, medicine, and diagnostics, the instant polypeptides and polypeptides produced according to the instant methods have applications as wide-ranging as antibodies themselves, except whereas antibodies are useful for targeting the water-soluble regions of proteins, the instant polypeptides target hydrophobic regions of proteins.

Thus, because of the extensive variety of useful applications that are implicated by the availability of proteins that bind to transmembrane regions, there are also provided methods and systems for the use of membrane protein-binding polypeptides in various applications, as well as products made through the practice of the instant methods.

Antibodies are frequently used to locate their corresponding antigens in a test sample, an application known as immunolocation or immunohistochemistry. A detection label may be appended to a membrane protein-binding polypeptide, either directly or indirectly (just as antibodies may be labeled directly or through use of a labeled secondary antibody), in order to permit membrane protein-binding polypeptide-mediated localization of the membrane protein to which it binds. Detection labels or tags are well known in the art and may include fluorophores, gold nanoparticles, biotin, alkaline phosphatase, horseradish peroxidase, and the like. Immunohistochemical techniques are also widely understood by those skilled in the art, and parallel techniques are employed in order to localize a target protein in a sample using the membrane protein-binding polypeptide that corresponds to the target.

For example, a method for localizing a target protein in a sample may comprise contacting a membrane protein-binding polypeptide with the sample, and detecting the presence of the polypeptide in the sample, wherein the polypeptide is capable of binding or is specific to the target protein. In such methods, the membrane protein-binding polypeptide may be conjugated to a detection label: the detection label may be directly appended to the membrane protein-binding polypeptide, or an antibody that is specific to the polypeptide may be contacted with the polypeptide and the sample, either where the antibody is directly attached to a detection label, or where a secondary antibody that is itself associated with a detection label is attached to the primary, membrane protein-binding polypeptide-specific antibody. Thus, as used throughout the instant disclosure, the term "conjugated" refers to direct or indirect attachment. Depending on the desired reaction, the conditions necessary for optimal reaction results are easily ascertained by those skilled in the art.

Also as used herein, when used to describe the relationship between a target or membrane protein and a polypeptide according to the present invention or a polypeptide produced according to the disclosed methods, the terms "binds to" and "specific to" mean that the polypeptide is substantially complementary to a template polypeptide; the template polypeptide having a backbone, the sequence of which backbone is at least, in major proportion, the sequence of a portion of the helical transmembrane region of the target or membrane protein; at least some of the amino acid side chains of the template polypeptide being threaded with different side chains in order to improve the similarity of the template polypeptide to the portion of the helical region of the target or membrane protein. The provided definition and the terms "binds to" and "specific to" when used in describing the relationship of a membrane protein-binding polypeptide to a target or membrane protein are therefore used interchangeably throughout the instant disclosure unless otherwise specified.

Like their antibody counterparts when used in RIA- and ELISA-style assays, membrane protein-binding polypeptides may be used for the detection or quantitation of a target protein in a sample. Such methods comprise contacting the sample with a membrane protein-binding polypeptide, wherein the polypeptide is specific to the target protein, and then measuring the presence of the membrane protein-binding polypeptide in the sample. The measurement of the membrane protein-binding polypeptide in the sample may be made directly or indirectly, such as by measuring the fluorescence or optical density of the sample itself to obtain an indirect assessment of whether the membrane protein-binding polypeptide is present and/or in what quantity. Thus, such ELISA-type assays using membrane protein-binding polypeptides may be run in a qualitative or quantitative format. Qualitative results provide a simple positive or negative result for a sample. The cutoff between positive and negative is determined by the analyst and may be statistical: two or three times the standard deviation is often used to distinguish positive and negative samples. In a quantitative variety of the instant method, the optical density, fluorescent units, or other measurable parameter of the sample is measured. The membrane protein-binding polypeptide may be directly attached to a detection label, or the disclosed method may further comprise incubating the sample with an antibody that is specific for the polypeptide, wherein the antibody itself is attached to a detection label. In additional embodiments of the present method, the polypeptide is bound to a solid surface within an incubation environment, the sample is introduced into the incubation environment, and an antibody specific to the target protein is introduced into the incubation environment, wherein the antibody is conjugated to a detection label. This embodiment resembles a "sandwich" assay, which is widely practiced and makes use of antibodies instead of the instant transmembrane helix-binding polypeptides. The reagents and protocols necessary for performing basic detection and quantitation assays are familiar to those skilled in the art, and may be applied to the novel disclosed methods that make use of membrane protein-binding polypeptides.

Antibodies can also be used to modulate cellular activity in the context of cell culture, live animals, or human patients. Because an antibody may have an identified cellular antigen (such as a receptor or other protein) the function of which may not be fully understood, antibodies can assist in the characterization of the antigen's function under native or suitable experimental conditions. Likewise, the instant disclosure enables a method for analyzing the function of a membrane protein comprising contacting the membrane protein with a membrane protein-binding polypeptide that is specific to the membrane protein; and, determining whether any modulation of the membrane protein results subsequent to the contacting step. Typically, the contacting of the polypeptide with the membrane protein, which may be performed in the context of, inter alia, cell or tissue culture, live animals, human patients, or under a variety of experimental conditions readily recognized by those skilled in the art will comprise incubation or inoculation with the membrane protein-binding polypeptide. Determining whether any modulation of the membrane protein has taken place will be a matter of monitoring the cell, tissue, test subject, or experimental conditions (micelles bilayers, bicelles, should we mention those since that what we talk about characterizing the peptides in later) according to recognized techniques and may include the measurement of germane biological processes. Also provided are methods for modulating the function of a transmembrane protein, comprising contacting a membrane containing said transmembrane protein with a membrane protein-binding polypeptide, the polypeptide being substantially complementary to a template polypeptide; the template polypeptide having a backbone, the sequence of which backbone is at least, in major proportion, the sequence of a portion of the helical transmembrane region of the transmembrane protein; at least some of the amino acid side chains of the template polypeptide being threaded with different side chains in order to improve the similarity of the template polypeptide to the portion of the helical region of the transmembrane protein.

The instant polypeptides can also be used to screen substances such as small-molecule drug candidates for the ability to affect the function of a protein comprising at least one helical transmembrane region. Protein microarray technology is used to enable rapid screening of thousands of small-molecule drug candidates to determine their potential to affect specific proteins. MacBeath G & Schreiber S L. *Science.* 289(5485):1673 (2000). When the protein is a membrane protein with a helical transmembrane region to which a corresponding polypeptide binds, the template polypeptide may be used as part of a method for analyzing the ability of various substances to affect the function of such a protein. The methods comprise adhering a template polypeptide to a surface under conditions selected to maintain the function of the template polypeptide; the template polypeptide having a backbone, the sequence of which backbone is at least, in major proportion, the sequence of a portion of the helical transmembrane region of the membrane protein; at least some of the amino acid side chains of the template polypeptide being threaded with different side chains in order to improve the similarity of the template polypeptide to the portion of the helical region of the membrane protein; contacting the test substance (e.g., a drug candidate) with the template polypeptide or a part thereof; and, measuring the function of the template polypeptide. If the function of the template polypeptide is altered by having been contacted with the test substance, then the substance can be earmarked and subjected to further analysis.

Another common biochemical application for antibodies is protein purification. The instant polypeptides can be used for the affinity purification of membrane proteins in a sample, such as cell lysate. The availability of polypeptides that bind specifically to membrane proteins therefore permits the use of a method that employs known affinity purification protocols to isolate membrane proteins from a sample, a new and highly beneficial biochemical tool with regard to proteins that reside in hydrophobic regions of cells. Provided are methods of protein purification comprising passing a composition containing a target protein through a chromatography column, wherein the column contains an immobilized membrane protein-binding polypeptide that is specific to the target protein. Columns for affinity chromatography are widely commercially available, and techniques for preparing such columns for use are known by those skilled in the art. After the sample composition is passed through the chromatography column, the column resin is typically rinsed, and the target protein may be eluted by manipulation of pH or salinity or by other means, collected, and then, if desired, subjected to additional purification processing.

"Western blotting" is a method for detecting protein in a given sample, for example, in tissue homogenate or extract.

Gel electrophoresis is used to separate denatured proteins by mass, and the denatured proteins are then transferred onto a membrane (typically nitrocellulose or PVDF), where they are probed using antibodies specific to the protein. Because of the specificity of a membrane protein-binding polypeptide for the membrane protein to which it corresponds, these polypeptides may be used in like fashion to probe for membrane proteins in a sample. Accordingly, there are provided herein western blot-like methods of protein detection comprising transferring a composition containing a fractionationed target protein to a solid support membrane, said composition having been subjected to conditions suitable to cause denaturation of any proteins contained therein and to electrophoresis; and, contacting the solid support membrane with a solution containing a membrane protein-binding polypeptide, where said polypeptide is specific to the target protein. In the disclosed methods, the target protein will therefore comprise a membrane protein to which the membrane protein-binding polypeptide binds. In preferred embodiments, the polypeptide is conjugated to a detection label. Other methods additionally comprise contacting said membrane with an antibody that is specific to the membrane protein-binding polypeptide, wherein the antibody is conjugated to a detection label; in still other methods, the additional incubation is performed with a primary antibody that is specific to the membrane protein-binding polypeptide, and a second incubation is performed using a secondary antibody that is conjugated to a detection label, wherein the secondary antibody is directed to a species-specific portion of the primary antibody. All variations on the "western-blotting" procedure that are typically practiced by those skilled in the art are contemplated as being within the scope of the provided western blot-like methods.

Another well known technique that may make use of antibodies is flow cytometry, which is used to detect any of a number of different measurable parameters that are suspended in a stream of fluid. See Fouchet P et al., *Biol Cell.* 78(1-2):95-109. *Review* (1993). One measurable parameter includes proteins, and the expression (either positive/negative or degree of expression) of a given protein by cells in a cell sample can be assessed by detecting the fluorescence or optical density associated with such protein by virtue of the binding thereto by an antibody, which may be conjugated to a detection label. Because the membrane protein-binding polypeptide can function in a manner comparable to an antibody to bind a specific membrane protein in a sample, such polypeptides can be used in conjunction with flow cytometry to determine the expression of a membrane protein of interest among cells in a cell sample. Such methods therefore comprise contacting the cell sample with a membrane protein-binding polypeptide, said polypeptide being specific to the membrane protein of interest; and, using flow cytometry to obtain an absorbance or fluorescence profile of the cells in the cell sample, wherein the absorbance or fluorescence profile varies depending on the absence or presence of a detection label in association with said polypeptide. The detection label may be conjugated to the membrane protein-binding polypeptide. Thus, the detection label may be directly attached to the polypeptide, or alternatively, the disclosed method may further comprise contacting the cell sample with a labeled antibody that is specific to the membrane protein-binding polypeptide.

Expression libraries (often comprising cDNA) can be screened using antibodies in order to identify those genes that may express a protein of interest. A cDNA library of genes that express membrane proteins can therefore be screened using a membrane protein-binding polypeptide that is specific to a protein of interest for which the corresponding gene (i.e., the gene that encodes the protein of interest) has not been identified. In this way, genes that are candidates for the expression of the protein of interest may be isolated. Provided herein are methods for screening an expression library in order to isolate candidate genes that express a target protein comprising contacting a membrane protein-binding polypeptide with a protein expressed by a candidate gene of said expression library, wherein said polypeptide is specific to the target protein, and, assessing the affinity of said polypeptide for said protein expressed by the candidate gene. High affinity between the membrane protein-binding polypeptide and the expression product of the candidate gene may indicate that the candidate gene encodes the target protein.

Antibody-drug conjugates (ADCs) are monoclonal antibodies (mAbs) linked to active molecules, such as drugs, enzymes, or radioisotopes. An example of an antibody-drug conjugate is an antibody linked to a cytotoxic molecule, which kills target cells that possess the components necessary to cleave the molecule-antibody linker. See, e.g., Wu A M & Senter P D. *Nat. Biotechnol.* 23(9):1137-46 (2005). The technique has demonstrated promise for cancer treatment, since it can be used to target only those cells that express the pathology. Membrane protein-binding polypeptides can also be linked to a drug conjugate and thereby used to target for beneficial treatment or death those cells that express the membrane protein to which the polypeptide is specific. Provided herein are methods for delivering a drug to a cell expressing a target protein comprising contacting the cell with a membrane protein-binding polypeptide, wherein the polypeptide is specific to the target protein and is conjugated to the drug. Contacting the cell expressing the target protein with the membrane protein-binding polypeptide may include incubation of a cell or tissue with the polypeptide, inoculation of a subject with the polypeptide, or any other suitable technique. The drug may be a cytotoxic agent, such as a radioisotopes, drugs, or other toxic effector molecules, or may be a therapeutic agent.

Antibodies have also demonstrated exceptional promise as drugs and therapeutic agents. After vaccines, antibodies presently constitute the second largest class of drugs and represent the most rapidly growing class of human therapeutics. Carter P J. *Nat Rev Immunol.* 6(5):343-57 (2006). Therefore, antibodies, with their highly specific binding capabilities, are receiving increasing attention for their potential for use in efficacious drug products, and membrane protein-binding polypeptides, because they can target hydrophobic regions of membrane proteins in the manner that antibodies target water-soluble subjects, represent a promising new avenue for drug development. The instant invention accordingly additionally comprises a pharmaceutical composition comprising a polypeptide according to the present invention or a polypeptide prepared according to the disclosed methods. The pharmaceutical composition may further comprise a pharmaceutically acceptable carrier, diluent, or excipient. The applicable carrier, diluent, or excipient may be selected on the basis of the chosen route of administration and standard pharmaceutical practice as described, for example, in *Remington's Pharmaceutical Sciences* (Mack Pub. Co., Easton, Pa., 1985), the disclosure of which is hereby incorporated by reference in its entirety.

Infliximab, a prominent therapeutic antibody, is given as an intravenous infusion. The pharmaceutical compositions of the present invention may be administered orally or parenterally, neat or in combination with conventional pharmaceutical carriers, diluents, or excipients, which may be liquid or solid. Of course, any material used in preparing any dosage unit form is preferably pharmaceutically pure and substantially non-toxic in the amounts employed. In addition, the active compound may be incorporated into sustained-release preparations and formulations. Parenteral administration in this respect typically includes administration by the following routes, among others: intravenous, intramuscular, subcutaneous, intraocular, intrasynovial, transepithelial including transdermal, ophthalmic, sublingual and buccal; topically including (but not limited to) ophthalmic, dermal, ocular, rectal and nasal inhalation via insufflation, aerosol, and rectal systemic. The pharmaceutical forms suitable for injectable use include, for example, sterile aqueous solutions or dispersions and sterile powders for the extemporaneous preparation of sterile injectable solutions or dispersions.

The compositions of the invention may be administered in an effective amount by any of the conventional techniques well-established in the medical field. The compositions may be administered by any means that results in the contact of the active agents with the agents' site or sites of action in the body of a patient. The polypeptides may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients, where medically appropriate.

EXAMPLES

The present invention is further defined in the following Examples. It should be understood that these examples, while indicating preferred embodiments of the invention, are given by way of illustration only, and should not be construed as limiting the appended claims From the above discussion and these examples, one skilled in the art can ascertain the essential characteristics of this invention, and without departing from the spirit and scope thereof, can make various changes and modifications of the invention to adapt it to various usages and conditions.

Additional information regarding the present invention can be found at Yin H & Slusky J S, et al., *Science*. 2007 Mar. 30; 315(5820):1817-22, which is hereby incorporated by reference in its entirety.

Example 1

Preparation of Membrane Protein-Binding Polypeptides

The present example illustrates the utility of the method by designing polypeptides that specifically recognize the transmembrane ("TM") helix of the α-subunit of the platelet integrin $\alpha_{IIb}\beta_3$, or the TM helix of the α-subunit of the platelet integrin $\alpha_V\beta_3$. Thus, one of the designed polypeptides binds to the $\alpha_{IIb}$ transmembrane sequence and strongly activates native $\alpha_{IIb}\beta_3$ in mammalian cells, and another designed polypeptide binds to the $\alpha_V$ TM sequence and likewise activates the corresponding native integrin. These results illustrate the utility of membrane protein-binding design for generating high affinity molecules that bind to and modulate the functions of membrane proteins.

Two membrane protein-binding anti-$\alpha_{IIb}$ polypeptides were designed and experimentally characterized; although both were highly active (see FIG. 4 & FIG. 11), one, designated anti-$\alpha_{IIb}$, displayed better physical properties and solubility and was used in subsequent studies. The other, anti-$\alpha_{IIb}$' was prepared in parallel, and was not included in subsequent studies, but is referred to in subsequent sections of the instant disclosure.

FIG. 1 supplies a depiction of the membrane protein-binding design process, using the example of the anti-$\alpha_{IIb}$ polypeptide. FIG. 1a provides a surface representation of the $\alpha_{IIb}$ TM helix. The structure depicts the surface of the $\alpha_{IIb}$ TM helix with residues believed to be critical for interacting with the $\beta_3$ TM helix (G972, G976, L980, 1981) (light gray). FIG. 1b is a close-up of the predicted tightly packed interface between anti-$\alpha_{IIb}$ and anti-$\alpha_{IIb}$-TM. $\alpha_{IIb}$-TM is represented by a dark gray surface with a light gray "hot spot". The anti-$\alpha_{IIb}$ backbone is depicted in ribbon representation with the sidechains of key positions designated for computational design shown. FIGS. 1c-1f show the design process of the membrane protein-binding polypeptide. In FIG. 1c, the original structure and sequence of the template is provided: photosystem I reaction center ζ subunit (Jordan P et al. *Nature* 411, 909-917 (2001)). In FIG. 1d, the original sequence has been stripped off the template and the helices have been extended to span the full length of a membrane. In FIG. 1e, the sequence of $\alpha_{IIb}$ TM is threaded on the right helix. The fourteen positions selected for repacking have been highlighted with small spheres on the carbon α's on the left helix The final anti-$\alpha_{IIb}$ polypeptide sequence is shown in FIG. 1f on the left helix with the repacked positions in lighter grey with spheres on their carbon as. The anti-$\alpha_V$ polypeptide was synthesized with a very short N-terminal polyethylene glycol fragment (8-amino-3,6-dioaoctanoic acid) rather than two Lys residues to avoid some of the hemolytic activity observed with respect to the anti-$\alpha_{IIb}$ polypeptide.

Computational Design

To design a polypeptide capable of disrupting $\alpha_{IIb}/\beta_3$ TM helix-helix interactions, it was desired first to define the site on the $\alpha_{IIb}$ TM helix that engages $\beta_3$ in the resting state. FIG. 1a illustrates the location of mutations along the $\alpha_{IIb}$ TM helix known to activate the integrin (Partridge, A W et al, *J. Biol. Chem.* 280:7294-7300 (2005); Luo B H et al., *Plos Biology* 2:776-786 (2004); Li W et al. *Proc. Natl. Acad. Sci. U.S.A.* 102:1424-1429 (2005)), which, while not wishing to be bound by any particular theory of operation, is likely achieved by disrupting $\alpha_{IIb}/\beta_3$ TM helix-helix interactions. The identified surface has a high propensity to engage in TM helix-helix interactions as assessed by a statistical scale based on the probability of burial versus membrane exposure for individual amino acids. See Adamian L et al., *Proteins: Struct. Funct. Bioinformat.* 59, 496-509 (2005). It is noteworthy that this surface contains a GX$_3$G (SEQ ID NO:12) motif known to occur frequently in the helix-helix interfaces of membrane proteins. Senes A et al., *J. Mol. Biol.* 296, 921-936 (2000).

One study compared all known transmembrane helical dimers and found that there were only a small number of geometric conformations that transmembrane helical dimers assume. Walters R F S and DeGrado W F, *Helix Packing Motifs in Membrane Proteins* (in press at *PNAS*). The study further found that some of these preferred geometries are associated with sequence motifs. Id. Because $\alpha_{IIb}$ contains a sequence motif (i.e., the small-X$_3$-small motif) that is characteristic of one of the classes of dimer geometries, structures that were part of the class of dimer geometries that is associated with that sequence motif were used.

A total of five potential templates were examined. Both helices were extended to span the width of a membrane (approximately 30 Å). With regard to anti-$\alpha_{IIb}$', the sequence of the $\alpha_{IIb}$ TM was threaded onto the first helix (positions L43-L65). For anti-$\alpha_{IIb}$, the sequence of the $\alpha_{IIb}$ TM was threaded onto the second helix (positions L114-L140) of the helical template. Alignment for the threading was determined by matching the locations of the glycines in the $GX_3G$ (SEQ ID NO:12) motif of $\alpha_{IIb}$ to the glycines in the $GX_3G$ (SEQ ID NO:12) motif of the photosystem structure as in FIG. 1. The backbones of the complex were then minimized to remove clashes with the threaded $\alpha_{IIb}$ TM sequence. On the membrane protein-binding helix, several residues were selected for repacking based on their proximity to the $\alpha_{IIb}$-threaded helix, 12 for anti-$\alpha_{IIb}$', and 14 for anti-$\alpha_{IIb}$. The backbone template chosen for the design of the two anti-$\alpha_{IIb}$ polypeptides was a helix pair derived from the photosystem I reaction center ξ subunit (1JB0, residues L43-L65 and L114-L140). This particular template was chosen after all five were repacked. Ideally, all the sequences would be synthesized and characterized, but this is impractical due to the difficulties associated with purifying membrane polypeptides, and the large battery of experimental techniques used to examine the membrane protein-binding polypeptides. Thus, the computed sequences were ranked to provide some priorities for experimental verification. Ranking the structures based on calculated energies was difficult, because there was no consistent baseline by which to compare structures of different lengths. Therefore the final rank was based on the uniformity of packing, which was assessed by finding structures with the minimal number of inter-atomic contacts that are smaller than 1.0 Å plus the van der Waals minimum (this is particularly important because of the linear dampening of the Leonard Jones potential). Secondarily, the structures were visually examined to avoid models that showed large voids. The selected template pair has $GX_3G$ (SEQ ID NO:12) motifs in both of its helices, and hence the $\alpha_{IIb}$ sequence was threaded onto either of the two helices, providing two distinct templates for designing membrane protein-binding polypeptides.

Although the depth-dependent knowledge-based potential generally placed residues that prefer the headgroup region in the appropriate positions, two changes were made near the N-terminus of the anti-$\alpha_{IIb}$ helix to help the polypeptide properly orient in the membrane. An exterior residue towards the N-terminus designed to be in the head-group region was set to be Tyr, and Arg3 was changed to Met3 because its side chain appeared closer to the most apolar region of the bilayer. This R3M change resulted in a negligible increase in the calculated energy of the ensemble. Similarly, a tryptophan residue was added near the C-terminus of the anti-$\alpha_{IIb}$ to encourage proper membrane orientation. Final sequences are shown in FIG. 1 and the starting template sequences are provided below (note alignment):

```
Template of anti-αIIb:
PILRGLEVGMAHGYFLIGPWVKL            (SEQ ID NO: 13)

Proximal residues anti-αIIb:
XXXMXXPFXXGLXLGLXFGGXXWGPXRHL      (SEQ ID NO: 14)

Full sequence anti-αIIb:
KKAYVMLLPFFIGLLLGLIFGGAFWGPARHLKK (SEQ ID NO: 15)

Template for αIIb TM:
SEGWSQFTAGFFVGAMGSAFVAFFLLE        (SEQ ID NO: 16)

αIIb TM:
AIPIWWVLVGVLGGLLLLTILVLAMWK        (SEQ ID NO: 17)

Template of anti-αIIb':
SEGWSQFTAGFFVGAMGSAFVAFFLLE        (SEQ ID NO: 16)

Proximal residues anti-αIIb':
XXGXXTFXXGYXXGAXXTGXXYWXXQXXX      (SEQ ID NO: 4)
```

-continued

```
Full sequence anti-αIIb':
KKIFGVLTFLFGYILGALITGAVYWFVQLLAKK (SEQ ID NO: 5)

Template for αIIb TM:
PILRGLEVGMAHGYFLIGPWVKL            (SEQ ID NO: 13)

αIIb TM:
WVLVGVLGGLLLLTILVLAMWKR            (SEQ ID NO: 18)

Template of anti-αV:
DLGFALSGISIAYGFSKFIMGSV            (SEQ ID NO: 19)

Proximal residues anti-αV:
XXXXIXXSFXXGTXXGXXXMFXX            (SEQ ID NO: 7)

Full sequence anti-αV:
AYVFILLSFILGTLLGFLVMFWA            (SEQ ID NO: 8)

Template for αV TM:
AVMFVLLFLCGWFQGMGWPPC              (SEQ ID NO: 20)

αV TM:
PVWVIILAVLAGLLLLAVLVF              (SEQ ID NO: 21)
```

General Peptide Synthesis—Experimental and Control $\alpha_{IIb}$ Polypeptides

The selected membrane protein-binding polypeptide, designated anti-$\alpha_{IIb}$, was prepared by solid phase peptide synthesis. Two control polypeptides were also synthesized: anti-$\alpha_{IIb}$scr, in which the central residues were randomly scrambled, and anti-$\alpha_{IIb}$mut, in which the Gly residues in the GXXXG (SEQ ID NO:12) motifs were mutated to Leu. Computational simulations using the PROTCAD program (see Summa C M et al. *J. Mol. Biol.* 321, 923-938 (2002)) indicate that the $\alpha_{IIb}$ TM helix prefers the binding with anti-$\alpha_{IIb}$ to anti-$\alpha_{IIb}$ scr and anti-$\alpha_{IIb}$mut by over 100 kcal/mole in association energy.

Finally a polypeptide, designated $\alpha_{IIb}$-TM, spanning residues Trp968 to Lys989 of $\alpha_{IIb}$ was synthesized. In order to use fluorescence resonance energy transfer (FRET) for binding measurements, we prepared 7-hydroxycoumarin-3-carboxamide-labeled anti-$\alpha_{IIb}$ (coum-anti-$\alpha_{IIb}$) and anti-$\alpha_{IIb}$mut (coum-anti-($\alpha_{IIb}$mut) as well as fluorescein-5-isothiourea-tagged $\alpha_{IIb}$-TM (FITC-$\alpha_{IIb}$-TM) polypeptides; each label was attached via a linker to the N-terminus of the polypeptide.

The fluorescein-5-isothiocyanate (FITC 'isomer I'; AnaSpec, San Jose, Calif.) label of $\alpha_{IIb}$-TM polypeptide was attached using standard methods. N-ϵ-Fmoc-aminohexanoic acid (Fmoc-ϵ-Ahx-OH; AnaSpec, San Jose, Calif.) was coupled to the amino terminus of the polypeptide-resin using standard manual peptide synthesis conditions. The Fmoc protecting group was removed with 20% piperidine in DMF. Resin was rinsed with DMF four times then swelled with dichloromethane and drained. Fluorescein isothiocyanate (Aldrich, St. Louis, Mo.) was dissolved in a mixture of pyridine/DMF/DCM (12:7:5) to prepare a 0.1 M solution. The resulting solution was added to the resin. The suspension mixture was stirred at room temperature with exclusion of light until the ninhydrin test indicated that the reaction was completed.

The coumarin labeled anti-$\alpha_{IIb}$ and anti-$\alpha_{IIb}$mut polypeptides were prepared using a previously reported method. See Daugherty D L & Gellman S H. *J. Am. Chem. Soc.* 121, 4325-4333 (1999). Labeling of polypeptides with 7-hydroxycoumarin-3-carboxylic acid (Anaspec, San Jose, Calif.) was achieved by methods similar to amino acid couplings on the automated peptide synthesizer. The labeled polypeptides were cleaved from the resin by stirring for 3 h in 2 ml TFA with 100 μl thioanisole and 50 μl ethanedithiol (Aldrich, St. Louis, Mo.).

Peptides were synthesized using an Applied Biosystems 430A peptide synthesizer at 0.25 mmole scales. These peptides were synthesized on a Rink Amide AM resin (200-400 mesh) (Nova Biochem, Merck Biosciences AG, Switzerland) with a substitution level of 0.71 mmole/g. Activation of the free amino acids was achieved with HATU (0.40 M solution in DMF). The reaction solvent contains 25% DMSO and 75% NMP (HPLC grade; Aldrich, St. Louis, Mo.). Sidechain deprotection and simultaneous cleavage from the resin was performed using a mixture of TFA/thioanisole/1,2-ethanedithiol/anisole (90:5:3:3 v/v) at room temperature, under $N_2$ flow for 2 hours. The crude polypeptides collected from precipitation with cold diethyl ether (Aldrich, St. Louis, Mo.) were dissolved in a mixture of 2-propanol:acetonitrile:water (6:3:1) and then lyophilized overnight. The polypeptides were then purified on a preparative reverse phase HPLC system (Varian ProStar 210, Varian, Inc. Walnut Creek, Calif.) with a C-4 preparative column (Vydac, Hesperia, Calif.) using a linear gradient of buffer A (0.1% TFA in Millipore water) and buffer B (6:3:1 2-propanol:acetonitrile:water containing 0.1% TFA). Elution of the purified polypeptides occurred at approximately 65% buffer B. The identities of the purified polypeptides were confirmed by MALDI-TOF mass spectroscopy on a Voyager Biospectrometry Workstation (PerSeptive Biosystems, Framingham, Mass.), and their purity was assessed using an HP 1100 analytical HPLC system (Hewlett Packard, Palo Alto, Calif.) with an analytical C-4 column (Vydac, Hesperia, Calif.) and a linear A/B gradient.

Example 2

Design of Anti-$\alpha_V$

To probe the general applicability of the present approach and specificity of the polypeptide that results, a polypeptide that specifically recognizes the $\alpha_V$ TM domain of $\alpha_V\beta_3$ was designed and functionally characterized. The design of this membrane protein-binding polypeptide was a particularly challenging endeavor because the $\alpha_V$ sequence has an $AX_3G$ (SEQ ID NO:22) rather than a $GX_3G$ (SEQ ID NO:12) motif, which intrinsically has a lower affinity for TM helix-helix interactions (Bowie J U. *J. Mol. Biol.* 272, 780-789 (1997); Curran A R & Engelman D M *Curr. Opin. Struct. Biol.* 13, 412-417 (2003)). Furthermore, the characterization of this was difficult because there is approximately 400-fold less $\alpha_V\beta_3$ than the closely related integrin $\alpha_{IIb}\beta_3$ on platelets (Coller B S et al. *Blood* 77, 75-83 (1991)), In this case, 15 different templates were repacked, and the one that provided the sequence with the best packing was synthesized.

In order to select the optimal template for the design of anti-$\alpha_V$, 15 possible candidate templates were selected from the pair database (see Table 2, below) with helices long enough to span the membrane (both helices at least 20 residues long).

TABLE 2

List of helical pairs with right-handed crossing angles and close helical approaches. An underlined "x" indicates a scaffold that was ultimately used to produce a membrane protein-binding polypeptide. The same scaffolds were used for anti-$\alpha_{IIb}$ and anti-$\alpha_{IIb}'$.

| Helix Pair Name | PDB code | Helix 1* | Helix 2* | Interhelical Distance (Å) | Interhelical Angle (°) | Scaffold for anti-$\alpha_{IIb}$ | Scaffold for anti-$\alpha_V$ |
|---|---|---|---|---|---|---|---|
| 1 | 1jb0 | L46-L55 | L124-L133 | 6.39 | 29.1 | <u>x</u> | x |
| 2 | 1u7g | A234-A245 | A284-A295 | 6.66 | 38.1 | | |
| 3 | 1pw4 | A67-A76 | A127-A136 | 6.68 | 29.1 | | <u>x</u> |
| 4 | 1pv6 | A13-A26 | A142-A155 | 6.78 | 34.3 | | x |
| 5 | 1rc2 | D138-D147 | D210-D219 | 6.88 | 42.9 | | x |
| 6 | 1pw4 | A294-A305 | A351-A362 | 6.99 | 40.6 | | x |
| 7 | 1xfh | B22-B31 | B210-B219 | 7.00 | 31.7 | | |
| 8 | 1fx8 | B11-B24 | B89-B102 | 7.01 | 36.6 | | x |
| 9 | 1rc2 | B5-B17 | B84-B96 | 7.02 | 39.6 | | x |
| 10 | 1eul | A769-A779 | A839-A849 | 7.03 | 44.2 | | x |
| 11 | 1kpl | B37-B50 | B215-B228 | 7.03 | 33.1 | | |
| 12 | 1q90 | M74-M85 | N81-N92 | 7.05 | 39.5 | | |
| 13 | 1j4n | D145-D158 | D216-D229 | 7.06 | 41.4 | | x |
| 14 | 1kpl | A252-A264 | A424-A436 | 7.08 | 35.1 | x | |
| 15 | 1q90 | G4-G15 | M65-M76 | 7.14 | 43.9 | | |
| 16 | 1xfh | A92-A102 | A311-A321 | 7.20 | 28.7 | | |
| 17 | 1u7g | A264-A276 | A317-A329 | 7.23 | 35.7 | | |
| 18 | 1fx8 | D147-D157 | D234-D244 | 7.27 | 40.1 | | x |
| 19 | 1pw4 | A261-A270 | A392-A401 | 7.29 | 44.5 | | x |
| 20 | 1ocr | A24-A33 | L29-L38 | 7.36 | 34.1 | | |
| 21 | 1fx8 | A93-A102 | A204-A213 | 7.43 | 45.7 | | |
| 22 | 1rc2 | D63-D72 | D212-D221 | 7.51 | 31.8 | | |
| 23 | 1m56 | A240-A249 | C87-C96 | 7.56 | 38.8 | | x |
| 24 | 1kpl | B53-B62 | B130-B139 | 7.63 | 38.3 | | |
| 25 | 1ocr | A196-A205 | C89-C98 | 7.64 | 37.4 | | x |
| 26 | 1j4n | A194-A203 | A102-A111 | 7.66 | 38.5 | | |
| 27 | 1k4c | C63-C73 | C92-C102 | 7.68 | 49.0 | | |
| 28 | 1pp9 | C322-C331 | G44-G53 | 7.80 | 32.6 | | |
| 29 | 1j4n | B18-B28 | B100-B110 | 7.81 | 36.5 | | x |
| 30 | 1msl | B18-B27 | C19-C28 | 7.81 | 38.4 | | |
| 31 | 1q90 | L3-L15 | N74-N86 | 7.98 | 44.7 | | |
| 32 | 1kpl | B33-B50 | B171-B188 | | | | x |

TABLE 2-continued

List of helical pairs with right-handed crossing angles and close helical approaches. An underlined "x" indicates a scaffold that was ultimately used to produce a membrane protein-binding polypeptide. The same scaffolds were used for anti-$\alpha_{IIb}$ and anti-$\alpha_{IIb}$'.

| Helix Pair Name | PDB code | Helix 1* | Helix 2* | Interhelical Distance (Å) | Interhelical Angle (°) | Scaffold for anti-$\alpha_{IIb}$ | Scaffold for anti-$\alpha_v$ |
|---|---|---|---|---|---|---|---|
| 33 | 1kpl | B36-B54 | B217-B231 | | | x | |
| 34 | 1fx8 | A148-A165 | A235-A252 | | | x | |
| 35 | 1ocr | A96-A105 | C15-C24 | 8.00 | 35.6 | | x |

*The range refers to the region where the helices come into close contact.

These templates were repacked. The calculated residue of closest approach was used for determining the position of the AX$_3$G (SEQ ID NO:22) motif in the $\alpha_V$ sequence. The proximal residues chosen for repacking were determined computationally. Using HELANAL6 the center of the helix for each residue was calculated. The angle between the vector created by the center point of a given residue and the center point of its nearest residue on the opposite helix and the vector of the center residue of the given residue with the Cβ of that residue was calculated. If the angle was less than 70° the residue was considered to be a proximal residue. Once the templates were repacked, all of them were examined. Many of them could not reach a low energy solution—largely because of steric clashes between the backbone of the anti-$\alpha_V$ helix with the leucine reside at the i+4 position from the AX$_3$G (SEQ ID NO:22) motif. Eight templates did allow for a low energy solution. To eliminate a few bad interactions, the structures were minimized to find local low energy solutions (between 100 and 500 cycles of steepest descents minimization using the GROMOS force field) and then repacked the side chains of the resultant backbones using the PROTCAD protocol described above (Example 1, supra). After this second step of repacking the new structures underwent another round of minimization. Further selection of template based on a comparison of the calculated energy of the structures was deemed insufficient as we had no consistent baseline by which to compare structures of different lengths. As was the case for the anti-$\alpha_{IIb}$ polypeptides, the final eight structures were ranked based on their uniformity of packing, as assessed by finding structures the with minimal number of interatomic contacts that are smaller than 1.0 Å from the van der Waals minimum, and that had few large voids. Ultimately, the backbone template selected for the design of anti-$\alpha_V$ was the glycerol-3-phosphate transporter (G3P transporter) (1PDW4, residues A64-A86 and A121-A141). With this backbone, the sequence of the integrin $\alpha_V$ TM domain was threaded onto the second helix of the G3P transporter structure. Because of the use of the computational proximal position-picking algorithm described above, only eight residues were selected for repacking based on their proximity to the $\alpha_V$-threaded helix. Assignment of the membrane-exposed residues in the anti-$\alpha_V$ was modeled on the membrane-exposed residues of the anti-$\alpha_{IIb}$. The sequence before and after the addition of membrane exposed residue identities is illustrated above. See Example 1, supra.

Figure 6:
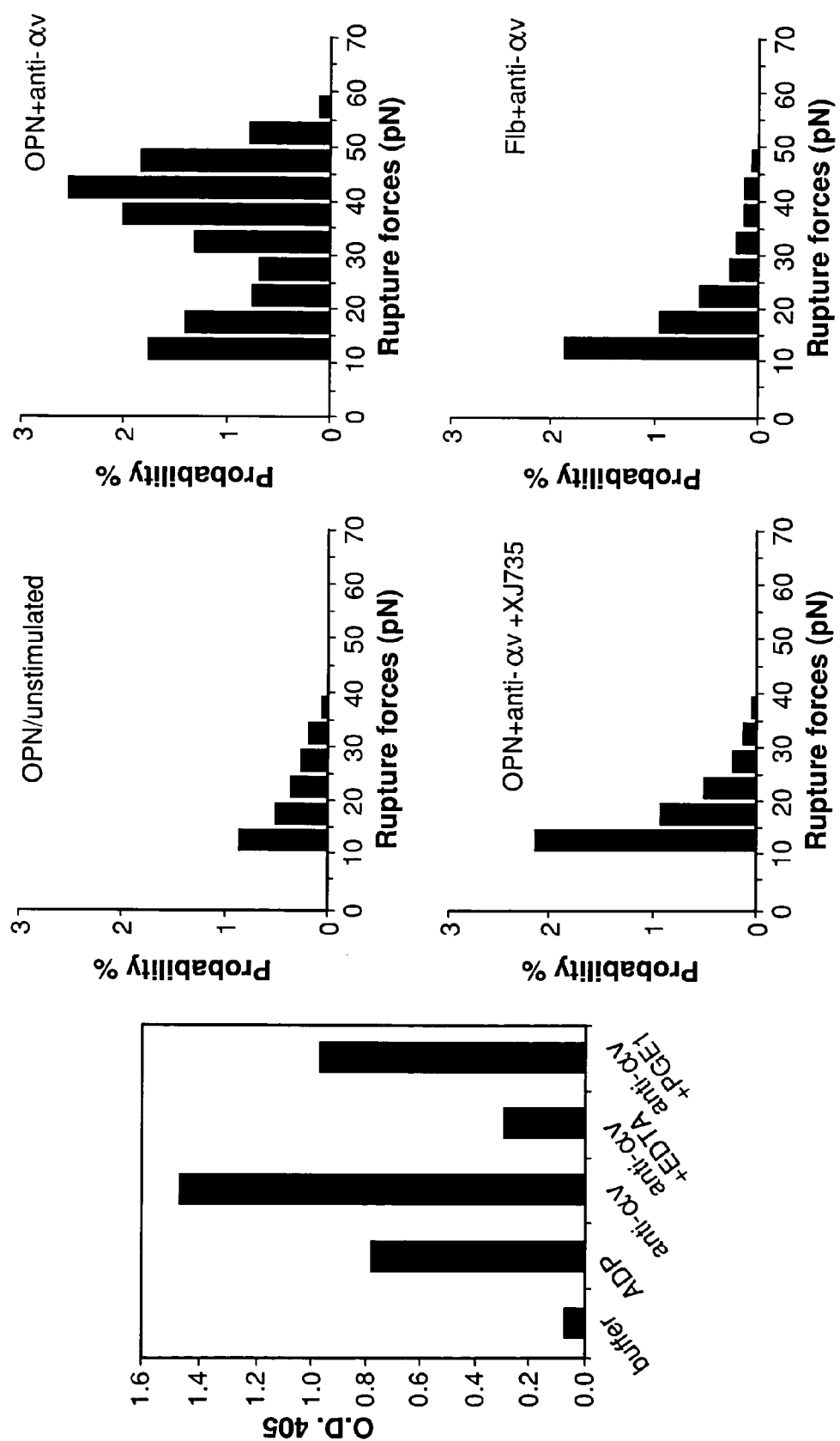
FIG. 6 demonstrates that anti-$\alpha_v$ induces the anti-$\alpha_v\beta_3$-mediated interaction of platelets with osteopontin.

Anti-$\alpha_V$ specifically activated $\alpha_v\beta_3$ in platelets, as assessed by its ability to induce platelet adhesion to osteopontin (FIG. 6a). Furthermore, adhesion was only minimally affected by pre-incubating the platelets with PGE1, whereas it was prevented by the addition of EDTA, findings consistent with the expectation that the anti-$\alpha_V$-induced adhesion is mediated by a direct interaction with $\alpha_v\beta_3$. Force spectroscopy further demonstrated the specificity of the interaction. In these experiments, rupture forces between platelets and beads coated with either osteopontin or fibrinogen were measured in the presence or absence of anti-$\alpha_V$. Only non-specific rupture forces were detected between osteopontin-coated beads and the platelet surface in the absence of anti-$\alpha_V$ (FIG. 6b). However, in the presence of anti-$\alpha_V$, a new peak was observed with a maximum at 40 pN (FIG. 6c). The peak is similar to that observed when platelets were stimulated with ADP27, and it was not present when anti-$\alpha_V$ was added in the presence of the αvβ3 antagonist XJ735 (FIG. 6d). Moreover, no peak of specific rupture force was observed when the beads were coated with fibrinogen rather than osteopontin (FIG. 6e). Thus, these results indicate that anti-$\alpha_V$ can specifically recognize and activate $\alpha_v\beta_3$ in the presence of a 400-fold excess of $\alpha_{IIb}\beta_3$. The specificity of the membrane protein-binding polypeptide that results from the disclosed membrane protein-binding polypeptide design process is therefore extremely high and as such resembles that of antibodies for their antigens.

Example 3

Circular Dichroism Spectroscopy

Secondary structure of the prepared polypeptides was analyzed using Circular Dichroism (CD).

Figure 7:
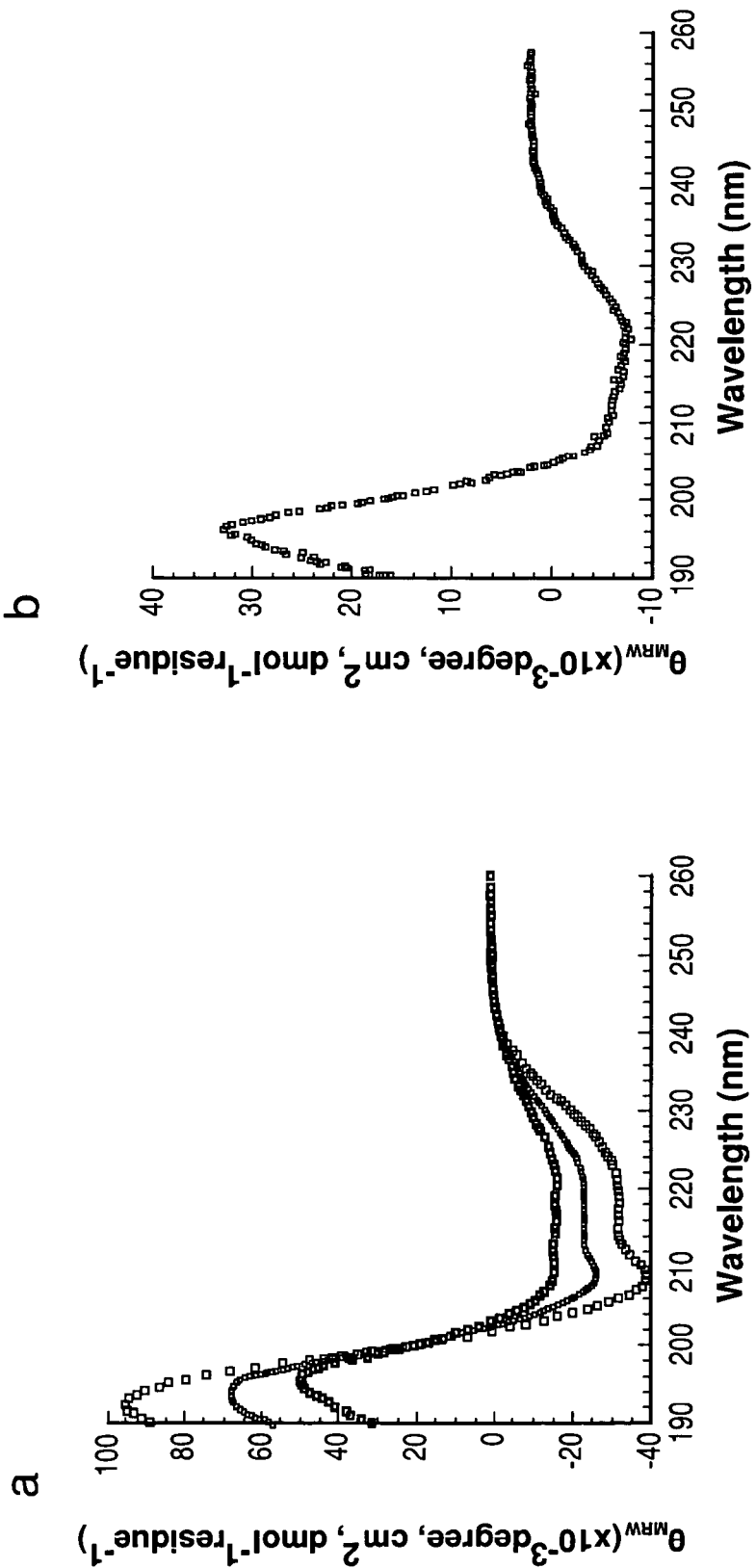
FIG. 7 provides circular dichroism spectra of the polypeptides produced according to the present example.

FIG. 7 provides the circular dichroism spectra of the membrane protein-binding polypeptides. FIG. 7a shows the CD spectra of the anti-$\alpha_{IIb}$ (1), and $\alpha_{IIb}$-TM (3) polypeptides, as well as their 1:1 mixture (2) in 2.5 mM DPC (CMC=1.0 mM). FIG. 7b depicts the CD spectrum for anti-$\alpha_{IIb}$ in 500 μM unilamellar vesicles (POPC:POPG=8:2).

CD spectrometry experiments were carried out using a J-810 spectropolarimeter (JASCO, Inc., Easton, Md.). Polypeptide samples were prepared at 20 μM concentration in micelles (2.5 mM 1,2-dihexanoyl-sn-glycero-3-phosphocholine; Sigma-Aldrich, St. Louis, Mo.) or unilamellar vesicles (500 μM total phospholipid composed of POPC and POPG (Avanti Polar Lipids Inc., Alabaster, Ala.) at an 8:2 ratio). Measurements were conducted at 25° C. in step scanning mode with a response time of 4 seconds. Accumulation of three independent measurements were averaged.

Circular dichroism (CD) spectroscopy revealed that anti-$\alpha_{IIb}$, $\alpha_{IIb}$-TM, as well as their 1:1 mixture, were predominantly helical in micelles and unilamellar vesicles (FIG. 7).

Example 3a

Attenuated Total Reflectance IR Spectroscopy

Figure 14:
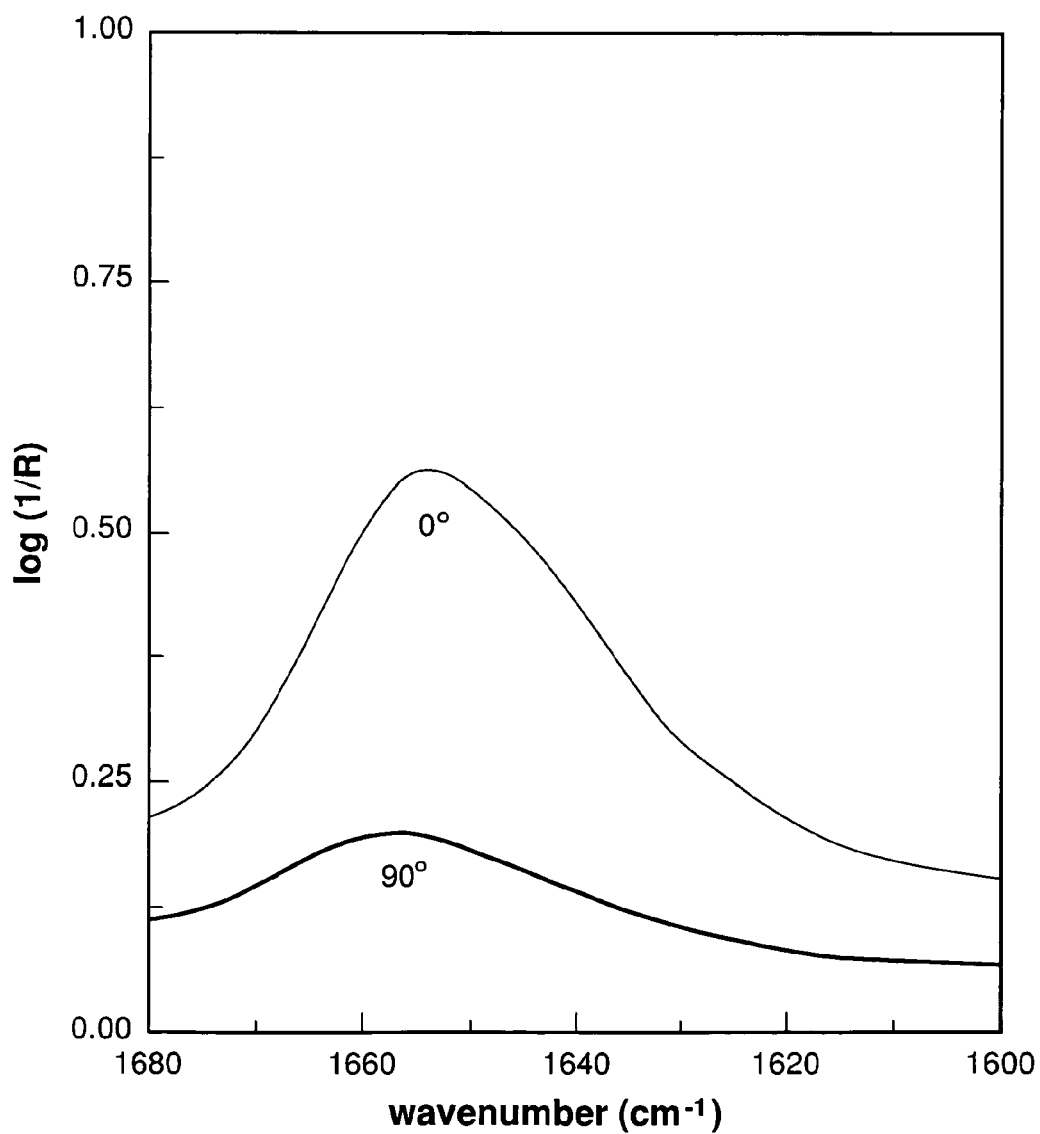
FIG. 14 provides attenuated total reflectance-IR spectroscopy which shows that vesicle-bound anti-$\alpha_{IIb}$ polypeptide adopts a transmembrane orientation.

Attenuated total reflectance-IR spectroscopy revealed that vesicle-bound polypeptides adopted a transmembrane orientation, with their helix perpendicular to the bilayer surface. FIG. 14 depicts polarized ATR-IR spectra of anti-$\alpha_{IIb}$ reconstituted into vesicles (POPC/POPG, 7:3). Shown are representative spectra from the same sample irradiated with light polarized at 0° and 90°. The amide-I vibration is centered at 1657 cm$^{-1}$ and exhibits an average dichroic ratio of 4.6. This corresponds to the peptide adopting a transmembrane orientation at an angle of approximately 20° with respect to the membrane normal.

Example 4

Analytical Centrifugation

Equilibrium sedimentation was used primarily to determine the association state of the peptides, but also to provide a rough estimate of the heterodimeric association constants. The experiments were performed in a Beckman XL-I analytical ultracentrifuge (Beckman Coulter) using six-channel carbon-epoxy composite centerpieces at 25° C. Peptides were co-dissolved in CF$_3$CH$_2$OH (Sigma-Aldrich, St. Louis, Mo.) and C14-betaine (3-(N,N-dimethylmyristyl-ammonio)propanesulfonate; Sigma-Aldrich, St. Louis, Mo.). The organic solvent was removed under reduced pressure to generate a thin film of peptide/detergent mixture, which was then dissolved in buffer previously determined to match the density of the detergent component (20 in M HEPES (pH=7.4) buffer containing 29% D$_2$O). Tanford, C, Reynolds, J A, *Biochim. Biophys. Acta.* 1976, 457, 133-170. The final concentration of C-14 betaine is 5 mM in the samples. Samples were prepared in a total peptide concentration of 50 μM (in case of heterodimer formation, a 1:1 mixture was prepared) and incubated overnight. Data at three measurement speeds (40, 45, and 50 KRPM for αIIb peptides and 30, 35, and 40 KRPM for the αv peptides) were analyzed by global curve-fitting of radial concentration gradients (measured using optical absorption) (FIG. 8a-8f) to the sedimentation equilibrium equation for monomer-dimer equilibria among the peptides included in the solution. Peptide partial specific volumes were calculated using previously described methods (see Kharakokoz, D. P. *Biochemistry* 1997, 33, 10276-10285) and residue molecular weights corrected for the 29% D$_2$O exchange expected for the density-matched buffer. The solvent density (1.0245 g/ml) was measured using a Paar densitometer. Aqueous solution molar extinction coefficients at 280 nm were calculated using the program Sednterp. Laue, T; Shaw, B. D.; Ridgeway, T M.; Pelletier, S. L. *Computer-aided interpretation of analytical sedimentation data for proteins; the Royal Society of Chemistry; Cambridge (U.K.)* 1992, 90-125. These coefficients were multiplied by the molar detergent concentration to provide mole ratio concentration units.

Ultracentrifugation data (FIG. 8) were first collected for the individual peptides. The data for all four peptides conformed well to a monomer-dimer equilibrium, although the association for αv-TM was so weak that it was essentially fully monomeric under these conditions. Integrated component concentrations were assessed to avoid unrealistic local minima, and errors were estimated using post-fitting material balance calculation. Arkin, M.; Lear, J. D. *Anal. Biochem.* 2001, 299, 98-107. Next, ultracentrifugation data of a 1:1 mixture of the membrane protein-binding peptides (50 μM each) and their targets were then collected. The data were analyzed using the scheme in FIG. 8g; the homomeric association constants (pK$_{mon1}$ and pK$_{mon2}$) were known from the experiments in which the peptides were studied individually, so the heteromeric dissociation constant (pK$_{het}$) and the baseline were the parameters allowed to vary while analyzing the data. For both peptides, the heterodimerization pK$_{diss}$ was always found to be larger than that for the homodimers alone (indicating that the heteromeric association was more favorable than the homomeric association). However, the heteromeric pK$_{diss}$ values obtained in this manner reflect the uncertainties in the monomeric pK$_{diss}$ values too, rendering it difficult to place an upper limit on the pK$_{diss}$ for anti-αv/αv-TM. The value of pK$_{diss}$ for anti-αIIb/αIIb-TM is also uncertain, and the error reported in Table 1 is a lower limit as it reflects only the fitting error associated with each species. We therefore used FRET to directly measure the heteromeric association of these peptides.

TABLE 1

Analytical ultracentrifuge sedimentation results (50 μM polypeptides in 5 mM C14-betaine (CMC = 0.1 mM), 20 mM HEPES, pH = 7.4, 29.5% D$_2$O). See FIG. 8.

| Dimerization Pair | Dimerization pK$_{diss}$ |
|---|---|
| $\alpha_{IIb}$-TM | 1.8 ± 0.3 |
| Anti-$\alpha_{IIb}$ (FITC-labeled) | 2.3 ± 0.1 |
| $\alpha_{IIb}$-TM-FITC/anti-$\alpha_{IIb}$ | 2.6 ± 0.5* (3.5)# |
| $\alpha_V$-TM | 0.7 ± 1 |
| Anti-$\alpha_V$(coumarin-labeled) | 1.4 ± 0.2 |
| $\alpha_V$-TM-coum/anti-$\alpha_V$ | >2* (2.9)# |

*The error reported reflects the fitting error from the homomeric pK$_{diss}$ values, plus the error associated with the fitting errors associated with the heteromeric pK$_{diss}$ values.
pK$_{diss}$ value from FRET experiments with both peptides labelled.

Analytical ultracentrifugation indicated that both anti-$\alpha_{IIb}$ and $\alpha_{IIb}$-TM form homodimeric complexes in zwitterionic C14-betaine micelles (see Table 1, supra). When the anti-$\alpha_{IIb}$ and $\alpha_{IIb}$-TM polypeptides were mixed in a 1:1 mole ratio, heterodimers were formed and no aggregates larger than dimers were detected. The heterodimer association appeared to be at least as strong as the anti-αIIb homodimerization.

Example 5

Heterodimeric Association—Fluorescence Resonance Energy Transfer

Figure 2:
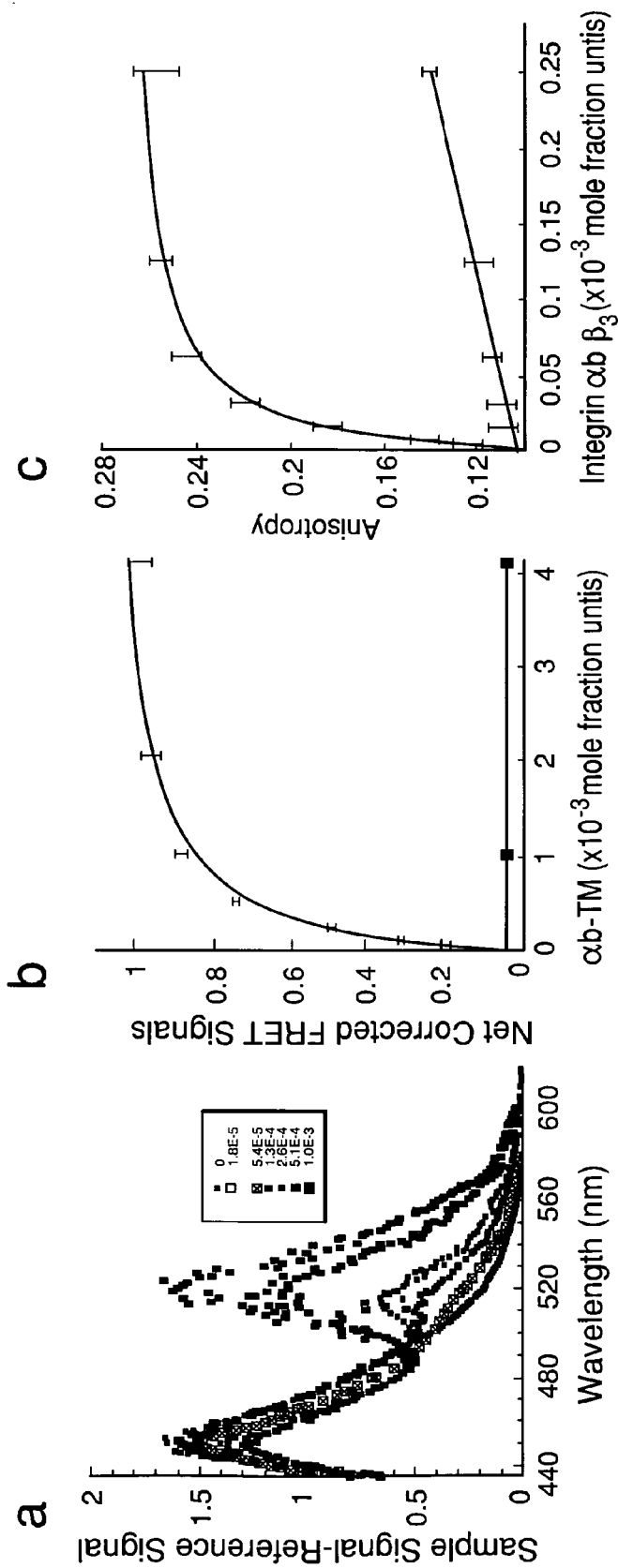
FIG. 2 presents graphical data from in vitro studies of anti-$\alpha_{IIb}$ polypeptide binding to the $\alpha_{IIb}$-transmembrane domain.

FRET provided a more direct measure of the $\alpha_{IIb}$-TM/anti-$\alpha_{IIb}$ heterodimeric association. Titration of coum-anti-$\alpha_{IIb}$ as a FRET donor, with FITC-$\alpha_{IIb}$-TM as a FRET acceptor, resulted in quenching of the coumarin emission and the appearance of fluorescein emission, indicating that the two polypeptides associated (FIG. 2a). By contrast, there was negligible interaction observed between FITC-$\alpha_{IIb}$-TM and coum-anti-$\alpha_{IIb}$mut. Because the appropriate parameter for the association of polypeptides in micelles is generally the polypeptide concentration in the detergent micellar phase rather than the bulk polypeptide concentration, dissociation constants are often given in mole fraction units (polypeptide/detergent ratios). Fleming K G. *J. Mol. Biol.* 323, 563-71 (2002). The apparent K$_{diss}$ for the $\alpha_{IIb}$-TM/anti-$\alpha_{IIb}$ interaction, expressed in mole fraction units, was computed to be 3.2±0.5×10$^{-4}$ (FIG. 2b), indicative of very tight association compared to a variety of other membrane polypeptide associations. See Fleming K G (2002). Similar energy transfers between coum-anti-$\alpha_{IIb}$ and FITC-$\alpha_{IIb}$-TM was also observed in unilamellar vesicles (data not shown).

Fluorescence resonance energy transfer (FRET) experiments were conducted on an ATF 105 spectrofluorometer (Aviv Biomedical, Inc., Lakewood, N.J.) using 0.3 cm path length cuvettes. Sample mixtures with 64 nM (7-hydroxy-3-carboxyamide coumarin)-labeled anti-$\alpha_{IIb}$ polypeptide (coum-anti-$\alpha_{IIb}$), or control polypeptide (coum-anti-$\alpha_{IIb}$-mut), in the presence of increasing concentrations of FITC-labeled $\alpha_{IIb}$-TM polypeptide (FITC-$\alpha_{IIb}$-TM) in buffer (10 mM HEPES, pH=7.5, 1 mM 3-(N,N-dimethylmyristylammonio)propanesulfonate (Sigma-Aldrich, St. Louis, Mo.)) were prepared and left to incubate overnight at 4° C. Reference samples contain the same amount of FITC-$\alpha_{IIb}$-TM and non-labeled anti-$\alpha_{IIb}$ to their corresponding FRET samples. Emission and excitation scans of the 1:1 mixture of FITC-$\alpha_{IIb}$-TM/coum-anti-$\alpha_{IIb}$ were carried out to determine the optimal excitation and emission wavelengths. Excitation at 415 nm was selected. For the titration experiments in FIG. 2b, the emission at 500 nm was monitored. A slit width of 1.5 nm was used for both the excitation and emission. The signal and QC PMT high voltages were set at 737.3 V and 75.0 V, respectively. For the time-domain experiments, an experiment time of 600 seconds with 10 seconds of interval time and 10 seconds of average time was used. The net FRET signals (signal from a sample with donor coum-anti-$\alpha_{IIb}$ and acceptor FITC-$\alpha_{IIb}$-TM minus the signal from a reference with unlabeled anti-$\alpha_{II}$ and acceptor FITC-$\alpha_{IIb}$-TM) were used for data analysis. The fluorescence intensity values were used after correction of the inner filter effects using the standard method. See Lakowicz J R. *Principles of Fluorescence Spectroscopy* (2d ed. Kluwer Acad.: N.Y., 1999), at chapter 1 p. 53. Data of the net FRET signals with increasing concentrations of FITC-$\alpha_{IIb}$-TM were fitted using an equation derived from monomer-dimer equilibria among the different species, solved using a root-finding algorithm in IGOR Pro (Wavemetrics, Inc., Portland, Oreg.).

Example 6

Fluorescence Anisotropy Assay—Membrane Protein-Binding Polypeptide Association with Full Length Integrin Fluorescence anisotropy titrations indicated that anti-$\alpha_{IIb}$ also associates with the full-length $\alpha_{IIb}\beta_3$ integrin molecule in N-octyl-$\beta$-D-glucopyranoside micelles (FIG. 2c). Measurement of the anisotropy of coum-anti-$\alpha_{IIb}$ as a function of the concentration of $\alpha_{IIb}\beta_3$ revealed a binding isotherm with an apparent $K_{diss}$ of $1.3\pm0.2\times10^{-5}$ in mole fraction units, indicating that the polypeptide also binds tightly to the intact integrin. By contrast, the control polypeptide coum-anti-$\alpha_{IIb}$mut displayed at least 100-fold lower affinity for $\alpha_{IIb}\beta_3$.

The full-length integrin $a_{IIb}\beta_3$ protein in buffer (7.9 mg/ml, 10 mM HEPES (pH=7.5), 60 mM N-octyl-$\beta$-D-glucopyranoside, 0.5 mM $CaCl_2$, 0.02% $NaN_3$) was prepared using the previously reported method. Weisel J W et al. *J. Biol. Chem.* 267, 16637-16643 (1992). Fluorescence polarization experiments were conducted on an ATF 105 spectrofluorometer (Aviv Biomedical, Inc., Lakewood, N.J.) using a 0.3 cm path length cuvette. Spectra were measured at 25° C. using 1.0 nm slit widths. Excitation at 408 nm was used for the coumarin-labeled polypeptide and the emission maximum at 433 nm was monitored. Anisotropy measurements were recorded upon titration of the integrin $\alpha_{IIb}\beta_3$ protein at varying concentrations into a polypeptide solution of 64 nM coum-anti-$\alpha_{IIb}$ or coum-anti-$\alpha_{IIb}$mut. Data analysis was carried out according to previously described methods. See Yin H et al. *J. Am. Chem. Soc.* 127, 10191-96 (2005).

Example 6a

Dominant-Negative (DN) TOXCAT

Figure 3:
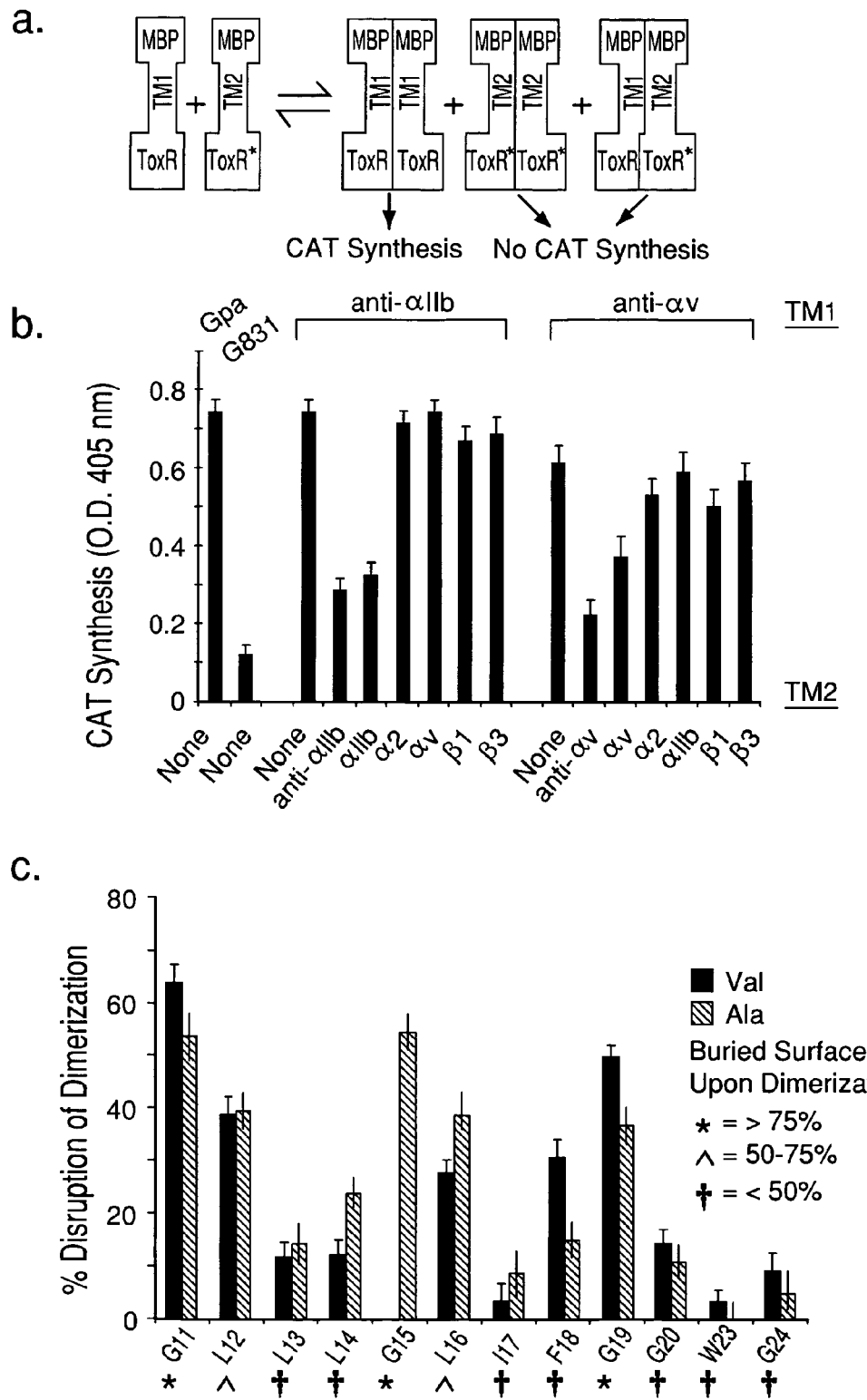
FIG. 3 illustrates the DN-TOXCAT experimental technique and provide findings as to the specificity of inventive polypeptides as determined from the DN-TOXCAT assay.

Both the affinity and specificity of the membrane protein-binding peptides for their targets when coexpressed in bacterial membranes were assessed with a DN-"TOXCAT" assay (FIGS. 3a-3c). In TOXCAT, a TM sequence of interest is fused to a ToxR protein (TM-ToxR) that binds to the ctx promoter as a dimer, which induces expression of chloramphenicol acetyltransferase (CAT) (W. P. Russ, D. M. Engelman, *Proc. Natl. Acad. Sci. U.S.A.* 96, 863 (1999); D. Langosch, B. Brosig, H. Kolmar, H. J. Fritz, *J. Mol. Biol.* 263, 525 (1996)). In the DN assay, the TM1-ToxR fusion protein is coexpressed with a second fusion protein (TM2-ToxR*) containing a nonfunctional mutant of the ToxR domain. TM-driven dimerization leads to a ToxR-ToxR* dimer that is unable to bind the ctx promoter or to induce CAT synthesis (FIG. 3a). The resulting decrease in CAT activity can be used to monitor the formation of a heterodimeric TM complex. In principle, this assay could be accomplished by adding an exogenous synthetic peptide (D. Gerber, N. Sal-Man, Y. Shai, *J. Mol. Biol.* 339, 243 (2004)); however, it is difficult to assure that different peptides will be similarly inserted into the *Escherichia coli* inner membrane.

The anti-$\alpha_{IIb}$ and anti-$\alpha_v$ peptides both formed homodimers in bacterial membranes (FIG. 3b) with an affinity similar to that of the TM domain of glycophorin A (GpA), which forms tight homodimers in this environment (W P. Russ & D. M Engelman (1999); D. Langosch et al., (1996)). The CAT signal for the anti-$\alpha_{IIb}$-ToxR construct was attenuated by coexpression of anti-$\alpha_{IIb}$-ToxR* (FIG. 3b), validating the DN assay. When $\alpha_{IIb}$ was used as the DN partner, the signal from anti-$\alpha_{IIb}$-ToxR was also strongly attenuated, indicative of heterodimer formation. The magnitude of the decrease in CAT signal due to heterodimerization of anti-$\alpha_{IIb}$ with $\alpha_{IIb}$ TM is particularly notable. The homodimerization of anti-$\alpha_{IIb}$ and GpA (W. P. Russ & D. M. Engelman (1999); D. Langosch et al., (1996)) are similar in affinity (FIG. 3b, first versus third bar). Thus, because the attenuation of the CAT signal in the DN-TOXCAT assay for an anti-$\alpha_{IIb}$-anti-$\alpha_{IIb}$ homodimer is similar to that of the anti-$\alpha_{IIb}$-$\alpha_{IIb}$ TM heterodimer (FIG. 3b, fourth versus fifth bar), the heterodimeric TM complex anti-$\alpha_{IIb}$-$\alpha_{IIb}$ has similarly strong affinity to that of the anti-aIIb homodimer and therefore also to the GpA homodimer.

The TOXCAT assay also shows that anti-$\alpha_{IIb}$ and anti-$\alpha_v$ are highly specific for their targets versus other integrin TM domains. The TM domains of $\alpha_2$, $\alpha_v$, $\beta_1$, or $\beta_3$ failed to significantly interact with anti-aIIb, despite their high sequence and structural similarity to the $\alpha_{IIb}$ TM. Similarly, anti-$\alpha_v$ selectively recognized the TM domain with much greater affinity than the $\alpha_2$, $\alpha_{IIb}$, $\beta_1$, or $\beta_3$ domains.

To probe whether anti-$\alpha_{IIb}$ recognized its target in the intended manner, the effect of mutating residues in anti-$\alpha_{IIb}$ TM to either V or A was measured. FIG. 3c depicts the effect of mutations in the anti-$\alpha_{IIb}$ sequence on heterodimerization with $\alpha_{IIb}$. Black bars represent V substitutions, and gray bars represent A substitutions. Mutations to key residues are highlighted according to their buried surface area upon dimerization (see SOM): >75% buried (*), 50 to 75% buried (^), and <50% buried (†). The percent disruption of heterodimerization correlates with the predicted amount of area buried upon dimerization, indicating that the anti-$\alpha_{IIb}$ peptide recognizes $\alpha_{IIb}$-TM, as in the designed complex. Error bars represent standard deviation of the mean. Mutations to the residues predicted to occur at the helix-helix interface caused disruption of heterodimer formation. Very large effects were observed for buried residues within a 10-residue stretch (residues 11 to 20) spanning the primary interaction site, whereas only minor effects were observed for residues on the non-interacting side of the helix or the more distal sites (residues 23 and 24). Interestingly, the interaction face resembles a "Gly-zipper" (GX$_3$GX$_3$G) (SEQ ID NO:23) motif that has recently been shown to mediate intermolecular helix-helix associations in membranes (S. Kim et al., *Proc. Natl. Acad. Sci. U.S.A.* 102, 14278 (2005)).

Primers specific to the pETDuet-1 vector (Novagen) were designed and used to amplify the 329 by fragment between SphI (5191) and NcoI (89). The forward primer (tttttttttgcat-gcaccggtgtttaaacaaggagatggcgcccaacagtc) (SEQ ID NO:24) introduced AgeI (italics) and PmeI (underlined) sites immediately downstream of SphI (bold) and the reverse primer (tttttttttccatggACTAGTgtatatctccttcttaaagttaaa) (SEQ ID NO:25) introduced a SpeI site (capital letters) immediately upstream of NcoI (bold).

Point mutation R96K in the ToxR gene was generated previously to make the pccKAN* vector. Berger, B. W et al. 2006, *Manuscript in preparation*. R96K has been shown previously to abolish the DNA binding ability of ToxR in *E. coli* without altering expression levels relative to wt ToxR. Ottenmann, K M, DiRita, V. J. and Mekalanos, J. J. *J. Bacteriol.* 1992, 174, 6807-6814.

TOXCAT plasmids containing the TM sequences of $\alpha_2$, $\alpha_{IIb}$, $\alpha_v$, $\beta_1$ and $\beta_3$ were generated previously. For anti-$\alpha_{IIb}$, synthetic oligonucleotides corresponding to the peptide sequence were generated (GCGTATGTGATGCTGCTGC-CGTTTTTCATTGGCCTGCTTCTGGGCCT-GATTTTTGGCG GTGCGTTTTGGGGCCCGGCGCGC-CATCTG) (SEQ ID NO:3) and used as a template, amplifying with sequence specific primers that introduced a forward NheI (bold) (AAAAAAAAAGCTAGC-GACGTCGCGTAT) (SEQ ID NO:26) and reverse BamHI (underlined) (AAAAAAAAA GGATCCCTCGAGCAGATG) (SEQ ID NO:27) site. The TM fragment was gel purified, digested with NheI and BamHI (NEB) and ligated in-frame with NheI/BamHI digested pccKAN and pccKAN* vectors.

For the heteroassociation assay, the ctx::CAT region of pccKAN (7800-8500) was amplified using specific primers that introduced forward SphI site (bold) (AAAAAAAAAG-CATGCTCGACGAATTTCTGCCATTC) (SEQ ID NO:28) and reverse (AAAAAAAAAAAAAAATAGGCGTATCAC-GAGGC) (SEQ ID NO:29), digested with SphI and ClaI and ligated into pETDuet-1 (Novagen) to make the pCAT-Duet vector.

ToxR-TM-MBP fusion constructs were amplified from their respective TOXCAT plasmids and cloned into MCS1 using primers that introduce forward SpeI (bold) (AAAAAAAATACTAGTatgtcggattaggacacaactc) (SEQ ID NO:30) and reverse HindIII (aaaaaaattAAGCTTttaCGCAT-AATCCGGCACATCATACGGATAagtctgcgcgtctttcag) (SEQ ID NO:31) sites and MCS2 using primers that introduce forward KpnI (bold) (AAAAAAATTGGTACCTC-CATGGTCGGATTAGGACACAACTCA) (SEQ ID NO:32) and reverse PacI (underlined) (aaaaaaaaattaattaaTCAG-ATCTTCTTCGCTAATCAGTTTCTGTTCagtctgcgcgtcttt-cag) (SEQ ID NO:33) sites of the pCAT-Duet to create pDN-ToxR-Duet. An HA (italics) (YPYDVPDYA) (SEQ ID NO:34) and myc (italics) (EQKLISEEDL) (SEQ ID NO:35) epitope tag was introduced at the C-terminus of the fusion constructs using the reverse primers for MCS1 and MCS2, respectively.

The peptide sequences of the TM domains used in the DN ToxCAT study are printed below.

| | | |
|---|---|---|
| $\alpha_{IIb}$: | KWVLVGVLGGLLLLTILVLAMWKK | (SEQ ID NO: 36) |
| $\alpha_V$: | KPVWVIILAVLAGLLLLAVLVFK | (SEQ ID NO: 37) |
| $\alpha_2$: | KGVIIGSIIAGILLLLALVAILWK | (SEQ ID NO: 38) |
| $\beta_1$: | KIIPIVAGVVAGIVLIGLALLLIWKK | (SEQ ID NO: 39) |
| $\beta_3$: | KILVVLLSVMGAILLIGLAALLIWK | (SEQ ID NO: 40) |

For testing the specificity of the designed membrane protein-binding polypeptide sequences against the integrin TM domains, the designed sequences (anti-$\alpha_{IIb}$ and anti-$\alpha_V$) were cloned into MCS1 of the Duet vector and the integrin TM domains into MCS2 of the Duet vector. In this configuration, the integrin TMs compete for the homodimers formed by the polypeptide sequences, with the decrease in CAT signal proportional to the extent of heterodimerization between a given integrin TM and polypeptide sequence relative to the homodimerization of the polypeptide sequence.

For site-directed mutagenesis to test the specificity of the anti-$\alpha_{IIb}$ design, PrimerX (http://bioinformatics.org/prim-erx/) was used to generate primers to introduce valine and alanine substitutions in anti-$\alpha_{IIb}$ (underlined):

(SEQ ID NO: 2)
anti-$\alpha_{IIb}$:    AYVMLLPFFI<u>GLLLGLIFGGAFWG</u>PARHL

Mutants were generated using the QuikChange site-directed mutagenesis kit (Stratagene). Note that A21V, F22V, F22A and G15V did not express and were therefore not characterized. In this configuration, the $\alpha_{IIb}$ TM domain was cloned into MCS1 and various anti-$\alpha_{IIb}$ mutants cloned into MCS2. Thus, the anti-$\alpha_{IIb}$ mutants compete for homodimerization of $\alpha_{IIb}$. In order to quantify the effects of mutations to anti-$\alpha_{IIb}$ on the change in heterodimerization relative to wild-type anti-$\alpha_{IIb}$, a disruption index (or % disruption of heterodimerization) was calculated from the data as follows:

$$\text{\% Disruption of Hetero dimerization} (1-f) = \frac{Obs - Min}{Max - Min}$$

Obs is the observed signal for a given mutant, Max is the signal for the $\alpha_{IIb}$ homodimer and Min is the observed signal for the wild-type anti-$\alpha_{IIb}$/$\alpha_{IIb}$ heterodimer.

For comparison with the % disruption of heterodimerization, probe-accessible surface areas for the $\alpha_{IIb}$ monomer, anti-$\alpha_{IIb}$ monomer and $\alpha_{IIb}$/anti-$\alpha_{IIb}$ heterodimer were calculated from the models using CHARMM with a 2.8 Å probe radius (to simulate the cross-sectional area of a fatty acid acyl chain). The fraction buried surface area upon heterodimerization was calculated as the difference between the anti-$\alpha_{IIb}$ monomer and $\alpha_{IIb}$/anti-$\alpha_{IIb}$ heterodimer relative to the anti-$\alpha_{IIb}$ monomer. Similar results were obtained when the probe size was varied from 1.4 to 2.8 Å.

Expression and characterization:

Single MM39 colonies containing pDNToxR-Duet constructs from selective plates were chosen, inoculated in 5 mL of LB medium containing 100 μg/mL ampicillin and grown to an OD$_{600}$ of 0.2 at 37° C. with vigorous shaking. IPTG was added to the medium at a final concentration of 0.1 mM IPTG and grown to an OD$_{600}$ of 0.7. Purification, immunoblotting, CAT ELISA and MalE complementation assays are essentially as described previously. Li, R., Gorelik, R., Nanda, V., Law, P. B., Lear, J. D., DeGrado, W. F. and Bennett, J. S. *J. Biol. Chem.* 2004, 279, 26666-26673 (2004). For immunoblotting, anti-MBP (NEB) was used for pccKAN (TOXCAT) constructs, whereas anti-myc (Covance) and anti-HA (Covance) were used for pDNToxR-Duet constructs. CAT ELISA results are an average of 3 independent replicates.

Example 7

Phospholipid Bilayer Insertion

Also tested was the ability of anti-$\alpha_{IIb}$ to insert into phospholipid bilayer membranes and to bind and activate $\alpha_{IIb}\beta_3$ in intact platelets.

Fluorescence intensity was measured on an ATF 105 spectrofluorometer (Aviv Biomedical, Inc., Lakewood, N.J.) using a 0.3 cm path length cuvette. Small unilamellar vesicles composed of 1-Palmitoyl-2-Oleoyl-sn-Glycero-3-Phosphocholine and 1-Palmitoyl-2-Oleoyl-sn-Glycero-3-[Phospho-rac-(1-glycerol)] (7:3) were prepared using standard ethanol dilution (Batzri S & Korn E D. *Biochim. Biophys. Acta.* 298, 1015-1019 (1973)): phospholipids were initially dissolved in 15 µl ethanol and then diluted to 1 ml with buffer (20 mM HEPES, pH=7.5). Samples with 1 µM anti-$\alpha_{IIb}$ in the presence of 0, 100, and 500 µM total phospholipids were prepared. Excitation of 280 nm was used for emission scans ranging from 410 nm to 300 nm. Excitation and emission slit widths are 2.5 nm and 1.5 nm, respectively. An average time of 1.0 second was used.

Figure 9:
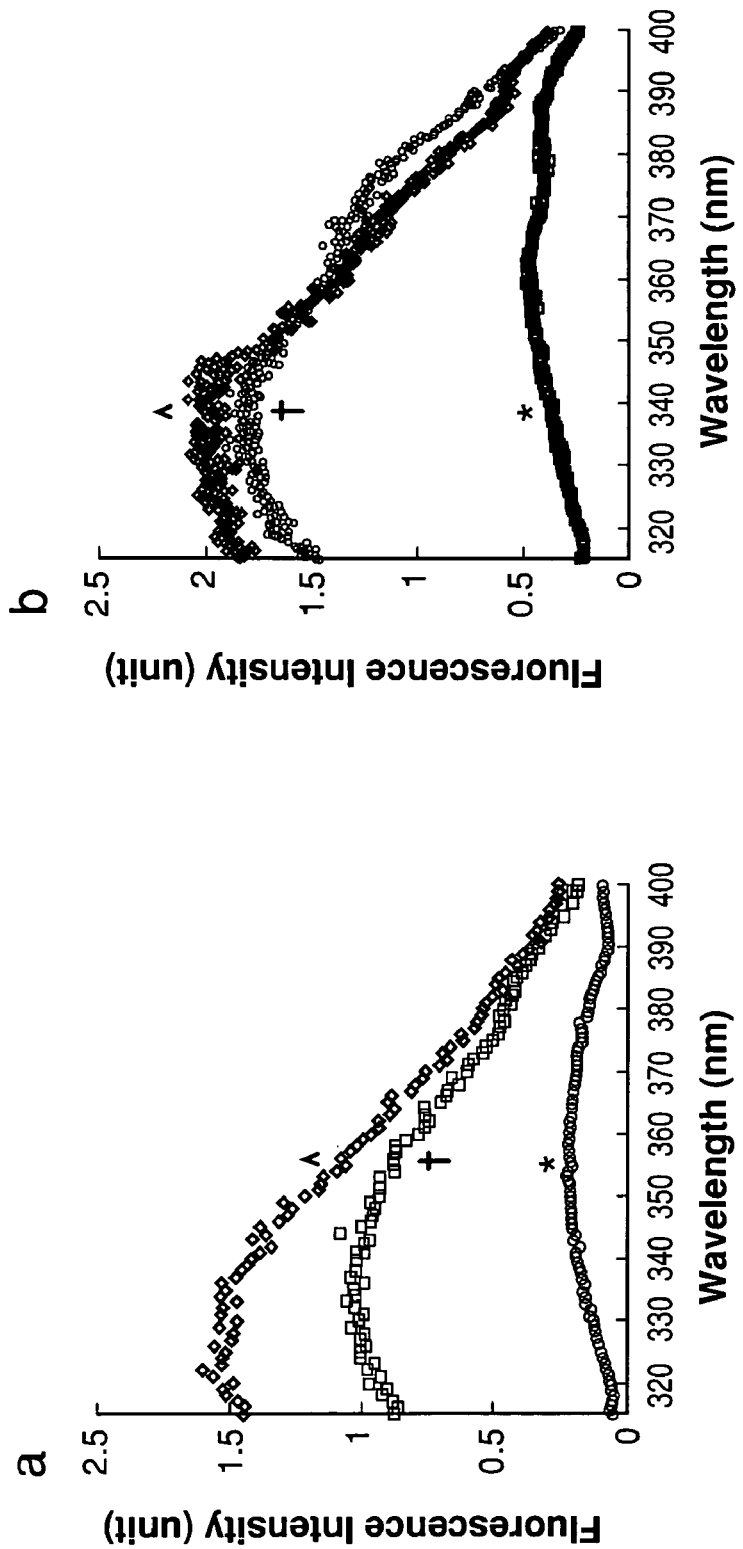
FIG. 9 supplies data indicating that the anti-$\alpha_{IIb}$ and the anti-$\alpha_V$ polypeptides successfully insert into phospholipids vesicles.

Measurements of Trp fluorescence intensity revealed that anti-$\alpha_{IIb}$ rapidly inserts into the hydrophobic region of small unilamellar vesicles composed of POPC and POPG (7:3). See FIG. 9, which provides the emission scans of anti-$\alpha_{IIb}$ (1 µM) and of anti-$\alpha_V$ in the presence of three different concentrations of phospholipids. Provided are emission scans of 1 µM anti-$\alpha_{IIb}$ (FIG. 9a) and 1 µM anti-$\alpha_V$ (FIG. 9b) in presence of 0 µM (*), 100 µM (†), and 500 µM (^) of phospholipids (POPC:POPG=7:3, excitation wavelength=280 nm). The emission maximum of the Trp residue in anti-$\alpha_{IIb}$ occurs at 353 nm, consistent with a fully-exposed Trp residue in the absence of membranes. In the presence of phospholipids vesicles, the emission maximum blue-shifts by 31 nm, indicating a transfer to a membrane-like environment. Concomitant with the peak shift, the maximum fluorescence intensity increased significantly, thereby indicating successful insertion.

Example 8

Hemolysis Assay

Because basic hydrophobic peptides can cause cell lysis (Bechinger B. *J. Membr. Biol.* 156, 197-211 (1997)), the hemolytic potential of inventive membrane protein-binding polypeptides was examined.

The hemolytic effects of the anti-$\alpha_{IIb}$, anti-$\alpha_{IIb}$scr, and anti-$\alpha_{IIb}$mut polypeptides were tested using a previously described method. See Liu D H & DeGrado W F *J. Am. Chem. Soc.* 123, 7553-7559 (2001). Suspension of human erythrocytes (RBC, 1%) with polypeptides of different concentrations were incubated in 150 mM NaCl and 10 mM Tris buffer (pH=7.0), in the presence or absence of bovine serum albumin. The samples were prepared by combining 400 µL of the RBC suspension and 10 µM of the polypeptide solutions. After incubation at 37° C. for 1 h, the samples were centrifuged at 14,000 rpm for 5 min, and the OD$_{400}$ of the supernatant was measured.

FIG. 10a depicts the results of human erythrocyte hemolysis as induced by increasing concentrations of anti-$\alpha_{IIb}$, anti-$\alpha_{IIb}$scr, and anti-$\alpha_{IIb}$mut in 10 mM Tris buffer (pH=7.0), 1 mg/mL bovine serum albumin. In FIG. 10b, the aggregation of gel-filtered human platelets induced by anti-$\alpha_{IIb}$mut (1 µM) in the absence and the presence of PGE1 or apyrase.

$\alpha_{IIb}$-TM and anti-$\alpha_{IIb}$ both failed to lyse erythrocytes and platelets at concentrations as high as 10 µM. However, anti-$\alpha_{IIb}$mut was toxic at concentrations greater than 1.0 µM, possibly due to its increased hydrophobicity. Therefore, the scrambled polypeptide anti-$\alpha_{IIb}$scr was employed as the control peptide for platelet aggregation studies (Example 9, infra).

Example 9

Platelet Aggregation

Figure 4:
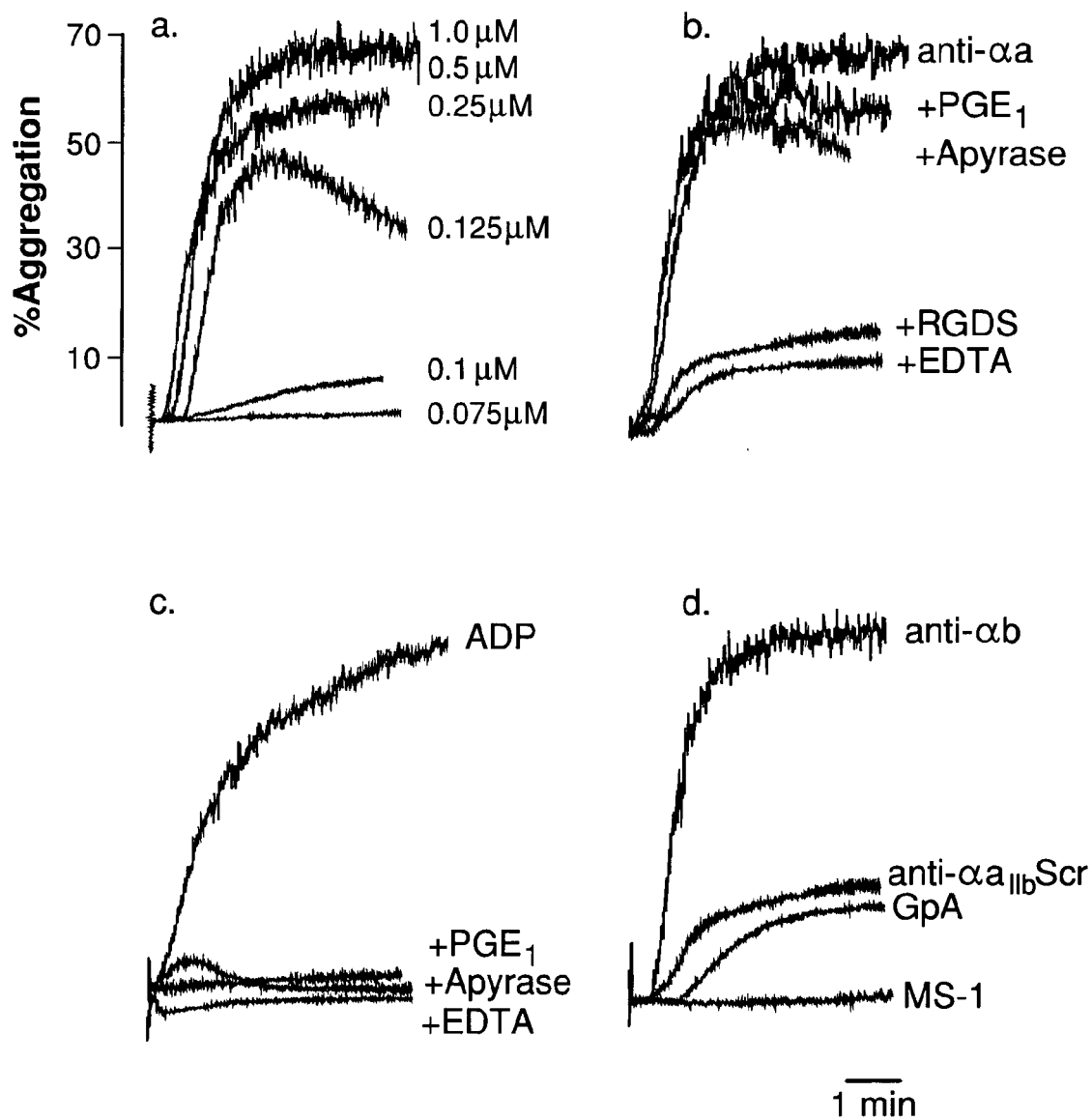
FIG. 4 supplies data indicating that incubation of human platelets with anti-$\alpha_{IIb}$ polypeptide induces platelet aggregation.

Platelets undergo rapid $\alpha_{IIb}\beta_3$-dependent aggregation in response to agonists such as ADP, a process that can be inhibited by the signal transduction inhibitor PGE$_1$, the ADPase apyrase, or the divalent cation chelator EDTA (FIG. 4). Bennett, J. S. *Annu. Rev. Med.* 52, 161-184 (2001).

Platelet-rich plasma, prepared from human blood anti-coagulated with 0.1 volume of 0.13 M sodium citrate, was gel-filtered on Sepharose 2B (Amersham Biosciences, Piscataway, N.J.) using an elution buffer containing 137 mM NaCl, 2.7 mM KCl, 1 mM MgCl$_2$, 5.6 mM glucose, 0.35 mg/ml bovine serum albumin, 3.3 mM NaH$_2$PO$_4$, and 4 mM HEPES (pH=7.4), as previously described. Jordan P et al. *Nature* 411, 909-917 (2001). Turbidometric measurements of platelet aggregation were performed in a Chrono-Log Lumi-Dual Aggregometer. Aliquots (0.4 ml) of the gel-filtered platelet suspension were supplemented with 200 µg/ml human fibrinogen (Enzyme Research Labs., South Bend, Ind.) and 1 mM CaCl$_2$ (final concentrations) prior to adding platelet agonists. The polypeptide was added from a DMSO solution such that the final concentration of DMSO was no greater than 0.5%. All controls also had 0.5% DMSO in the buffer.

Adding anti-$\alpha_{IIB}$ to suspensions of gel-filtered human platelets at polypeptide concentrations between 100 nM and 200 nM induced platelet aggregation in a dose-dependent manner (FIG. 4a). The steepness of the response over a narrow range of polypeptide concentration is consistent with the highly multivalent nature of $\alpha_{IIb}\beta_3$-dependent platelet aggregation. Bennett, J. S. *J. Clin. Invest.* 115, 3363-3369 (2005). In contrast to ADP-induced aggregation, anti-$\alpha_{IIb}$-induced aggregation was only minimally affected by PGE$_1$ and apyrase, indicating that it was independent of platelet signal transduction or secreted ADP (FIG. 4b). Nonetheless, anti-$\alpha_{IIb}$-induced aggregation was inhibited by agents that directly target $\alpha_{IIb}\beta_3$, including EDTA, the tetrapeptide Arg-Gly-Asp-Ser (SEQ ID NO:41), and the monoclonal, $\alpha_{IIb}\beta_3$-specific antibody A$_2$A$_9$ (data not shown; see Bennett, J. S. *Annu. Rev. Med.* 52, 161-184 (2001)). Such inhibition confirms that anti-$\alpha_{IIb}$-induced platelet aggregation is mediated by $\alpha_{IIb}\beta_3$.

The specificity of the aggregation response to anti-$\alpha_{IIb}$ was verified using anti-$\alpha_{IIb}$scr as well as a variety of unrelated membrane peptides. These include, as shown in FIG. 4d, MS1, a model membrane peptide that forms dimers and trimers in membranes (Choma C et al. *Nat. Struct. Biol.* 7, 161-166 (2000)), and GpA, a peptide corresponding to residues Ile73-Ile95 of the glycophorin A TM domain. MacKenzie K R et al. *Science* 276, 131-133 (1997). These control peptides caused an aggregation response similar to the nonspecific response observed with anti-$\alpha_{IIb}$ plus EDTA. The GpA peptide is noteworthy because it also contains a GXXXG (SEQ ID NO:12) motif. See MacKenzie K R et al.

(1997). Thus, although the GXXXG (SEQ ID NO:12) sequence provides a framework for association, the surrounding sequence modulates affinity and specificity. Curran A R & Engelman D M. *Curr. Opin. Struct. Biol.* 13, 412-417 (2003). Finally, $\alpha_{IIb}$-TM has been shown to induce platelet aggregation (Yin H. et al. *Blood* 106, 116a (2005)) but is substantially less potent than the designed polypeptide, anti-$\alpha_{IIb}$.

FIG. 4 depicts the results of the assay designed to assess anti-$\alpha_{IIb}$-induced platelet aggregation. FIG. 4a shows that the aggregation of gel-filtered human platelets was induced by increasing concentrations of the anti-$\alpha_{IIb}$ polypeptide. As shown in FIGS. 4b and 4c, to differentiate between a direct effect of anti-$\alpha_{IIb}$ on $\alpha_{IIb}\beta_3$ versus anti-$\alpha_{IIb}$-stimulated signal transduction, platelet aggregation induced by 1 µM anti-$\alpha_{IIb}$ either alone or in the presence of 2 µM PGE1, 10 units/ml apyrase, 1 mM Arg-Gly-Asp-Ser (RGDS) (SEQ ID NO:41), or 2.5 mM EDTA, was compared to platelet aggregation induced by 10 µM ADP in the presence of the same inhibitors. FIG. 4d depicts a comparison of platelet aggregation induced by 1 µM anti-$\alpha_{IIb}$ with the effect of a scrambled anti-$\alpha_{IIb}$ polypeptide (anti-$\alpha_{IIb}$scr), a polypeptide corresponding the TM domain of glycophorin A (GpA), and the TM helix MS1.

Figure 15:
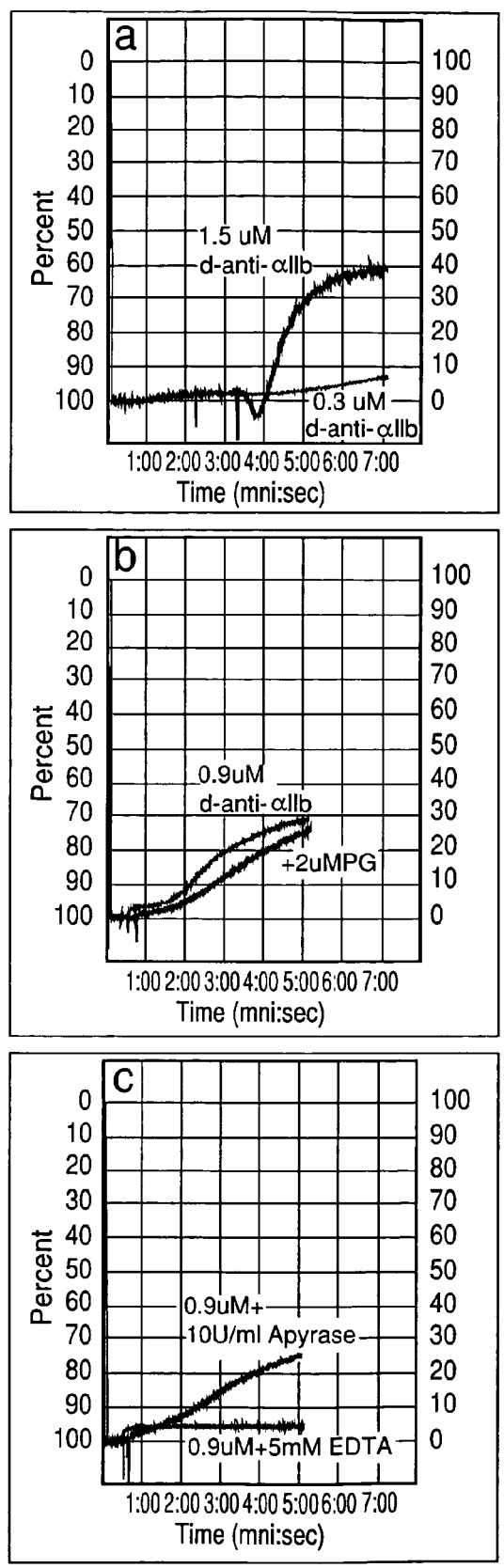
FIG. 15 depicts the results of an assay designed to assess d-anti-$\alpha_{IIb}$-induced platelet aggregation.

FIG. 15 depicts the results of an assay designed to assess d-anti-$\alpha_{IIb}$-induced platelet aggregation. FIG. 15a shows that the aggregation of gel-filtered human platelets was induced by increasing concentrations of the d-anti-$\alpha_{IIb}$ polypeptide. As shown in FIGS. 15b and 15c, to differentiate between a direct effect of d-anti-$\alpha_{IIb}$ on $\alpha_{IIb}\beta_3$ versus d-anti-$\alpha_{IIb}$-stimulated signal transduction, platelet aggregation induced by 0.9 µM d-anti-$\alpha_{IIb}$ either alone or in the presence of 2 µM PGE1 or 10 units/ml apyrase, or 5 mM EDTA. The affect can be compared to that of ADP shown in FIG. 4.

Figure 11:
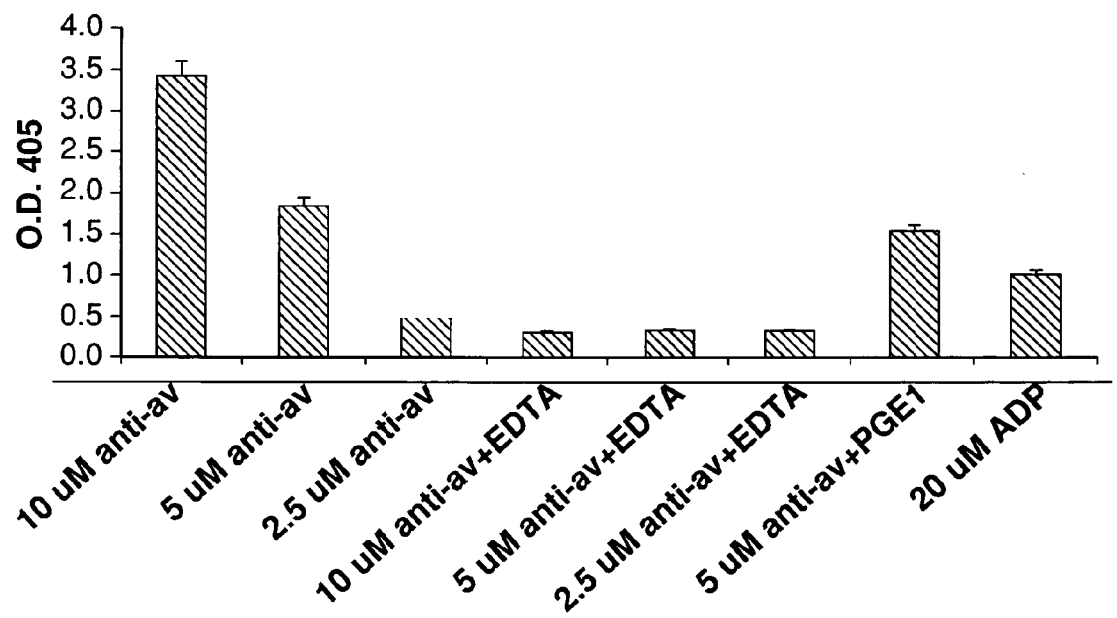
FIG. 11 demonstrates that the anti-αv polypeptide induces platelet adhesion to immobilized osteopontin in a manner that is independent of platelet signal transduction.
Figure 13:
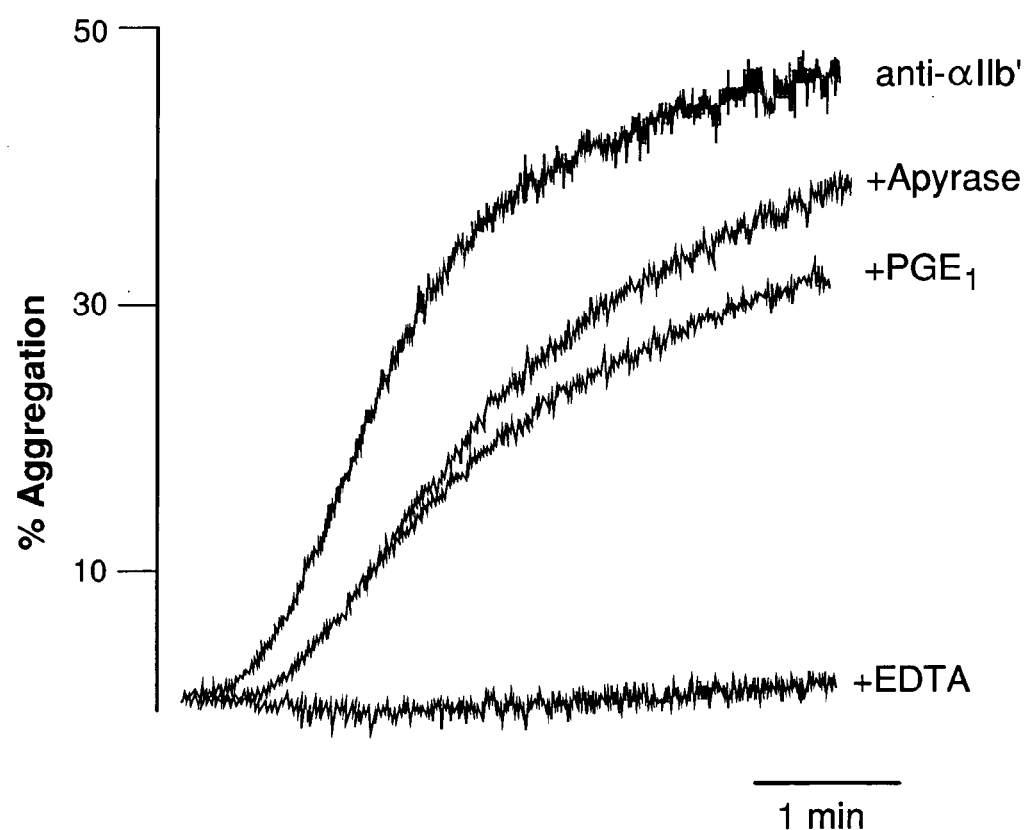
FIG. 13 evaluates anti-$\alpha_{IIb}$'-induced platelet aggregation.

The integrin $\alpha_V\beta_3$ mediates adhesion of platelets to the matrix protein osteopontin, potentially exposed to the circulating blood by rupture of an atherosclerotic plaque. Incubating platelets with anti-$\alpha_V$ induced robust platelet adhesion to osteopontin, even in the absence of pharmacological platelet agonists. The potency of anti-$\alpha v$ in inducing platelet adhesion to osteopontin was approximately 10-fold lower than that of anti-$\alpha_{IIb}$ in inducing platelet aggregation (FIG. 11). Adhesion of platelets in 100 µl aliquots of gel-filtered human platelets to immobilized osteopontin was induced by the indicated concentrations of anti-$\alpha_V$, either alone or in the presence of the calcium chelator 2.5 mM EDTA or the global platelet signal transduction inhibitor 2 µM $PGE_1$. Platelets stimulated by 20 µM ADP served as a positive control. Platelet adhesion was quantitated using a colorimetric assay based on measurement of platelet acid phosphatase activity. The data shown in FIG. 11 are the mean and standard error of measurements made in triplicate. Anti-$\alpha_V$-induced adhesion was prevented by agents that inhibit the interaction of $\alpha_V\beta_3$'s extracellular ligand-binding site with osteopontin, including EDTA or the specific RGD-containing $\alpha_V\beta_3$ antagonist XJ735, confirming that anti-$\alpha_V$ induced platelet adhesion to osteopontin is mediated by $\alpha_V\beta3$.

Example 10

FACS Analysis

Figure 10:
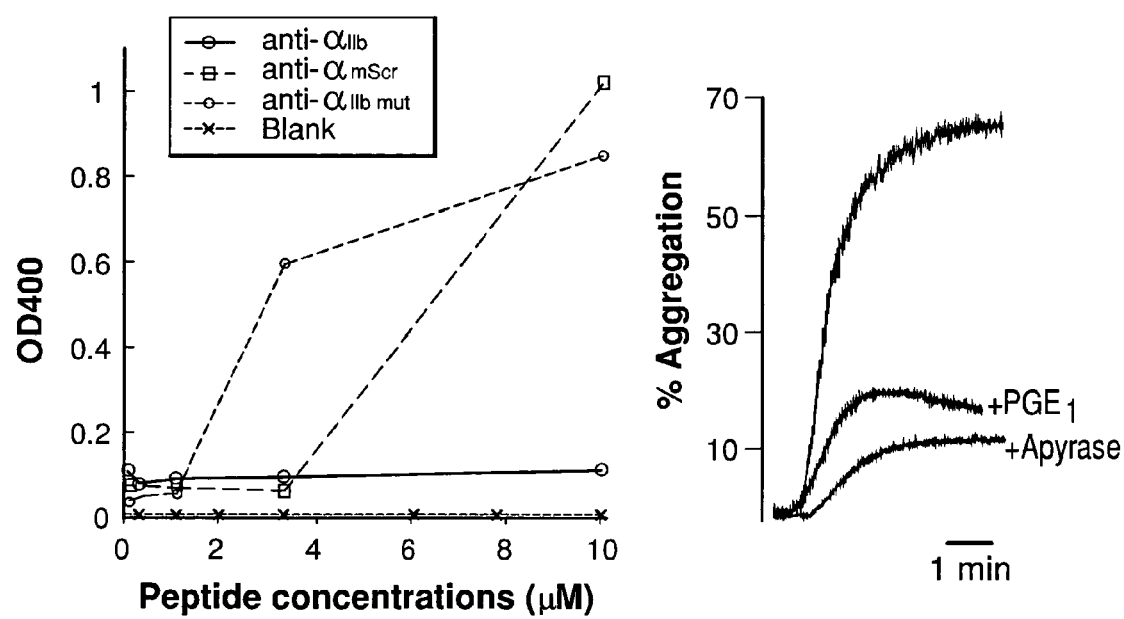
FIG. 10 provides the results of an assay to evaluate whether the inventive polypeptides induce hemolysis.

Fluorescence activated cell sorting (FACS) analyses further confirmed that anti-$\alpha_{IIb}$ caused platelets to bind to fibrinogen in an integrin $\alpha_{IIb}\beta_3$-dependent manner (FIG. 10). In the presence of 2.0 µM anti-$\alpha_{IIb}$ polypeptide, platelets bound comparable amounts of FITC-labeled fibrinogen as compared to platelets stimulated by 20 µM ADP. The anti-$\alpha_{IIb}$-induced fibrinogen binding was prevented by EDTA, consistent with fibrinogen binding to $\alpha_{IIb}\beta_3$.

Freshly isolated platelets were added to 200 µg/ml FITC-conjugated fibrinogen, then incubated with 20 µM ADP or 2 µM of the anti-$\alpha_{IIb}$ polypeptide in the presence or in the absence of 5 mM EDTA for 3 min at room temperature. After incubation, the platelets were fixed with 0.37% formalin in PBS buffer for 10 min, then washed and examined by FACS analysis as previously reported. See Ulmschneider M B et al. *Proteins: Struct. Funct. Bioinformat.* 59, 252-265 (2005). The polypeptide was added from a DMSO solution such that the final concentration of DMSO was no greater than 0.5%. All controls also had 0.5% DMSO in the buffer.

Example 11

Force Spectroscopy

Force spectroscopy (laser tweezers) was used to probe the platelet response to anti-$\alpha_{IIb}$ at the single molecule level, in order to demonstrate the specificity of anti-$\alpha_{IIb}$ for inducing an active conformation in $\alpha_{IIb}\beta_3$ A custom-built laser tweezers setup assembled from a Nikon Diaphot 300 inverted microscope, 100×1.3NA Fluor lens and a Spectra Physics FCBar Nd:YAG laser was used to measure the strength of osteopontin ("OPN") and fibrinogen binding to unstimulated and stimulated human platelets or Chinese hamster ovary (CHO) cells. Litvinov R I et al. *Proc. Natl. Acad. Sci. USA.* 99, 7426-31 (2002). Recombinant human OPN, prepared as previously described (Bennett J S et al. *J. Biol. Chem.* 272, 8137-40 (1997)) or purified human fibrinogen was covalently bound to 0.93 µm carboxylate-modified latex beads. Individual cells, trapped from a suspension of gel filtered human platelets or CHO cells, were manually attached to 5 µm diameter silica pedestals coated with polylysine. An OPN- or fibrinogen-coated bead, trapped by the laser light, was then brought into proximity of an immobilized cell, oscillated at 50 Hz, and then brought into repeated intermittent contact with the cell by micromanipulation. Data collection was initiated at the first contact between the bead and the cell. Rupture forces following repeated contacts were collected for periods of several seconds to one minute. Individual forces measured during each contact-detachment cycle were collected into 10 pN-wide bins. The number of events in each bin was then plotted against the average force for that bin after normalizing for the total number of interaction cycles. Thus, the percentage of events in a particular force range (bin) represents the probability of rupture events at that tension. Optical artifacts observed with or without trapped latex beads produce signals that appeared as forces below 10 pN. Therefore, rupture forces in this range were not considered when the data were analyzed. The polypeptide was added from a DMSO solution such that the final concentration of DMSO was no greater than 0.5%. All controls also had 0.5% DMSO in the buffer.

Platelets express a second integrin with a $\beta_3$ subunit, $\alpha_V\beta_3$, which can bind the matrix protein osteopontin when platelets are stimulated by $Mn^{2+}$ or ADP. Bennett J S et al. *J. Biol. Chem.* 272, 8137-8140 (1997). To test the ability of anti-$\alpha_{IIb}$ to discriminate between $\alpha_{IIb}\beta_3$ and $\alpha_V\beta_3$, the rupture force between platelets and osteopontin-coated beads in the presence and absence of anti-$\alpha_{IIb}$ was measured.

Platelet adhesion to osteopontin was measured as previously described. See Fleming K G *J. Mol. Biol.* 323, 563-571 (2002). Briefly, 96-well flat bottom microtiter plates (Immulon 2, Dynatech, Chantilly Va.) were coated with 5 µg/ml of recombinant osteopontin dissolved in 50 mM $NaHCO_3$ buffer, pH 8.0, containing 150 mM NaCl. Unoccupied protein binding sites on the wells were blocked with 5 mg/ml bovine serum albumin dissolved in the same buffer. One hundred μl aliquots of a gel-filtered platelet suspension containing ≈2-5×10$^6$ platelets were added to the protein-coated wells in the absence or presence of anti-α$_V$ or ADP. Following an incubation for 30 min at 37° C. without agitation, the plates were washed four times and the number of adherent platelets measured using a colorimetric assay that measure platelet acid phosphatase activity. The polypeptide was added from a DMSO solution such that the final concentration of DMSO was no greater than 0.5%. All controls also had 0.5% DMSO in the buffer.

Figure 5:
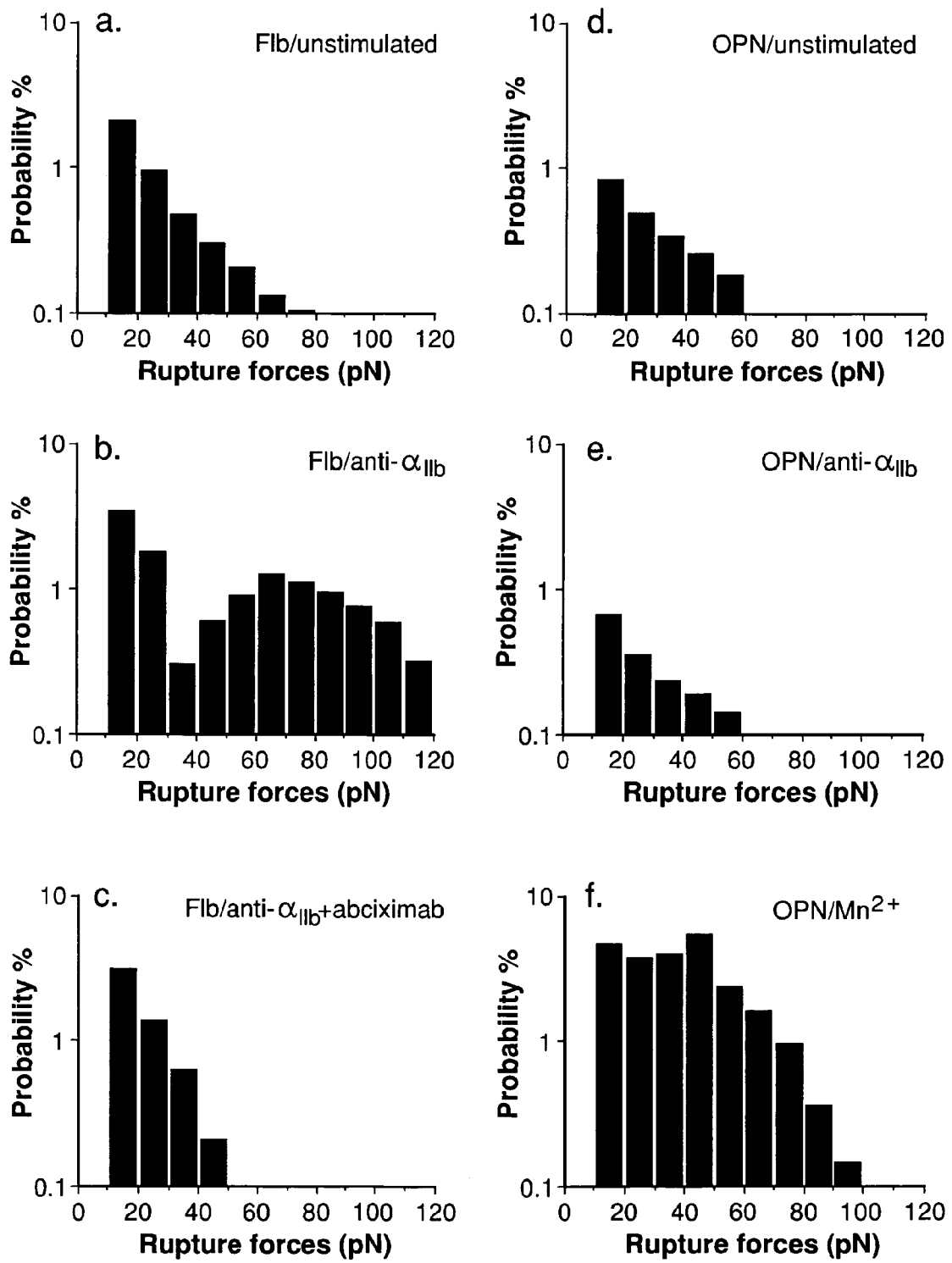
FIG. 5 demonstrates that anti-$\alpha_{IIb}$ induces fibrinogen binding to $\alpha_{IIb}\beta_3$, but not to osteopontin.

FIG. 5 provides data showing that anti-α$_{IIb}$ induces fibrinogen binding to α$_{IIb}$β$_3$, but not osteopontin binding to α$_V$β$_3$. Distribution of rupture forces between platelets and beads coated with fibrinogen ("Fib", FIGS. 5a-5c), an α$_{IIb}$β$_3$ ligand, or osteopontin ("OPN", FIGS. 5d-5f), an α$_V$β$_3$ ligand, were measured using laser tweezers. FIGS. 5a & 5d depict rupture forces in the absence of anti-α$_{IIb}$. FIGS. 5b & 5e depict rupture forces measured in the presence of 0.5 μM anti-α$_{IIb}$. FIG. 5c shows the effect of the α$_{IIb}$β$_3$ antagonist abciximab on the anti-α$_{IIb}$-induced interaction of platelets with fibrinogen-coated beads. FIG. 5f provides rupture forces between platelets and osteopontin-coated beads in the presence of 1.0 mM Mn$^{2+}$.

Beads coated with fibrinogen were brought into intermittent contact with immobilized platelets in the presence or absence of anti-α$_{IIb}$ and the rupture force was measured. Litvinov R I et al. *J. Biol. Chem.* 278, 51285-51290 (2003). In the absence of anti-α$_{IIb}$, the binding probability of platelets and fibrinogen-coated beads decreased exponentially (FIG. 5a) with increasing force, consistent with a non-specific interaction of the beads with the platelet surface. Litvinov R I (2003). However, in the presence of 0.5 μM anti-α$_{IIb}$, a peak near 70 pN was observed (FIG. 5b), similar to the peak of specific rupture force observed in the presence of ADP. Litvinov R I (2003). By contrast, there was no significant activation caused either by anti-α$_{IIb}$scr or by anti-α$_{IIb}$mut under sublytic concentrations. Moreover, pre-incubation of the platelets with the ligand-blocking α$_{IIb}$β$_3$ antibody, abciximab, eliminated the rupture force peak (FIG. 5c), confirming that the peak resulted from fibrinogen binding to the activated conformation of α$_{IIb}$β$_3$.

No peak of rupture force was observed between platelets and osteopontin coated beads either in the absence (FIG. 5d) or presence of anti-α$_{IIb}$ (FIG. 5e). However, exposing the platelets to 1 mM Mn$^{2+}$ produced a characteristic peak of rupture force between osteopontin and activated α$_V$β$_3$ (most probable value ≈45 pN (see Litvinov R I. et al. *J. Biol. Chem.* 278, 51285-90 (2003)); FIG. 5f). Thus, these results indicate that anti-α$_{IIb}$ can specifically recognize am when other homologous integrins are present.

Laser tweezers were also used to corroborate that the ability of anti-α$_{IIb}$ to activate α$_{IIb}$β$_3$ is independent of signal transduction.

Fibrinogen-coated beads were brought into intermittent contact with the surface of Chinese hamster ovary (CHO) cells expressing α$_{IIb}$β$_3$. Recombinant α$_{IIb}$β$_3$ expressed by CHO cells is inactive and cannot be activated by cellular agonists. Li et al. *Proc. Natl. Acad. Sci. USA* 102, 1424-1429 (2005). However, in the presence of anti-α$_{IIb}$, there was a peak of rupture force identical to that seen when platelets were incubated with ADP (FIG. 11). This peak resulted from fibrinogen binding to activate α$_{IIb}$β$_3$ because it was not present when the CHO cells were pre-incubated with the αa$_{IIb}$β$_3$ antagonist abciximab.

FIG. 11 therefore demonstrates that anti-α$_{IIb}$ induces fibrinogen binding to CHO cells expressing α$_{IIb}$β$_3$. Shown is the distribution of rupture forces between transfected CHO cells and beads coated with fibrinogen. The top panel illustrates the data for 0.5 μM anti-α$_{IIb}$ polypeptide; the bottom panel shows data for 0.5 μM anti-α$_{IIb}$ polypeptide plus abciximab (200 μg/ml).

The preceding data demonstrate the successful application of the computational design of a membrane protein-binding polypeptide that inserts into biological membranes and binds to its target with high affinity and specificity. Previous investigators have shown that peptides derived from the TM regions of oligomeric proteins can disrupt lateral assembly of the native complex. Partridge A W et al. *J. Biol. Chem.* 278, 22056-60 (2003); Manolios N et al. *Nat. Med.* 3, 84-88 (1997); Gerber D et al. *FASEB J* 19, 1190-1192 (2005). However, in comparison to the membrane protein-binding polypeptide, high concentrations of these TM polypeptides were required to elicit the desired response, and only partial inhibition was achieved. Similarly, we have found that polypeptides from the TM regions of α$_{IIb}$ and β$_3$ are substantially weaker activators of α$_{IIb}$β$_3$ than anti-α$_{IIb}$.

More generally, membrane protein-binding polypeptides provide a general route to molecules that bind TM regions of their targets, expanding the range of conventional antibody-based methods, which are only able to target water-soluble regions of proteins. Given the growing appreciation of lateral TM helix associations in membrane protein folding, assembly, and signal transduction (see, e.g., Senes A et al. *Curr. Opin. Struct. Biol.* 14, 465-479 (2004)), membrane protein-binding polypeptides provide much-needed reagents for probing these processes. Furthermore, the membrane protein-binding polypeptides represent the basis for new applications with regard to clinical diagnostics and therapeutics.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method of preparing a novel polypeptide that binds to a helical transmembrane region of a membrane protein comprising:

identifying a site of interest on a helical transmembrane region of the membrane protein;

based on said site of interest, selecting a starting backbone conformation, thereby obtaining a template helical pair comprising a first helix and a second helix, wherein said first helix and said second helix interact via said site of interest;

threading an amino acid sequence corresponding to the helical transmembrane region, including the site of interest, onto said first helix;

selecting a second amino acid sequence for said second helix using a repacking algorithm; and, synthesizing said novel polypeptide based on the selection of said second amino acid sequence.

2. The method according to claim 1, wherein said second amino acid sequence comprises helix-helix interface residues and membrane-exposed residues.

3. The method according to claim 2, wherein said helix-helix interface residues are determined using a computational design algorithm and said membrane-exposed residues are determined via random selection of residues.

4. The method according to claim 1 further comprising appending at least one water solubility enhancing function to said second helix.

5. The method according to claim 4 wherein the function is bonded (helto at least one of the carbon and nitrogen termini of the polypeptide.

6. The method according to claim 5 wherein said threading further comprises positioning said site of interest so that it lies along a position of said first helix that maintains the closest approach between said first helix and said second helix.

7. The method according to claim 5 comprising obtaining multiple template helical pairs and performing said threading and said repacking steps with respect to each template helical pair.

8. The method according to claim 7 further comprising determining which of said template helical pairs are capable of reaching a low energy solution.

9. The method according to claim 8 further comprising threading an amino acid sequence corresponding to the site of interest onto said first helix minimizing said template helical pairs that are capable of reaching a low energy solution, said template helical pairs having side chains; and, selecting said side chains of said template helical pairs using a repacking algorithm.

10. The method according to claim 8 further comprising minimizing said template helical pairs a second time, and selecting a subset of said helical pairs based on geometric qualifications.

11. The method according to claim 10 further comprising, using the helical pairs included within said subset; threading an amino acid sequence corresponding to the site of interest onto said first helix of each helical pair; and, selecting a second amino acid sequence for said second helix using a repacking algorithm.

12. A method of preparing a novel polypeptide that binds to a helical transmembrane region of a membrane protein comprising:

identifying a site of interest on a helical transmembrane region of the membrane protein;

based on said site of interest, selecting a starting backbone conformation, thereby obtaining a template helical pair comprising a first helix and a second helix, wherein said first helix and said second helix interact via said site of interest;

substituting for said second helix a polypeptide comprising at least one d-amino acid, wherein said polypeptide and said first helix interact through said site of interest threading an amino acid sequence corresponding to the helical transmembrane region, including the site of interest, onto said first helix;

selecting a second amino acid sequence for said polypeptide using a repacking algorithm; and, synthesizing said novel polypeptide based on the selection of said second amino acid sequence.

13. The method of claim 12 wherein said polypeptide comprises multiple d-amino acids.

\* \* \* \* \*